United States Patent
Hu et al.

(10) Patent No.: US 12,329,826 B2
(45) Date of Patent: Jun. 17, 2025

(54) THERAPEUTIC AGENTS COMPRISING NUCLEIC ACIDS AND CAR-MODIFIED IMMUNE CELLS, AND USES THEREOF

(71) Applicant: HANGZHOU CONVERD CO., LTD., Zhejiang (CN)

(72) Inventors: Fang Hu, Zhejiang (CN); Can Chen, Zhejiang (CN); Lin Xiao, Zhejiang (CN); Jin Fu, Zhejiang (CN); Rong Zhang, Zhejiang (CN); Jinlu Cai, Zhejiang (CN)

(73) Assignee: HANGZHOU CONVERD CO., LTD., Zhejiang (CN)

( * ) Notice: Subject to any disclaimer, the term of this patent is extended or adjusted under 35 U.S.C. 154(b) by 1148 days.

(21) Appl. No.: 17/270,924

(22) PCT Filed: Aug. 26, 2019

(86) PCT No.: PCT/CN2019/102480
§ 371 (c)(1),
(2) Date: Feb. 24, 2021

(87) PCT Pub. No.: WO2020/038490
PCT Pub. Date: Feb. 27, 2020

(65) Prior Publication Data
US 2023/0321238 A1 Oct. 12, 2023

(30) Foreign Application Priority Data
Aug. 24, 2018 (CN) .......................... 201810972140.3

(51) Int. Cl.
| | | |
|---|---|---|
| *A61K 40/31* | (2025.01) | |
| *A61K 35/17* | (2015.01) | |
| *A61K 38/17* | (2006.01) | |
| *A61K 39/00* | (2006.01) | |
| *A61K 40/11* | (2025.01) | |
| *A61K 40/15* | (2025.01) | |
| *A61K 40/42* | (2025.01) | |
| *A61K 47/68* | (2017.01) | |
| *A61K 48/00* | (2006.01) | |
| *A61P 35/00* | (2006.01) | |
| *C12N 5/0783* | (2010.01) | |

(52) U.S. Cl.
CPC .......... *A61K 47/6891* (2017.08); *A61K 35/17* (2013.01); *A61K 38/1774* (2013.01); *A61K 39/0011* (2013.01); *A61K 40/11* (2025.01); *A61K 40/15* (2025.01); *A61K 40/31* (2025.01); *A61K 40/42* (2025.01); *A61K 48/0058* (2013.01); *A61P 35/00* (2018.01); *C12N 5/0636* (2013.01); *C12N 5/0638* (2013.01); *C12N 5/0646* (2013.01); *A61K 2239/31* (2023.05); *A61K 2239/38* (2023.05); *A61K 2239/50* (2023.05); *A61K 2239/59* (2023.05)

(58) Field of Classification Search
None
See application file for complete search history.

(56) References Cited

U.S. PATENT DOCUMENTS

| | | | |
|---|---|---|---|
| 10,494,434 B2 * | 12/2019 | Riddell | ................ C12N 5/0636 |
| 11,384,156 B2 * | 7/2022 | Ma | ............................ G02F 1/09 |
| 2016/0208012 A1 | 6/2016 | June et al. | |
| 2017/0042093 A1 | 2/2017 | Chapon et al. | |
| 2017/0042993 A1 | 2/2017 | Lawman et al. | |
| 2018/0169109 A1 | 6/2018 | Bradner et al. | |
| 2019/0048061 A1 * | 2/2019 | Smeland | ............ A61K 39/4613 |
| 2019/0365805 A1 | 12/2019 | Coombs | |

FOREIGN PATENT DOCUMENTS

| | | |
|---|---|---|
| CN | 103933558 A | 7/2014 |
| CN | 106220739 A | 12/2016 |
| CN | 107759701 A | 3/2018 |
| CN | 107847577 A | 3/2018 |

(Continued)

OTHER PUBLICATIONS

Extended European Search Report dated May 30, 2022, for corresponding European Patent Application No. 19852951.3.
Notice of Reasons for Refusal drafted Feb. 8, 2023, for corresponding Japanese Patent Application No. 2021-510012.
Kemeng Wang et al.; CD19: a biomarker for B cell development, lymphoma diagnosis and therapy; Experimental Hematology & Oncology; 2012; pp. 1-8.
Second Office Action dated Mar. 30, 2024, for Chinese Patent Application No. 201980052439.X.

(Continued)

*Primary Examiner* — Mark Halvorson
(74) *Attorney, Agent, or Firm* — Renner, Otto, Boisselle & Sklar, LLP

(57) ABSTRACT

Provided are therapeutic agent including nucleic acid and CAR-modified immune cell and the use thereof. The therapeutic agent comprises first composition and second composition, the first composition comprises a nucleic acid having a labeling polypeptide coding sequence for being introduced into a tumor cell and/or a cancer cell; the labeling polypeptide has an extracellular antigen determining region, a spacer portion, and a transmembrane portion that are operatively linked, which can be expressed to form modification on the surface of the tumor cell and/or cancer cell; the extracellular antigen determining region comprises one or more epitope polypeptides; wherein, amino acid sequences of proteins on cell membrane or secreted proteins of mammal do not comprise the epitope polypeptide amino acid sequence in the natural state; the second composition comprises chimeric antigen receptor modified immune cell which specifically recognize and bind to the extracellular antigen determining region. The therapeutic agent achieves synergistic therapeutic effect.

17 Claims, 24 Drawing Sheets
Specification includes a Sequence Listing.

(56) References Cited

FOREIGN PATENT DOCUMENTS

| | | | |
|---|---|---|---|
| CN | 108350062 | A | 7/2018 |
| CN | 108350462 | A | 7/2018 |
| EP | 0733373 | A2 | 9/1996 |
| JP | 2014504294 | A | 2/2014 |
| WO | 2005097997 | A1 | 10/2005 |
| WO | WO 2007/101227 | * | 9/2007 |
| WO | 2007111421 | A1 | 10/2007 |
| WO | 2012166617 | A2 | 12/2012 |
| WO | 2014186596 | A2 | 11/2014 |
| WO | 2015077789 | A2 | 5/2015 |
| WO | WO 2015/150526 | * | 10/2015 |
| WO | 2017075440 | A1 | 5/2017 |
| WO | 2017/177204 | A1 | 10/2017 |
| WO | 2019080537 | A1 | 5/2019 |

First Office Action issued Jul. 15, 2021, for corresponding Chinese Patent Application No. 201810972140.3.
English Translation of International Search Report issued Nov. 28, 2019, for related International Patent Application No. PCT/CN2019/102480.

* cited by examiner

A

B

C

D

SEQUENCE LISTING

```
<160> NUMBER OF SEQ ID NOS: 62

<210> SEQ ID NO 1
<211> LENGTH: 58
<212> TYPE: PRT
<213> ORGANISM: Artificial sequence
<220> FEATURE:
<223> OTHER INFORMATION: The sequence is synthesized

<400> SEQUENCE: 1
```

Gly Ala His Ala Asp Ile Thr Ser Glu Gln Lys Leu Ile Ser Glu Glu
1               5                   10                  15

Asp Leu Gly Gly Gly Gly Ser Gly Gly Gly Ser Glu Gln Lys Leu
            20                  25                  30

Ile Ser Glu Glu Asp Leu Gly Gly Gly Ser Gly Gly Gly Ser
        35                  40                  45

Glu Gln Lys Leu Ile Ser Glu Glu Asp Leu
    50                  55

<210> SEQ ID NO 2
<211> LENGTH: 55
<212> TYPE: PRT
<213> ORGANISM: Artificial sequence
<220> FEATURE:
<223> OTHER INFORMATION: The sequence is synthesized

<400> SEQUENCE: 2

Gly Ala His Ala Asp Ile Thr Ser Tyr Pro Tyr Asp Val Pro Asp Tyr
1               5                   10                  15

Ala Gly Gly Gly Gly Ser Gly Gly Gly Ser Tyr Pro Tyr Asp Val
            20                  25                  30

Pro Asp Tyr Ala Gly Gly Gly Ser Gly Gly Gly Ser Tyr Pro
        35                  40                  45

Tyr Asp Val Pro Asp Tyr Ala
    50                  55

<210> SEQ ID NO 3
<211> LENGTH: 55
<212> TYPE: PRT
<213> ORGANISM: Artificial sequence
<220> FEATURE:
<223> OTHER INFORMATION: The sequence is synthesized

<400> SEQUENCE: 3

Gly Ala His Ala Asp Ile Thr Ser Asn Trp Ser His Pro Gln Phe Glu
1               5                   10                  15

Lys Gly Gly Gly Gly Ser Gly Gly Gly Ser Asn Trp Ser His Pro
            20                  25                  30

Gln Phe Glu Lys Gly Gly Gly Ser Gly Gly Gly Ser Asn Trp
        35                  40                  45

Ser His Pro Gln Phe Glu Lys
    50                  55

<210> SEQ ID NO 4
<211> LENGTH: 78
<212> TYPE: PRT
<213> ORGANISM: Artificial sequence
<220> FEATURE:
<223> OTHER INFORMATION: The sequence is synthesized

<400> SEQUENCE: 4

Gly Ala His Ala Ala Gln Leu Thr Leu Thr Lys Gly Asn Lys Glu Gln
1               5                   10                  15

Lys Leu Ile Ser Glu Glu Asp Leu Gly Glu Gln Lys Leu Ile Ser Glu
            20                  25                  30

Glu Asp Leu Gly Glu Gln Lys Leu Ile Ser Glu Glu Asp Leu Gly Gly
        35                  40                  45

Ser Tyr Pro Tyr Asp Val Pro Asp Tyr Ala Gly Tyr Pro Tyr Asp Val
    50                  55                  60

Pro Asp Tyr Ala Gly Tyr Pro Tyr Asp Val Pro Asp Tyr Ala 65          70          75

<210> SEQ ID NO 5
<211> LENGTH: 47
<212> TYPE: PRT
<213> ORGANISM: Artificial sequence
<220> FEATURE:
<223> OTHER INFORMATION: The sequence is synthesized

<400> SEQUENCE: 5

Gly Ala His Ala Glu Gln Lys Leu Ile Ser Glu Glu Asp Leu Gly Glu
1               5                   10                  15

Gln Lys Leu Ile Ser Glu Glu Asp Leu Gly Gly Ser Tyr Pro Tyr Asp
            20                  25                  30

Val Pro Asp Tyr Ala Gly Tyr Pro Tyr Asp Val Pro Asp Tyr Ala
        35                  40                  45

<210> SEQ ID NO 6
<211> LENGTH: 55
<212> TYPE: PRT
<213> ORGANISM: Homo sapiens

<400> SEQUENCE: 6

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55

<210> SEQ ID NO 7
<211> LENGTH: 28
<212> TYPE: PRT
<213> ORGANISM: Homo sapiens

<400> SEQUENCE: 7

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn
            20                  25

<210> SEQ ID NO 8
<211> LENGTH: 22
<212> TYPE: PRT
<213> ORGANISM: Artificial sequence
<220> FEATURE:
<223> OTHER INFORMATION: Homo sapiens

<400> SEQUENCE: 8

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 9
<211> LENGTH: 117
<212> TYPE: PRT
<213> ORGANISM: Homo sapiens

<400> SEQUENCE: 9

```
Thr Gly Thr Ile Glu Thr Thr Gly Asn Ile Ser Ala Glu Lys Gly Gly
1               5                   10                  15

Ser Ile Ile Leu Gln Cys His Leu Ser Ser Thr Thr Ala Gln Val Thr
            20                  25                  30

Gln Val Asn Trp Glu Gln Gln Asp Gln Leu Leu Ala Ile Cys Asn Ala
        35                  40                  45

Asp Leu Gly Trp His Ile Ser Pro Ser Phe Lys Asp Arg Val Ala Pro
    50                  55                  60

Gly Pro Gly Leu Gly Leu Thr Leu Gln Ser Leu Thr Val Asn Asp Thr
65                  70                  75                  80

Gly Glu Tyr Phe Cys Ile Tyr His Thr Tyr Pro Asp Gly Thr Tyr Thr
                85                  90                  95

Gly Arg Ile Phe Leu Glu Val Leu Glu Ser Ser Val Ala Glu His Gly
                100                 105                 110

Ala Arg Phe Gln Ile
            115
```

<210> SEQ ID NO 10
<211> LENGTH: 202
<212> TYPE: PRT
<213> ORGANISM: Artificial sequence
<220> FEATURE:
<223> OTHER INFORMATION: Homo sapiens

<400> SEQUENCE: 10

```
Thr Gly Thr Ile Glu Thr Thr Gly Asn Ile Ser Ala Glu Lys Gly Gly
1               5                   10                  15

Ser Ile Ile Leu Gln Cys His Leu Ser Ser Thr Thr Ala Gln Val Thr
            20                  25                  30

Gln Val Asn Trp Glu Gln Gln Asp Gln Leu Leu Ala Ile Cys Asn Ala
        35                  40                  45

Asp Leu Gly Trp His Ile Ser Pro Ser Phe Lys Asp Arg Val Ala Pro
    50                  55                  60

Gly Pro Gly Leu Gly Leu Thr Leu Gln Ser Leu Thr Val Asn Asp Thr
65                  70                  75                  80

Gly Glu Tyr Phe Cys Ile Tyr His Thr Tyr Pro Asp Gly Thr Tyr Thr
                85                  90                  95

Gly Arg Ile Phe Leu Glu Val Leu Glu Ser Ser Val Ala Glu His Gly
                100                 105                 110

Ala Arg Phe Gln Ile Ala Ser Phe Val Pro Val Phe Leu Pro Ala Lys
            115                 120                 125

Pro Thr Thr Thr Pro Ala Pro Arg Pro Pro Thr Pro Ala Pro Thr Ile
130                 135                 140

Ala Ser Gln Pro Leu Ser Leu Arg Pro Glu Ala Cys Arg Pro Ala Ala
145                 150                 155                 160

Gly Gly Ala Val His Thr Arg Gly Leu Asp Phe Ala Cys Asp Ile Tyr
                165                 170                 175

Ile Trp Ala Pro Leu Ala Gly Thr Cys Gly Val Leu Leu Leu Ser Leu
                180                 185                 190

Val Ile Thr Leu Tyr Cys Asn His Arg Asn
                195                 200
```

<210> SEQ ID NO 11
<211> LENGTH: 153
<212> TYPE: PRT
<213> ORGANISM: Artificial sequence
<220> FEATURE:

-continued

<223> OTHER INFORMATION: The sequence is synthesized

<400> SEQUENCE: 11

```
Gly Ala His Ala Asp Ile Thr Ser Glu Gln Lys Leu Ile Ser Glu Glu
1               5                   10                  15

Asp Leu Gly Gly Gly Gly Ser Gly Gly Gly Ser Glu Gln Lys Leu
            20                  25                  30

Ile Ser Glu Glu Asp Leu Gly Gly Gly Ser Gly Gly Gly Ser
        35                  40                  45

Glu Gln Lys Leu Ile Ser Glu Glu Asp Leu Gly Gly Gly Ser Gly
    50                  55                  60

Gly Gly Ser Ala Ser Phe Val Pro Val Phe Leu Pro Ala Lys Pro
65                  70                  75                  80

Thr Thr Thr Pro Ala Pro Arg Pro Pro Thr Pro Ala Pro Thr Ile Ala
                85                  90                  95

Ser Gln Pro Leu Ser Leu Arg Pro Glu Ala Cys Arg Pro Ala Ala Gly
                100                 105                 110

Gly Ala Val His Thr Arg Gly Leu Asp Phe Ala Cys Asp Ile Tyr Ile
            115                 120                 125

Trp Ala Pro Leu Ala Gly Thr Cys Gly Val Leu Leu Leu Ser Leu Val
    130                 135                 140

Ile Thr Leu Tyr Cys Asn His Arg Asn
145                 150
```

<210> SEQ ID NO 12
<211> LENGTH: 150
<212> TYPE: PRT
<213> ORGANISM: Artificial sequence
<220> FEATURE:
<223> OTHER INFORMATION: The sequence is synthesized

<400> SEQUENCE: 12

```
Gly Ala His Ala Asp Ile Thr Ser Tyr Pro Tyr Asp Val Pro Asp Tyr
1               5                   10                  15

Ala Gly Gly Gly Gly Ser Gly Gly Gly Ser Tyr Pro Tyr Asp Val
            20                  25                  30

Pro Asp Tyr Ala Gly Gly Gly Gly Ser Gly Gly Gly Ser Tyr Pro
        35                  40                  45

Tyr Asp Val Pro Asp Tyr Ala Gly Gly Gly Ser Gly Gly Gly Gly
    50                  55                  60

Ser Ala Ser Phe Val Pro Val Phe Leu Pro Ala Lys Pro Thr Thr Thr
65                  70                  75                  80

Pro Ala Pro Arg Pro Pro Thr Pro Ala Pro Thr Ile Ala Ser Gln Pro
                85                  90                  95

Leu Ser Leu Arg Pro Glu Ala Cys Arg Pro Ala Ala Gly Ala Val
                100                 105                 110

His Thr Arg Gly Leu Asp Phe Ala Cys Asp Ile Tyr Ile Trp Ala Pro
            115                 120                 125

Leu Ala Gly Thr Cys Gly Val Leu Leu Leu Ser Leu Val Ile Thr Leu
    130                 135                 140

Tyr Cys Asn His Arg Asn
145                 150
```

<210> SEQ ID NO 13
<211> LENGTH: 150
<212> TYPE: PRT
<213> ORGANISM: Artificial sequence

```
<220> FEATURE:
<223> OTHER INFORMATION: The sequence is synthesized

<400> SEQUENCE: 13

Gly Ala His Ala Asp Ile Thr Ser Asn Trp Ser His Pro Gln Phe Glu
1               5                   10                  15

Lys Gly Gly Gly Ser Gly Gly Gly Ser Asn Trp Ser His Pro
            20                  25                  30

Gln Phe Glu Lys Gly Gly Gly Ser Gly Gly Gly Ser Asn Trp
            35                  40                  45

Ser His Pro Gln Phe Glu Lys Gly Gly Gly Ser Gly Gly Gly
    50                  55                  60

Ser Ala Ser Phe Val Pro Val Phe Leu Pro Ala Lys Pro Thr Thr Thr
65              70                  75                  80

Pro Ala Pro Arg Pro Pro Thr Pro Ala Pro Thr Ile Ala Ser Gln Pro
                85                  90                  95

Leu Ser Leu Arg Pro Glu Ala Cys Arg Pro Ala Ala Gly Gly Ala Val
                100                 105                 110

His Thr Arg Gly Leu Asp Phe Ala Cys Asp Ile Tyr Ile Trp Ala Pro
            115                 120                 125

Leu Ala Gly Thr Cys Gly Val Leu Leu Leu Ser Leu Val Ile Thr Leu
    130                 135                 140

Tyr Cys Asn His Arg Asn
145             150

<210> SEQ ID NO 14
<211> LENGTH: 163
<212> TYPE: PRT
<213> ORGANISM: Artificial sequence
<220> FEATURE:
<223> OTHER INFORMATION: The sequence is synthesized

<400> SEQUENCE: 14

Gly Ala His Ala Ala Gln Leu Thr Leu Thr Lys Gly Asn Lys Glu Gln
1               5                   10                  15

Lys Leu Ile Ser Glu Glu Asp Leu Gly Glu Gln Lys Leu Ile Ser Glu
            20                  25                  30

Glu Asp Leu Gly Glu Gln Lys Leu Ile Ser Glu Glu Asp Leu Gly Gly
            35                  40                  45

Ser Tyr Pro Tyr Asp Val Pro Asp Tyr Ala Gly Pro Tyr Asp Val
    50                  55                  60

Pro Asp Tyr Ala Gly Tyr Pro Tyr Asp Val Pro Asp Tyr Ala Ala Ser
65              70                  75                  80

Phe Val Pro Val Phe Leu Pro Ala Lys Pro Thr Thr Thr Pro Ala Pro
                85                  90                  95

Arg Pro Pro Thr Pro Ala Pro Thr Ile Ala Ser Gln Pro Leu Ser Leu
                100                 105                 110

Arg Pro Glu Ala Cys Arg Pro Ala Ala Gly Gly Ala Val His Thr Arg
            115                 120                 125

Gly Leu Asp Phe Ala Cys Asp Ile Tyr Ile Trp Ala Pro Leu Ala Gly
    130                 135                 140

Thr Cys Gly Val Leu Leu Leu Ser Leu Val Ile Thr Leu Tyr Cys Asn
145                 150                 155                 160

His Arg Asn

<210> SEQ ID NO 15
```

<211> LENGTH: 250
<212> TYPE: PRT
<213> ORGANISM: Artificial sequence
<220> FEATURE:
<223> OTHER INFORMATION: The sequence is synthesized

<400> SEQUENCE: 15

Gly Ala His Ala Glu Gln Lys Leu Ile Ser Glu Glu Asp Leu Gly Glu
1               5                   10                  15

Gln Lys Leu Ile Ser Glu Glu Asp Leu Gly Gly Ser Tyr Pro Tyr Asp
            20                  25                  30

Val Pro Asp Tyr Ala Gly Tyr Pro Tyr Asp Val Pro Asp Tyr Ala Gly
        35                  40                  45

Thr Gly Thr Ile Glu Thr Thr Gly Asn Ile Ser Ala Glu Lys Gly Gly
    50                  55                  60

Ser Ile Ile Leu Gln Cys His Leu Ser Ser Thr Thr Ala Gln Val Thr
65                  70                  75                  80

Gln Val Asn Trp Glu Gln Gln Asp Gln Leu Leu Ala Ile Cys Asn Ala
                85                  90                  95

Asp Leu Gly Trp His Ile Ser Pro Ser Phe Lys Asp Arg Val Ala Pro
            100                 105                 110

Gly Pro Gly Leu Gly Leu Thr Leu Gln Ser Leu Thr Val Asn Asp Thr
        115                 120                 125

Gly Glu Tyr Phe Cys Ile Tyr His Thr Tyr Pro Asp Gly Thr Tyr Thr
    130                 135                 140

Gly Arg Ile Phe Leu Glu Val Leu Glu Ser Ser Val Ala Glu His Gly
145                 150                 155                 160

Ala Arg Phe Gln Ile Ala Ser Phe Val Pro Val Phe Leu Pro Ala Lys
                165                 170                 175

Pro Thr Thr Thr Pro Ala Pro Arg Pro Pro Thr Pro Ala Pro Thr Ile
            180                 185                 190

Ala Ser Gln Pro Leu Ser Leu Arg Pro Glu Ala Cys Arg Pro Ala Ala
        195                 200                 205

Gly Gly Ala Val His Thr Arg Gly Leu Asp Phe Ala Cys Asp Ile Tyr
    210                 215                 220

Ile Trp Ala Pro Leu Ala Gly Thr Cys Gly Val Leu Leu Leu Ser Leu
225                 230                 235                 240

Val Ile Thr Leu Tyr Cys Asn His Arg Asn
                245                 250

<210> SEQ ID NO 16
<211> LENGTH: 174
<212> TYPE: DNA
<213> ORGANISM: Artificial sequence
<220> FEATURE:
<223> OTHER INFORMATION: The sequence is synthesized

<400> SEQUENCE: 16
ggcgcgcatg ccgacattac tagtgagcag aagctcataa gcgaggaaga ccttgggggc      60
ggcggctctg aggggggcgg atcagagcag aaactgatta gcgaggagga tcttggaggc     120
ggtggttctg aggggggagg aagtgagcaa aaattgataa gtgaagagga tttg           174

<210> SEQ ID NO 17
<211> LENGTH: 165
<212> TYPE: DNA
<213> ORGANISM: Artificial sequence
<220> FEATURE:
<223> OTHER INFORMATION: The sequence is synthesized

<400> SEQUENCE: 17

```
ggcgcgcatg ccgacattac tagttaccct tatgatgtac cggattacgc tggaggcggc      60
gggtctggag gtgggggtag ttacccctac gacgttcccg actacgctgg tggcggcggg     120
tcaggaggtg gcgggtccta cccatacgat gtcccggact acgcc                      165
```

<210> SEQ ID NO 18
<211> LENGTH: 165
<212> TYPE: DNA
<213> ORGANISM: Artificial sequence
<220> FEATURE:
<223> OTHER INFORMATION: The sequence is synthesized

<400> SEQUENCE: 18

```
ggcgcgcatg ccgacattac tagtaactgg agccacccac aattcgagaa gggcggggggg    60
ggaagtggag gcggcggtag taattggtct cacccacaat ttgagaaagg gggcgggggc    120
tctggagggg gagggagtaa ttggagccac ccccaatttg aaaag                    165
```

<210> SEQ ID NO 19
<211> LENGTH: 234
<212> TYPE: DNA
<213> ORGANISM: Artificial sequence
<220> FEATURE:
<223> OTHER INFORMATION: The sequence is synthesized

<400> SEQUENCE: 19

```
ggcgcgcatg ccgctcagtt gacattgacg aagggcaata agaacagaa gcttattagt     60
gaagaggact tgggagagca gaagcttata tccgaggagg accttggcga gcaaaaattg   120
atttcagagg aagatttggg tgggagttac ccctacgacg tccctgatta cgctggctat   180
ccatacgatg taccagacta tgcaggttac ccctatgacg tacctgatta tgcg          234
```

<210> SEQ ID NO 20
<211> LENGTH: 141
<212> TYPE: DNA
<213> ORGANISM: Artificial sequence
<220> FEATURE:
<223> OTHER INFORMATION: The sequence is synthesized

<400> SEQUENCE: 20

```
ggcgcgcatg ccgagcagaa gcttatatcc gaggaggacc ttggcgagca aaaattgatt    60
tcagaggaag atttgggtgg gagttacccc tacgacgtcc ctgattacgc tggctatcca   120
tacgatgtac cagactatgc a                                              141
```

<210> SEQ ID NO 21
<211> LENGTH: 84
<212> TYPE: DNA
<213> ORGANISM: Homo sapiens

<400> SEQUENCE: 21

```
atctacatct gggcgccctt ggccgggact tgtgggtcc ttctcctgtc actggttatc     60
acccttact gcaaccacag gaac                                            84
```

<210> SEQ ID NO 22
<211> LENGTH: 165
<212> TYPE: DNA
<213> ORGANISM: Homo sapiens

<400> SEQUENCE: 22
ttcgtgccgg tcttcctgcc agcgaagccc accacgacgc cagcgccgcg accaccaaca    60
ccggcgccca ccatcgcgtc gcagcccctg tccctgcgcc cagaggcgtg ccggccagcg    120
gcggggggcg cagtgcacac gagggggctg gacttcgcct gtgat    165

<210> SEQ ID NO 23
<211> LENGTH: 66
<212> TYPE: DNA
<213> ORGANISM: Artificial sequence
<220> FEATURE:
<223> OTHER INFORMATION: Homo sapiens

<400> SEQUENCE: 23
atgcttctcc tggtgacaag ccttctgctc tgtgagttac cacacccagc attcctcctg    60
atccca    66

<210> SEQ ID NO 24
<211> LENGTH: 351
<212> TYPE: DNA
<213> ORGANISM: Homo sapiens

<400> SEQUENCE: 24
acaggcacaa tagaaacaac ggggaacatt tctgcagaga aaggtggctc tatcatctta    60
caatgtcacc tctcctccac cacggcacaa gtgacccagg tcaactggga gcagcaggac    120
cagcttctgg ccatttgtaa tgctgacttg gggtggcaca tctccccatc cttcaaggat    180
cgagtggccc caggtcccgg cctgggcctc accctccagt cgctgaccgt gaacgataca    240
ggggagtact tctgcatcta tcacacctac cctgatggga cgtacactgg gagaatcttc    300
ctggaggtcc tagaaagctc agtggctgag cacggtgcca ggttccagat t    351

<210> SEQ ID NO 25
<211> LENGTH: 606
<212> TYPE: DNA
<213> ORGANISM: Artificial sequence
<220> FEATURE:
<223> OTHER INFORMATION: Homo sapiens

<400> SEQUENCE: 25
acaggcacaa tagaaacaac ggggaacatt tctgcagaga aaggtggctc tatcatctta    60
caatgtcacc tctcctccac cacggcacaa gtgacccagg tcaactggga gcagcaggac    120
cagcttctgg ccatttgtaa tgctgacttg gggtggcaca tctccccatc cttcaaggat    180
cgagtggccc caggtcccgg cctgggcctc accctccagt cgctgaccgt gaacgataca    240
ggggagtact tctgcatcta tcacacctac cctgatggga cgtacactgg gagaatcttc    300
ctggaggtcc tagaaagctc agtggctgag cacggtgcca ggttccagat tgctagcttc    360
gtgccggtct tcctgccagc gaagcccacc acgacgccag cgccgcgacc accaacaccg    420 cgcccacca tcgcgtcgca gcccctgtcc ctgcgcccag aggcgtgccg gccagcggcg    480
gggggcgcag tgcacacgag ggggctggac ttcgcctgtg atatctacat ctgggcgccc    540
ttggccggga cttgtggggt ccttctcctg tcactggtta tcacccttta ctgcaaccac    600
aggaac    606

<210> SEQ ID NO 26
<211> LENGTH: 528
<212> TYPE: DNA
<213> ORGANISM: Artificial sequence
<220> FEATURE:
<223> OTHER INFORMATION: The sequence is synthesized

<400> SEQUENCE: 26

```
atgcttctcc tggtgacaag ccttctgctc tgtgagttac cacacccagc attcctcctg      60
atcccaggcg cgcatgccga cattactagt gagcagaagc tcataagcga ggaagacctt     120
gggggcggcg gctctggagg gggcggatca gagcagaaac tgattagcga ggaggatctt     180
ggaggcggtg gttctggagg gggaggaagt gagcaaaaat tgataagtga agaggatttg     240
ggaggtggag gttcagggggg aggcggtagt gctagcttcg tgccggtctt cctgccagcg     300
aagcccacca cgacgccagc gccgcgacca ccaacaccgg cgcccaccat cgcgtcgcag     360
cccctgtccc tgcgcccaga ggcgtgccgg ccagcggcgg ggggcgcagt gcacacgagg     420
gggctggact tcgcctgtga tatctacatc tgggcgccct tggccgggac ttgtggggtc     480
cttctcctgt cactggttat cacccttta ctgcaaccaca ggaactga                   528
```

<210> SEQ ID NO 27
<211> LENGTH: 519
<212> TYPE: DNA
<213> ORGANISM: Artificial sequence
<220> FEATURE:
<223> OTHER INFORMATION: The sequence is synthesized

<400> SEQUENCE: 27

```
atgcttctcc tggtgacaag ccttctgctc tgtgagttac cacacccagc attcctcctg      60
atcccaggcg cgcatgccga cattactagt taccccttatg atgtaccgga ttacgctgga    120
ggcggcgggt ctggaggtgg gggtagttac ccctacgacg ttcccgacta cgctggtggc     180
ggcgggtcag gaggtggcgg gtcctaccca tacgatgtcc cggactacgc cggggggcggt    240
ggaagtggag gaggtggctc cgctagcttc gtgccggtct tcctgccagc gaagcccacc     300
acgacgccag cgccgcgacc accaacaccg cgcccacca tcgcgtcgca gcccctgtcc      360
ctgcgcccag aggcgtgccg gccagcggcg ggggcgcag tgcacacgag ggggctggac      420
ttcgcctgtg atatctacat ctgggcgccc ttggccggga cttgtggggt ccttctcctg     480
tcactggtta tcacccttta ctgcaaccac aggaactga                            519
```

<210> SEQ ID NO 28
<211> LENGTH: 519
<212> TYPE: DNA
<213> ORGANISM: Artificial sequence
<220> FEATURE:
<223> OTHER INFORMATION: The sequence is synthesized

<400> SEQUENCE: 28

```
atgcttctcc tggtgacaag ccttctgctc tgtgagttac cacacccagc attcctcctg      60
atcccaggcg cgcatgccga cattactagt aactggagcc acccacaatt cgagaagggc    120
ggggggggaa gtggaggcgg cggtagtaat tggtctcacc cacaatttga aaagggggc      180
gggggctctg gaggggagg gagtaattgg agccacccccc aatttgaaaa ggggcgggggg    240
ggatctgggg ggggtgggtc tgctagcttc gtgccggtct tcctgccagc gaagcccacc     300
acgacgccag cgccgcgacc accaacaccg cgcccacca tcgcgtcgca gcccctgtcc      360
ctgcgcccag aggcgtgccg gccagcggcg ggggcgcag tgcacacgag ggggctggac      420
ttcgcctgtg atatctacat ctgggcgccc ttggccggga cttgtggggt ccttctcctg     480
tcactggtta tcacccttta ctgcaaccac aggaactga                            519
```

<210> SEQ ID NO 29

<211> LENGTH: 558
<212> TYPE: DNA
<213> ORGANISM: Artificial sequence
<220> FEATURE:
<223> OTHER INFORMATION: The sequence is synthesized

<400> SEQUENCE: 29

```
atgcttctcc tggtgacaag ccttctgctc tgtgagttac cacacccagc attcctcctg      60
atcccaggcg cgcatgccgc tcagttgaca ttgacgaagg gcaataaaga acagaagctt     120
attagtgaag aggacttggg agagcagaag cttatatccg aggaggacct tggcgagcaa     180
aaattgattt cagaggaaga tttgggtggg agttacccct acgacgtccc tgattacgct     240
ggctatccat acgatgtacc agactatgca ggttacccct atgacgtacc tgattatgcg     300
gctagcttcg tgccggtctt cctgccagca agcccacca cgacgccagc gccgcgacca     360
ccaacaccgg cgcccaccat cgcgtcgcag cccctgtccc tgcgcccaga ggcgtgccgg     420
ccagcggcgg ggggcgcagt gcacacgagg gggctggact tcgcctgtga tatctacatc     480
tgggcgccct tggccgggac ttgtggggtc cttctcctgt cactggttat cacccttta      540
tgcaaccaca ggaactga                                                   558
```

<210> SEQ ID NO 30
<211> LENGTH: 819
<212> TYPE: DNA
<213> ORGANISM: Artificial sequence
<220> FEATURE:
<223> OTHER INFORMATION: The sequence is synthesized

<400> SEQUENCE: 30

```
atgcttctcc tggtgacaag ccttctgctc tgtgagttac cacacccagc attcctcctg      60
atcccaggcg cgcatgccga gcagaagctt atatccgagg aggaccttgg cgagcaaaaa     120
ttgatttcag aggaagattt gggtgggagt taccccctacg acgtccctga ttacgctggc    180
tatccatacg atgtaccaga ctatgcaggt acaggcacaa tagaaacaac ggggaacatt     240
tctgcagaga aggtggctc tatcatctta caatgtcacc tctcctccac cacggcacaa      300
gtgacccagg tcaactggga gcagcaggac cagcttctgg ccatttgtaa tgctgacttg     360
gggtggcaca tctccccatc cttcaaggat cgagtggccc caggtcccgg cctgggcctc     420
accctccagt cgctgaccgt gaacgataca ggggagtact tctgcatcta tcacacctac     480
cctgatggga cgtacactgg gagaatcttc ctggaggtcc tagaaagctc agtggctgag     540
cacggtgcca ggttccagat tgctagcttc gtgccggtct tcctgccagc gaagcccacc     600
acgacgccag cgccgcgacc accaacaccg gcgcccacca tcgcgtcgca gcccctgtcc     660
ctgcgcccag aggcgtgccg gccagcggcg gggggcgcag tgcacacgag ggggctggac     720
ttcgcctgtg atatctacat ctgggcgccc ttggccggga cttgtgggt ccttctcctg      780
tcactggtta tcaccctta ctgcaaccac aggaactga                             819
```

<210> SEQ ID NO 31
<211> LENGTH: 23
<212> TYPE: DNA
<213> ORGANISM: Artificial sequence
<220> FEATURE:
<223> OTHER INFORMATION: Vaccinia virus

<400> SEQUENCE: 31

```
taacgataat agatacggaa cgg                                              23
```

<210> SEQ ID NO 32
<211> LENGTH: 23
<212> TYPE: DNA
<213> ORGANISM: Artificial sequence
<220> FEATURE:
<223> OTHER INFORMATION: Vaccinia virus

<400> SEQUENCE: 32
gtgtatgaaa tgctttaagg agg                                            23

<210> SEQ ID NO 33
<211> LENGTH: 480
<212> TYPE: DNA
<213> ORGANISM: Artificial sequence
<220> FEATURE:
<223> OTHER INFORMATION: Vaccinia virus

<400> SEQUENCE: 33
ctttctgtta ttattattga tccaatcaaa aaataaatta gaagccgtgg gtcattgtta    60
tgaatctctt tcagaggaat acagacaatt gacaaaattc acagactttc aagattttaa   120
aaaactgttt aacaaggtcc ctattgttac agatggaagg gtcaaactta ataaggata    180 tttgttcgac tttgtgatta gtttgatgcg attcaaaaaa gaatcctctc tagctaccac   240
cgcaatagat cctgttagat acatagatcc tcgtcgcaat atcgcatttt ctaacgtgat   300
ggatatatta aagtcgaata aagtgaacaa taattaattc tttattgtca tcatgaacgg   360
cggacatatt cagttgataa tcggccccat gttttcaggt aaaagtacag aattaattag   420
acgagttaga cgttatcaaa tagctcaata taaatgcgtg actataaaat attctaacga   480

<210> SEQ ID NO 34
<211> LENGTH: 520
<212> TYPE: DNA
<213> ORGANISM: Artificial sequence
<220> FEATURE:
<223> OTHER INFORMATION: Vaccinia virus

<400> SEQUENCE: 34 tcctttteta aacgattggg tgaggaaacc gagatagaaa taataggagg taatgatatg 60
tatcaatcgg tgtgtagaaa gtgttacatc gactcataat attatatttt ttatctaaaa 120
aactaaaaat aaacattgat taaattttaa tataatactt aaaaatggat gttgtgtcgt 180
tagataaacc gtttatgtat tttgaggaaa ttgataatga gttagattac gaaccagaaa 240
gtgcaaatga ggtcgcaaaa aaactgccgt atcaaggaca gttaaaacta ttactaggag 300
aattattttt tcttagtaag ttacagcgac acggtatatt agatggtgcc accgtagtgt 360
atataggatc tgctcccggt acacatatac gttatttgag agatcatttc tataatttag 420
gagtgatcat caaatggatg ctaattgacg gccgccatca tgatcctatt ttaaatggat 480
tgcgtgatgt gactctagtg actcggttcg ttgatgagga 520

<210> SEQ ID NO 35
<211> LENGTH: 1323
<212> TYPE: DNA
<213> ORGANISM: Artificial sequence
<220> FEATURE:
<223> OTHER INFORMATION: The sequence is synthesized

<400> SEQUENCE: 35
atgaccgaat acaaacctac agtaagactg gctacgcgag acgacgtacc cagagcggtt 60
cggacgttgg cagccgcctt tgcagattac cctgcgacac ggcatactgt cgatcctgat 120

-continued

```
cgacatatag aacgagtgac cgagttgcaa gagttgtttt tgacccgcgt cggtcttgat    180
attgggaagg tatgggtcgc agacgacggc gccgcggtgg cggtctggac cacgccggag    240
agcgtcgaag cgggggcggt gttcgccgag atcggcccgc gcatggccga gttgagcggt    300
tcccggctgg ccgcgcagca acagatggaa ggcctcctgg cgccgcaccg gcccaaggag    360
cccgcgtggt tcctggccac cgtcggcgtc tcgcccgacc accagggcaa gggtctgggc    420
agcgccgtcg tgctccccgg agtggaggcg gccgagcgcg ccggggtgcc cgccttcctg    480
gagacctccg cgccccgcaa cctccccttc tacgagcggc tcggcttcac cgtcaccgcc    540
gacgtcgagg tgcccgaagg accgcgcacc tggtgcatga cccgcaagcc cggtgccact    600
agcatggtga gcaagggcga ggagctgttc accggggtgg tgcccatcct ggtcgagctg    660
gacggcgacg taaacggcca caagttcagc gtgtccggcg agggcgaggg cgatgccacc    720
tacggcaagc tgaccctgaa gttcatctgc accaccggca agctgcccgt gccctggccc    780
accctcgtga ccaccctgac ctacggcgtg cagtgcttca gccgctaccc cgaccacatg    840
aagcagcacg acttcttcaa gtccgccatg cccgaaggct acgtccagga gcgcaccatc    900
ttcttcaagg acgacggcaa ctacaagacc cgcgccgagg tgaagttcga gggcgacacc    960
ctggtgaacc gcatcgagct gaagggcatc gacttcaagg aggacggcaa catcctgggg   1020
cacaagctgg agtacaacta caacagccac aacgtctata tcatggccga caagcagaag   1080
aacggcatca aggtgaactt caagatccgc cacaacatcg aggacggcag cgtgcagctc   1140
gccgaccact accagcagaa cacccccatc ggcgacggcc ccgtgctgct gcccgacaac   1200
cactacctga gcacccagtc cgccctgagc aaagacccca acgagaagcg cgatcacatg   1260
gtcctgctgg agttcgtgac cgccgccggg atcactctcg gcatggacga gctgtacaag   1320
taa                                                                 1323
```

<210> SEQ ID NO 36
<211> LENGTH: 129
<212> TYPE: DNA
<213> ORGANISM: Artificial sequence
<220> FEATURE:
<223> OTHER INFORMATION: Vaccinia virus

<400> SEQUENCE: 36

```
cactaattcc aaacccaccc gctttttata gtaagttttt cacccataaa taataaatac     60
aataattaat ttctcgtaaa agtagaaaat atattctaat ttattgcacg gtaaggaagt    120
agatcataa                                                           129
```

<210> SEQ ID NO 37
<211> LENGTH: 40
<212> TYPE: DNA
<213> ORGANISM: Artificial sequence
<220> FEATURE:
<223> OTHER INFORMATION: Vaccinia virus

<400> SEQUENCE: 37

```
aaaaattgaa attttatttt ttttttttgg aatataaata                          40
```

<210> SEQ ID NO 38
<211> LENGTH: 5632
<212> TYPE: DNA
<213> ORGANISM: Artificial sequence
<220> FEATURE:
<223> OTHER INFORMATION: The sequence is synthesized

<400> SEQUENCE: 38

```
gacgcgccct gtagcggcgc attaagcgcg gcgggtgtgg tggttacgcg cagcgtgacc      60
gctacacttg ccagcgccct agcgcccgct cctttcgctt tcttcccttc ctttctcgcc     120
acgttcgccg gctttccccg tcaagctcta aatcggggc tccctttagg gttccgattt      180
agtgctttac ggcacctcga ccccaaaaaa cttgattagg gtgatggttc acgtagtggg     240
ccatcgccct gatagacggt ttttcgccct ttgacgttgg agtccacgtt ctttaatagt     300
ggactcttgt tccaaactgg aacaacactc aaccctatct cggtctattc ttttgattta    360
taagggattt tgccgatttc ggcctattgg ttaaaaaatg agctgattta caaaaatt     420 aacgcgaatt ttaacaaaat attaacgttt acaatttcag gtggcacttt tcggggaaat    480
gtgcgcggaa ccctatttg tttattttc taaatacatt caaatatgta tccgctcatg      540
agacaataac cctgataaat gcttcaataa tattgaaaaa ggaagagtat gagtattcaa     600
catttccgtg tcgcccttat tcccttttt gcggcatttt gccttcctgt ttttgctcac     660
ccagaaacgc tggtgaaagt aaaagatgct gaagatcagt tgggtgcacg agtgggttac     720
atcgaactgg atctcaacag cggtaagatc cttgagagtt ttcgccccga gaacgttttt     780
ccaatgatga gcacttttaa agttctgcta tgtggcgcgg tattatcccg tattgacgcc     840
gggcaagagc aactcggtcg ccgcatacac tattctcaga atgacttggt tgagtactca     900
ccagtcacag aaaagcatct tacggatggc atgacagtaa gagaattatg cagtgctgcc     960
ataaccatga gtgataacac tgcggccaac ttacttctga caacgatcgg aggaccgaag    1020
gagctaaccg cttttttgca acatgggg gatcatgtaa ctcgccttga tcgttgggaa     1080
ccggagctga atgaagccat accaaacgac gagcgtgaca ccacgatgcc tgtagcaatg    1140
gcaacaacgt tgcgcaaact attaactggc gaactactta ctctagcttc ccggcaacaa    1200
ttaatagact ggatggaggc ggataaagtt gcaggaccac ttctgcgctc ggcccttccg    1260
gctggctggt ttattgctga taaatctgga gccggtgagc gtgggtctcg cggtatcatt    1320
gcagcactgg ggccagatgg taagccctcc cgtatcgtag ttatctacac gacggggagt    1380
caggcaacta tggatgaacg aaatagacag atcgctgaga taggtgcctc actgattaag    1440
cattggtaac tgtcagacca agtttactca tatatacttt agattgattt aaaacttcat    1500
ttttaattta aaaggatcta ggtgaagatc ctttttgata atctcatgac caaaatccct    1560
taacgtgagt tttcgttcca ctgagcgtca gaccccgtag aaaagatcaa aggatcttct    1620
tgagatcctt ttttctgcg cgtaatctgc tgcttgcaaa caaaaaaacc accgctacca    1680
gcggtggttt gtttgccgga tcaagagcta ccaactcttt ttccgaaggt aactggcttc    1740
agcagagcgc agataccaaa tactgtcctt ctagtgtagc cgtagttagg ccaccacttc    1800
aagaactctg tagcaccgcc tacatacctc gctctgctaa cctgttacc agtggctgct    1860 gccagtggcg ataagtcgtg tcttaccggg ttggactcaa gacgatagtt accggataag    1920
gcgcagcggt cgggctgaac ggggggttcg tgcacacagc ccagcttgga gcgaacgacc    1980
tacaccgaac tgagatacct acagcgtgag cattgagaaa gcgccacgct tcccgaaggg    2040
agaaaggcgg acaggtatcc ggtaagcggc agggtcggaa caggagagcg cacgagggag    2100
cttccagggg gaaacgcctg gtatctttat agtcctgtcg ggtttcgcca cctctgactt    2160
gagcgtcgat ttttgtgatg ctcgtcaggg gggcggagcc tatggaaaaa cgccagcaac    2220
gcggcctttt tacggttcct ggccttttgc tggccttttg ctcacatgtt ctttcctgcg    2280
ttatcccctg attctgtgga taaccgtatt accgcctttg agtgagctga taccgctcgc    2340
```

```
cgcagccgaa cgaccgagcg cagcgagtca gtgagcgagg aaggaattct aacgataata    2400
gatacggaac ggctttctgt tattattatt gatccaatca aaaataaat tagaagccgt    2460 gggtcattgt tatgaatctc tttcagagga atacagacaa ttgacaaaat tcacagactt    2520
tcaagatttt aaaaaactgt ttaacaaggt ccctattgtt acagatggaa gggtcaaact    2580
taataaagga tatttgttcg actttgtgat tagtttgatg cgattcaaaa aagaatcctc    2640
tctagctacc accgcaatag atcctgttag atacatagat cctcgtcgca atatcgcatt    2700
ttctaacgtg atggatatat taaagtcgaa taaagtgaac aataattaat tctttattgt    2760
catcatgaac ggcggacata ttcagttgat aatcggcccc atgttttcag gtaaaagtac    2820
agaattaatt agacgagtta gacgttatca aatagctcaa tataaatgcg tgactataaa    2880
atattctaac gattttatc catcaggtga tctgttttta ttgtggagtt gtcgacttag    2940
ttcctgtggt tgcagtaaag ggtgataacc agtgacagga aaggacccc acaagtcccg    3000 gccaagggcg cccagatgta gatatcacag gcgaagtcca gccccctcgt gtgcactgcg    3060 cccccgccg ctggccggca cgcctctggg cgcaggaca ggggctgcga cgcgatggtg    3120
ggcgccggtg ttggtggtcg cggcgctggc gtcgtggtgg gcttcgctgg caggaagacc    3180
ggcacgaagc tagcagaccc acccccccca gatccccccc cgccctttc aaattggggg    3240 tggctccaat tactccctcc ccctccagag ccccgcccc ctttctcaaa ttgtgggtga    3300
gaccaattac taccgccgcc tccacttccc ccccgcccct tctcgaattg tgggtggctc    3360
cagttactag taatgtcggc atgcgcgcct gggatcagga ggaatgctgg gtgtggtaac    3420
tcacagagca gaaggcttgt caccaggaga agcataccgg tttcgagctt atttatattc    3480
caaaaaaaaa aaataaaatt tcaatttttg gatccataac ttcgtatagc atacattata    3540
cgaagttatc actaattcca aacccacccg ctttttatag taagttttc acccataaat    3600 aataaataca ataattaatt tctcgtaaaa gtagaaaata tattctaatt tattgcacgg    3660
taaggaagta gatcataaaa gcttatgacc gaatacaaac ctacagtaag actggctacg    3720
cgagacgacg tacccagagc ggttcggacg ttggcagccg cctttgcaga ttaccctgcg    3780
acacggcata ctgtcgatcc tgatcgacat atagaacgag tgaccgagtt gcaagagttg    3840
tttttgaccc gcgtcggtct tgatattggg aaggtatggg tcgcagacga cggcgccgcg    3900
gtggcggtct ggaccacgcc ggagagcgtc gaagcggggg cggtgttcgc cgagatcggc    3960
ccgcgcatgg ccgagttgag cggttccgg ctggccgcgc agcaacagat ggaaggcctc    4020
ctggcgccgc accggcccaa ggagcccgcg tggttcctgg ccaccgtcgg cgtctcgccc    4080
gaccaccagg gcaagggtct gggcagcgcc gtcgtgctcc ccggagtgga ggcggccgag    4140
cgcgccgggg tgcccgcctt cctggagacc tccgcgcccc gcaacctccc cttctacgag    4200
cggctcggct tcaccgtcac cgccgacgtc gaggtgcccg aaggaccgcg cacctggtgc    4260
atgacccgca agcccggtgc cactagcatg gtgagcaagg gcgaggagct gttcaccggg    4320
gtggtgccca tcctggtcga gctggacggc gacgtaaacg gccacaagtt cagcgtgtcc    4380
ggcgagggcg agggcgatgc cacctacggc aagctgaccc tgaagttcat ctgcaccacc    4440
ggcaagctgc ccgtgccctg gcccaccctc gtgaccaccc tgacctacgg cgtgcagtgc    4500
ttcagccgct accccgacca catgaagcag cacgacttct tcaagtccgc catgcccgaa    4560
ggctacgtcc aggagcgcac catcttcttc aaggacgacg gcaactacaa gacccgcgcc    4620
gaggtgaagt tcgagggcga caccctggtg aaccgcatcg agctgaaggg catcgacttc    4680
aaggaggacg gcaacatcct ggggcacaag ctggagtaca actacaacag ccacaacgtc    4740
```

```
tatatcatgg ccgacaagca gaagaacggc atcaaggtga acttcaagat ccgccacaac    4800
atcgaggacg gcagcgtgca gctcgccgac cactaccagc agaacacccc catcggcgac    4860
ggccccgtgc tgctgcccga caaccactac ctgagcaccc agtccgccct gagcaaagac    4920
cccaacgaga agcgcgatca catggtcctg ctggagttcg tgaccgccgc cgggatcact    4980
ctcggcatgg acgagctgta caagtaaata acttcgtata gcatacatta tacgaagtta    5040
tggtacccct tccttttcta acgattgggt gaggaaaccg agatagaaat aataggaggt    5100
aatgatatgt atcaatcggt gtgtagaaag tgttacatcg actcataata ttatattttt    5160
tatctaaaaa actaaaaata aacattgatt aaatttttaat ataatactta aaaatggatg    5220
ttgtgtcgtt agataaaccg tttatgtatt ttgaggaaat tgataatgag ttagattacg    5280
aaccagaaag tgcaaatgag gtcgcaaaaa aactgccgta tcaaggacag ttaaaactat    5340
tactaggaga attattttt cttagtaagt tacagcgaca cggtatatta gatggtgcca    5400
ccgtagtgta tataggatct gctcccggta cacatatacg ttatttgaga gatcatttct    5460
ataatttagg agtgatcatc aaatggatgc taattgacgg ccgccatcat gatcctattt    5520
taaatggatt gcgtgatgtg actctagtga ctcggttcgt tgatgaggag tgtatgaaat    5580
gctttaagga ggatcgatat caacgcttat ttgcagcctg aatggcgaat gg            5632
```

```
<210> SEQ ID NO 39
<211> LENGTH: 18
<212> TYPE: PRT
<213> ORGANISM: Artificial sequence
<220> FEATURE:
<223> OTHER INFORMATION: The sequence is synthesized

<400> SEQUENCE: 39

Gly Ser Thr Ser Gly Ser Gly Lys Pro Gly Ser Gly Glu Gly Ser Thr
1               5                   10                  15

Lys Gly

<210> SEQ ID NO 40
<211> LENGTH: 15
<212> TYPE: PRT
<213> ORGANISM: Artificial sequence
<220> FEATURE:
<223> OTHER INFORMATION: The sequence is synthesized

<400> SEQUENCE: 40

Gly Gly Gly Gly Ser Gly Gly Gly Ser Gly Gly Gly Gly Ser
1               5                   10                  15

<210> SEQ ID NO 41
<211> LENGTH: 18
<212> TYPE: PRT
<213> ORGANISM: Artificial sequence
<220> FEATURE:
<223> OTHER INFORMATION: The sequence is synthesized

<400> SEQUENCE: 41

Gly Ser Thr Ser Gly Ser Gly Lys Pro Gly Ser Gly Glu Gly Ser Thr
1               5                   10                  15

Lys Gly

<210> SEQ ID NO 42
<211> LENGTH: 260
<212> TYPE: PRT
<213> ORGANISM: Artificial sequence
```

<220> FEATURE:
<223> OTHER INFORMATION: The sequence is synthesized

<400> SEQUENCE: 42

Gly Ala His Ala Asp Ile Val Leu Thr Gln Ser Pro Ala Phe Leu Ala
1               5                   10                  15

Val Ser Leu Gly Gln Arg Ala Thr Ile Ser Cys Arg Ala Ser Glu Ser
            20                  25                  30

Val Asp Asn Tyr Gly Phe Ser Phe Met Asn Trp Phe Gln Gln Lys Pro
        35                  40                  45

Gly Gln Pro Pro Lys Leu Leu Ile Tyr Ala Ile Ser Asn Arg Gly Ser
    50                  55                  60

Gly Val Pro Ala Arg Phe Ser Gly Ser Gly Ser Gly Thr Asp Phe Ser
65                  70                  75                  80

Leu Asn Ile His Pro Val Glu Glu Asp Asp Pro Ala Met Tyr Phe Cys
                85                  90                  95

Gln Gln Thr Lys Glu Val Pro Trp Thr Phe Gly Gly Gly Thr Lys Leu
            100                 105                 110

Glu Ile Lys Gly Ser Thr Ser Gly Ser Gly Lys Pro Gly Ser Gly Glu
        115                 120                 125

Gly Ser Thr Lys Gly Gln Val Gln Leu Gln Glu Ser Gly Gly Asp Leu
    130                 135                 140

Val Lys Pro Gly Gly Ser Leu Lys Leu Ser Cys Ala Ala Ser Gly Phe
145                 150                 155                 160

Thr Phe Ser His Tyr Gly Met Ser Trp Val Arg Gln Thr Pro Asp Lys
                165                 170                 175

Arg Leu Glu Trp Val Ala Thr Ile Gly Ser Arg Gly Thr Tyr Thr His
            180                 185                 190

Tyr Pro Asp Ser Val Lys Gly Arg Phe Thr Ile Ser Arg Asp Asn Asp
        195                 200                 205

Lys Asn Ala Leu Tyr Leu Gln Met Asn Ser Leu Lys Ser Glu Asp Thr
    210                 215                 220

Ala Met Tyr Tyr Cys Ala Arg Arg Ser Glu Phe Tyr Tyr Gly Asn
225                 230                 235                 240

Thr Tyr Tyr Tyr Ser Ala Met Asp Tyr Trp Gly Gln Gly Ala Ser Val
                245                 250                 255

Thr Val Ser Ser
            260

<210> SEQ ID NO 43
<211> LENGTH: 252
<212> TYPE: PRT
<213> ORGANISM: Artificial sequence
<220> FEATURE:
<223> OTHER INFORMATION: The sequence is synthesized

<400> SEQUENCE: 43

Gly Ala His Ala Glu Val Lys Leu Val Glu Ser Gly Gly Asp Leu Val
1               5                   10                  15

Lys Pro Gly Gly Ser Leu Lys Leu Ser Cys Ala Ala Ser Gly Phe Thr
            20                  25                  30

Phe Ser Ser Tyr Gly Met Ser Trp Val Arg Gln Thr Pro Asp Lys Arg
        35                  40                  45

Leu Glu Trp Val Ala Thr Ile Ser Arg Gly Gly Ser Tyr Thr Tyr Tyr
    50                  55                  60

Pro Asp Ser Val Lys Gly Arg Phe Thr Ile Ser Arg Asp Asn Ala Lys

```
                65                  70                  75                  80
Asn Thr Leu Tyr Leu Gln Met Ser Ser Leu Lys Ser Glu Asp Thr Ala
                    85                  90                  95

Met Tyr Tyr Cys Ala Arg Arg Glu Thr Tyr Asp Glu Lys Gly Phe Ala
                100                 105                 110

Tyr Trp Gly Gln Gly Thr Thr Val Thr Val Ser Ser Gly Gly Gly Gly
                115                 120                 125

Ser Gly Gly Gly Gly Ser Gly Gly Gly Ser Asp Ile Glu Leu Thr
            130                 135                 140

Gln Ser Pro Ser Ser Leu Thr Val Thr Ala Gly Glu Lys Val Thr Met
145                 150                 155                 160

Ser Cys Lys Ser Ser Gln Ser Leu Leu Asn Ser Gly Asn Gln Lys Asn
                165                 170                 175

Tyr Leu Thr Trp Tyr Gln Gln Lys Pro Gly Gln Pro Pro Lys Leu Leu
                180                 185                 190

Ile Tyr Trp Ala Ser Thr Arg Glu Ser Gly Val Pro Asp Arg Phe Thr
                195                 200                 205

Gly Ser Gly Ser Gly Arg Asp Phe Thr Leu Thr Ile Ser Ser Val Gln
            210                 215                 220

Ala Glu Asp Leu Ala Val Tyr Tyr Cys Gln Asn Asp Asn Ser His Pro
225                 230                 235                 240

Leu Thr Phe Gly Ala Gly Thr Lys Leu Glu Leu Lys
                245                 250

<210> SEQ ID NO 44
<211> LENGTH: 253
<212> TYPE: PRT
<213> ORGANISM: Artificial sequence
<220> FEATURE:
<223> OTHER INFORMATION: The sequence is synthesized

<400> SEQUENCE: 44

Gly Ala His Ala Glu Leu Val Met Thr Gln Ser Pro Ala Ser Leu Ala
1               5                   10                  15

Val Ser Leu Gly Gln Arg Ala Thr Ile Ser Cys Arg Ala Ser Glu Ser
                20                  25                  30

Val Asp Ser Tyr Gly Lys Ser Phe Met His Trp Tyr Gln Leu Lys Pro
            35                  40                  45

Gly Gln Pro Pro Lys Leu Leu Ile Tyr Arg Ala Ser Asn Leu Glu Ser
        50                  55                  60

Gly Val Pro Ala Arg Phe Ser Gly Ser Gly Ser Arg Thr Asp Phe Thr
65                  70                  75                  80

Leu Thr Ile Asp Pro Val Glu Ala Asp Ala Ala Thr Tyr Tyr Cys
                85                  90                  95

Gln Gln Asn Asn Glu Asp Pro Trp Thr Phe Gly Gly Gly Thr Lys Leu
                100                 105                 110

Glu Ile Lys Gly Ser Thr Ser Gly Ser Gly Lys Pro Gly Ser Gly Glu
                115                 120                 125

Gly Ser Thr Lys Gly Glu Val Gln Leu Glu Gln Ser Gly Pro Glu Leu
            130                 135                 140

Val Lys Pro Gly Ala Ser Val Lys Met Ser Cys Lys Ala Ser Gly Tyr
145                 150                 155                 160

Thr Phe Thr Asn Tyr Tyr Met Lys Trp Val Lys Gln Ser His Gly Lys
                165                 170                 175

Ser Leu Glu Trp Ile Gly Asp Leu Asn Pro Asn Asn Gly Asp Thr Phe
```

```
                    180                 185                 190
Tyr Asn Gln Lys Phe Lys Gly Lys Ala Thr Leu Thr Val Asp Lys Ser
                195                 200                 205

Ser Asn Thr Ala Tyr Met Gln Leu Asn Ser Leu Thr Ser Glu Asp Ser
        210                 215                 220

Ala Val Tyr Tyr Cys Ala Arg Thr Gly Arg Tyr Glu Glu Asn Ala Met
225                 230                 235                 240

Asp Tyr Trp Gly Gln Gly Thr Ser Val Thr Val Ser Ser
                245                 250

<210> SEQ ID NO 45
<211> LENGTH: 159
<212> TYPE: PRT
<213> ORGANISM: Artificial sequence
<220> FEATURE:
<223> OTHER INFORMATION: Homo sapiens

<400> SEQUENCE: 45

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Glu Gly Gly Cys Glu Leu Arg
        35                  40                  45

Val Lys Phe Ser Arg Ser Ala Asp Ala Pro Ala Tyr Gln Gln Gly Gln
    50                  55                  60

Asn Gln Leu Tyr Asn Glu Leu Asn Leu Gly Arg Arg Glu Glu Tyr Asp
65                  70                  75                  80

Val Leu Asp Lys Arg Arg Gly Arg Asp Pro Glu Met Gly Gly Lys Pro
                85                  90                  95

Arg Arg Lys Asn Pro Gln Glu Gly Leu Tyr Asn Glu Leu Gln Lys Asp
            100                 105                 110

Lys Met Ala Glu Ala Tyr Ser Glu Ile Gly Met Lys Gly Glu Arg Arg
        115                 120                 125

Arg Gly Lys Gly His Asp Gly Leu Tyr Gln Gly Leu Ser Thr Ala Thr
    130                 135                 140

Lys Asp Thr Tyr Asp Ala Leu His Met Gln Ala Leu Pro Pro Arg
145                 150                 155

<210> SEQ ID NO 46
<211> LENGTH: 504
<212> TYPE: PRT
<213> ORGANISM: Artificial sequence
<220> FEATURE:
<223> OTHER INFORMATION: The sequence is synthesized

<400> SEQUENCE: 46

Gly Ala His Ala Asp Ile Val Leu Thr Gln Ser Pro Ala Phe Leu Ala
1               5                   10                  15

Val Ser Leu Gly Gln Arg Ala Thr Ile Ser Cys Arg Ala Ser Glu Ser
            20                  25                  30

Val Asp Asn Tyr Gly Phe Ser Phe Met Asn Trp Phe Gln Gln Lys Pro
        35                  40                  45

Gly Gln Pro Pro Lys Leu Leu Ile Tyr Ala Ile Ser Asn Arg Gly Ser
    50                  55                  60

Gly Val Pro Ala Arg Phe Ser Gly Ser Gly Ser Gly Thr Asp Phe Ser
65                  70                  75                  80
```

```
Leu Asn Ile His Pro Val Glu Glu Asp Asp Pro Ala Met Tyr Phe Cys
                85                  90                  95

Gln Gln Thr Lys Glu Val Pro Trp Thr Phe Gly Gly Gly Thr Lys Leu
            100                 105                 110

Glu Ile Lys Gly Ser Thr Ser Gly Ser Gly Lys Pro Gly Ser Gly Glu
        115                 120                 125

Gly Ser Thr Lys Gly Gln Val Gln Leu Gln Glu Ser Gly Gly Asp Leu
    130                 135                 140

Val Lys Pro Gly Gly Ser Leu Lys Leu Ser Cys Ala Ala Ser Gly Phe
145                 150                 155                 160

Thr Phe Ser His Tyr Gly Met Ser Trp Val Arg Gln Thr Pro Asp Lys
                165                 170                 175

Arg Leu Glu Trp Val Ala Thr Ile Gly Ser Arg Gly Thr Tyr Thr His
            180                 185                 190

Tyr Pro Asp Ser Val Lys Gly Arg Phe Thr Ile Ser Arg Asp Asn Asp
        195                 200                 205

Lys Asn Ala Leu Tyr Leu Gln Met Asn Ser Leu Lys Ser Glu Asp Thr
    210                 215                 220

Ala Met Tyr Tyr Cys Ala Arg Arg Ser Glu Phe Tyr Tyr Gly Asn
225                 230                 235                 240

Thr Tyr Tyr Tyr Ser Ala Met Asp Tyr Trp Gly Gln Gly Ala Ser Val
                245                 250                 255

Thr Val Ser Ser Ala Ser Phe Val Pro Val Phe Leu Pro Ala Lys Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Asn His Arg Asn Arg Phe Ser Val Val Lys Arg
            340                 345                 350

Gly Arg Lys Lys Leu Leu Tyr Ile Phe Lys Gln Pro Phe Met Arg Pro
        355                 360                 365

Val Gln Thr Thr Gln Glu Glu Asp Gly Cys Ser Cys Arg Phe Pro Glu
    370                 375                 380

Glu Glu Glu Gly Gly Cys Glu Leu Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
        435                 440                 445

Gly Leu Tyr Asn Glu Leu Gln Lys Asp Lys Met Ala Glu Ala Tyr Ser
    450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
```

<210> SEQ ID NO 47
<211> LENGTH: 496
<212> TYPE: PRT
<213> ORGANISM: Artificial sequence
<220> FEATURE:
<223> OTHER INFORMATION: The sequence is synthesized

<400> SEQUENCE: 47

```
Gly Ala His Ala Glu Val Lys Leu Val Glu Ser Gly Gly Asp Leu Val
1               5                   10                  15

Lys Pro Gly Gly Ser Leu Lys Leu Ser Cys Ala Ala Ser Gly Phe Thr
            20                  25                  30

Phe Ser Ser Tyr Gly Met Ser Trp Val Arg Gln Thr Pro Asp Lys Arg
        35                  40                  45

Leu Glu Trp Val Ala Thr Ile Ser Arg Gly Ser Tyr Thr Tyr Tyr
    50                  55                  60

Pro Asp Ser Val Lys Gly Arg Phe Thr Ile Ser Arg Asp Asn Ala Lys
65                  70                  75                  80

Asn Thr Leu Tyr Leu Gln Met Ser Ser Leu Lys Ser Glu Asp Thr Ala
                85                  90                  95

Met Tyr Tyr Cys Ala Arg Arg Glu Thr Tyr Asp Glu Lys Gly Phe Ala
            100                 105                 110

Tyr Trp Gly Gln Gly Thr Thr Val Thr Val Ser Ser Gly Gly Gly Gly
        115                 120                 125

Ser Gly Gly Gly Gly Ser Gly Gly Gly Gly Ser Asp Ile Glu Leu Thr
130                 135                 140

Gln Ser Pro Ser Ser Leu Thr Val Thr Ala Gly Glu Lys Val Thr Met
145                 150                 155                 160

Ser Cys Lys Ser Ser Gln Ser Leu Leu Asn Ser Gly Asn Gln Lys Asn
                165                 170                 175

Tyr Leu Thr Trp Tyr Gln Gln Lys Pro Gly Gln Pro Pro Lys Leu Leu
            180                 185                 190

Ile Tyr Trp Ala Ser Thr Arg Glu Ser Gly Val Pro Asp Arg Phe Thr
        195                 200                 205

Gly Ser Gly Ser Gly Arg Asp Phe Thr Leu Thr Ile Ser Ser Val Gln
    210                 215                 220

Ala Glu Asp Leu Ala Val Tyr Tyr Cys Gln Asn Asp Asn Ser His Pro
225                 230                 235                 240

Leu Thr Phe Gly Ala Gly Thr Lys Leu Glu Leu Lys Ala Ser Phe Val
                245                 250                 255

Pro Val Phe Leu Pro Ala Lys Pro Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Asn His Arg
                325                 330                 335

Asn Arg Phe Ser Val Val Lys Arg Gly Arg Lys Lys Leu Leu Tyr Ile
            340                 345                 350

Phe Lys Gln Pro Phe Met Arg Pro Val Gln Thr Thr Gln Glu Glu Asp
```

```
                  355                 360                 365
Gly Cys Ser Cys Arg Phe Pro Glu Glu Glu Gly Cys Glu Leu
370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                    405                 410                 415

Asp Val Leu Asp Lys Arg Arg Gly Arg Asp Pro Glu Met Gly Gly Lys
                420                 425                 430

Pro Arg Arg Lys Asn Pro Gln Glu Gly Leu Tyr Asn Glu Leu Gln Lys
                435                 440                 445

Asp Lys Met Ala Glu Ala Tyr Ser Glu Ile Gly Met Lys Gly Glu Arg
            450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495
```

<210> SEQ ID NO 48
<211> LENGTH: 497
<212> TYPE: PRT
<213> ORGANISM: Artificial sequence
<220> FEATURE:
<223> OTHER INFORMATION: The sequence is synthesized

<400> SEQUENCE: 48

```
Gly Ala His Ala Glu Leu Val Met Thr Gln Ser Pro Ala Ser Leu Ala
1               5                   10                  15

Val Ser Leu Gly Gln Arg Ala Thr Ile Ser Cys Arg Ala Ser Glu Ser
                20                  25                  30

Val Asp Ser Tyr Gly Lys Ser Phe Met His Trp Tyr Gln Leu Lys Pro
            35                  40                  45

Gly Gln Pro Pro Lys Leu Leu Ile Tyr Arg Ala Ser Asn Leu Glu Ser
        50                  55                  60

Gly Val Pro Ala Arg Phe Ser Gly Ser Gly Ser Arg Thr Asp Phe Thr
65                  70                  75                  80

Leu Thr Ile Asp Pro Val Glu Ala Asp Ala Ala Thr Tyr Tyr Cys
                85                  90                  95

Gln Gln Asn Asn Glu Asp Pro Trp Thr Phe Gly Gly Gly Thr Lys Leu
                100                 105                 110

Glu Ile Lys Gly Ser Thr Ser Gly Ser Gly Lys Pro Gly Ser Gly Glu
            115                 120                 125

Gly Ser Thr Lys Gly Glu Val Gln Leu Glu Gln Ser Gly Pro Glu Leu
        130                 135                 140

Val Lys Pro Gly Ala Ser Val Lys Met Ser Cys Lys Ala Ser Gly Tyr
145                 150                 155                 160

Thr Phe Thr Asn Tyr Tyr Met Lys Trp Val Lys Gln Ser His Gly Lys
                165                 170                 175

Ser Leu Glu Trp Ile Gly Asp Leu Asn Pro Asn Asn Gly Asp Thr Phe
            180                 185                 190

Tyr Asn Gln Lys Phe Lys Gly Lys Ala Thr Leu Thr Val Asp Lys Ser
        195                 200                 205

Ser Asn Thr Ala Tyr Met Gln Leu Asn Ser Leu Thr Ser Glu Asp Ser
    210                 215                 220

Ala Val Tyr Tyr Cys Ala Arg Thr Gly Arg Tyr Glu Glu Asn Ala Met
```

```
                     225                 230                 235                 240
Asp Tyr Trp Gly Gln Gly Thr Ser Val Thr Val Ser Ser Ala Ser Phe
                245                 250                 255

Val Pro Val Phe Leu Pro Ala Lys Pro Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Asn His
                325                 330                 335

Arg Asn Arg Phe Ser Val Val Lys Arg Gly Arg Lys Lys Leu Leu Tyr
                340                 345                 350

Ile Phe Lys Gln Pro Phe Met Arg Pro Val Gln Thr Thr Gln Glu Glu
            355                 360                 365

Asp Gly Cys Ser Cys Arg Phe Pro Glu Glu Glu Glu Gly Gly Cys Glu
        370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 49
<211> LENGTH: 780
<212> TYPE: DNA
<213> ORGANISM: Artificial sequence
<220> FEATURE:
<223> OTHER INFORMATION: The sequence is synthesized

<400> SEQUENCE: 49
ggcgcgcatg ccgatattgt gctcacacaa tcacccgcgt tccttgccgt tagtcttgga     60
caaagagcga cgattagctg tagggcatct gagagcgtag acaattatgg atttagtttt    120
atgaactggt ttcagcaaaa gccaggccaa cctccgaaac tgttgatcta tgcaatatca    180
aaccgaggga gtggggttcc tgcaaggttc tcagggagtg gcagcgggac ggacttttca    240
cttaatatcc atcccgtcga ggaagatgat ccggcgatgt acttctgcca gcagacgaaa    300
gaggttcctt ggacctttgg cggggggtacg aagttggaga tcaaaggttc aacttcagga    360
tccggaaagc cgggctccgg agagggttcc actaagggcc aggtgcagct ccaggaaagt    420
ggcggagacc ttgttaagcc ggggggttca ctcaaacttt catgtgctgc gagtggcttt    480 acctttttcac actatgggat gtcctgggta cggcaaacgc ctgataaacg ccttgagtgg    540
```

| | |
|---|---|
| gtcgctacta ttggaagcag gggaacatat acacattacc cagattccgt taaaggtaga | 600 |
| tttactatca gtagggacaa tgataagaac gcactgtatt tgcaaatgaa ctccctgaaa | 660 |
| tccgaggata cggcaatgta ttactgtgct agacgaagcg aatttatta ctatggcaat | 720 |
| acatattact acagcgctat ggactactgg ggccagggtg ccagtgtgac ggtctcctct | 780 |

<210> SEQ ID NO 50
<211> LENGTH: 756
<212> TYPE: DNA
<213> ORGANISM: Artificial sequence
<220> FEATURE:
<223> OTHER INFORMATION: The sequence is synthesized

<400> SEQUENCE: 50

| | |
|---|---|
| ggcgcgcatg ccgaagttaa gctggtcgaa agcggtggtg atcttgtcaa gccgggtggg | 60 |
| tctctcaagc tctcctgcgc tgctagtggc ttcaccttct ctagctacgg gatgtcatgg | 120 |
| gtccggcaga ccccgataa aagactggaa tgggttgcga ctataagccg cggtggcagt | 180 |
| tacacctact accctgattc cgtcaaaggg cgctttacca taagcagaga taacgccaaa | 240 |
| aacacactgt acttgcagat gagttcactt aaaagtgagg atacggccat gtactattgc | 300 |
| gcccgccggg aaacctatga tgagaagggg ttcgcttatt gggggcaagg tacgactgta | 360 |
| acggtctcat caggtggtgg gggaagcggt ggggagggt caggaggggg tgggagcgat | 420 |
| atagagttga cccaatctcc cagtagtctt accgtcacgg cgggagaaaa agtaacgatg | 480 |
| agctgcaagt ctagtcaatc acttcttaac agtggaaatc aaaaaaatta tctcacctgg | 540 |
| tatcaacaga agccaggaca accgcctaaa ttgctgatat attgggcgag taccagagaa | 600 |
| tcaggcgtgc cggaccgatt taccggttca ggttctggtc gggactttac tctgactatt | 660 |
| tccagtgttc aggcagaaga tcttgccgtg tattattgcc agaatgataa ttcacacccg | 720 |
| ttgacatttg gggcgggcac aaagttggag ctcaaa | 756 |

<210> SEQ ID NO 51
<211> LENGTH: 759
<212> TYPE: DNA
<213> ORGANISM: Artificial sequence
<220> FEATURE:
<223> OTHER INFORMATION: The sequence is synthesized

<400> SEQUENCE: 51

| | |
|---|---|
| ggcgcgcatg ccgaactggt aatgacccaa tcaccagctt cacttgctgt ctctcttggg | 60 |
| caacgagcta ctatctcatg tagagcctcc gagagtgtcg attcctatgg caaatctttc | 120 |
| atgcactggt accaactcaa acctggccaa ccacccaagc tcctgatata tagagccagt | 180 |
| aacttggaaa gtggggttcc tgcccggttc tccggtagtg gttcaagaac agatttcacg | 240 |
| ctgacaatag atccagtgga agcggacgat gccgccacat attattgcca acaaaataat | 300 |
| gaggatccgt ggacctttgg cggagggacc aagcttgaaa ttaaaggttc aacgtccgga | 360 |
| agtggaaaac caggtagcgg agagggctct acaaaaggcg aggttcaact cgaacagagt | 420 |
| ggtccagagc tggtcaagcc tggtgcgagt gttaaaatgt cctgtaaagc gtccggctac | 480 |
| acatttacca actattacat gaaatgggtg aagcaatctc acggaaagag tttggagtgg | 540 |
| ataggggacc tgaatcctaa caatggagat acgttctata ccaaaagtt caagggaaaa | 600 |
| gcaacgctca cggtcgataa gagcagtaat acggcctata tgcagttgaa cagcctgaca | 660 |
| agcgaggact cagctgtcta ctactgtgct cgcactggcc ggtatgaaga gaatgcgatg | 720 |

```
gactactggg ggcaggggac aagcgtaacg gtttctagc                    759
```

<210> SEQ ID NO 52
<211> LENGTH: 477
<212> TYPE: DNA
<213> ORGANISM: Artificial sequence
<220> FEATURE:
<223> OTHER INFORMATION: Homo sapiens

<400> SEQUENCE: 52

```
cgtttctctg ttgttaaacg gggcagaaag aagctcctgt atatattcaa acaaccattt    60
atgagaccag tacaaactac tcaagaggaa gatggctgta gctgccgatt tccagaagaa   120
gaagaaggag gatgtgaact gagagtgaag ttcagcagga gcgcagacgc ccccgcgtac   180
cagcagggcc agaaccagct ctataacgag ctcaatctag gacgaagaga ggagtacgat   240
gttttggaca agagacgtgg ccgggaccct gagatggggg gaaagccgag aaggaagaac   300
cctcaggaag gcctgtacaa tgaactgcag aaagataaga tggcggaggc ctacagtgag   360
attgggatga aaggcgagcg ccggaggggc aaggggcacg atggccttta ccagggtctc   420
agtacagcca ccaaggacac ctacgacgcc cttcacatgc aggccctgcc ccctcgc     477
```

<210> SEQ ID NO 53
<211> LENGTH: 1581
<212> TYPE: DNA
<213> ORGANISM: Artificial sequence
<220> FEATURE:
<223> OTHER INFORMATION: The sequence is synthesized

<400> SEQUENCE: 53

```
atgcttctcc tggtgacaag ccttctgctc tgtgagttac cacacccagc attcctcctg    60
atcccaggcg cgcatgccga tattgtgctc acacaatcac ccgcgttcct tgccgttagt   120
cttggacaaa gagcgacgat tagctgtagg gcatctgaga gcgtagacaa ttatggattt   180
agttttatga actggtttca gcaaaagcca ggccaacctc cgaaactgtt gatctatgca   240
atatcaaacc gagggagtgg ggttcctgca aggttctcag ggagtggcag cgggacggac   300
ttttcactta atatccatcc cgtcgaggaa gatgatccgg cgatgtactt ctgccagcag   360
acgaaagagg ttccttggac ctttggcggg ggtacgaagt tggagatcaa aggttcaact   420
tcaggatccg gaaagccggg ctccggagag ggttccacta agggccaggt gcagctccag   480
gaaagtggcg gagaccttgt taagccgggg ggttcactca actttcatg tgctgcgagt   540
ggctttacct tttcacacta tgggatgtcc tgggtacggc aaacgcctga taaacgcctt   600
gagtgggtcg ctactattgg aagcagggga acatatacac attcccaga ttccgttaaa   660
ggtagattta ctatcagtag ggacaatgat aagaacgcac tgtatttgca aatgaactcc   720
ctgaaatccg aggatacggc aatgtattac tgtgctagac gaagcgaatt ttattactat   780
ggcaatacat attactacag cgctatggac tactggggcc agggtgccag tgtgacggtc   840
tcctctgcta gcttcgtgcc ggtcttcctg ccagcgaagc ccaccacgac gccagcgccg   900
cgaccaccaa caccggcgcc caccatcgcg tcgcagcccc tgtccctgcg cccagaggcg   960
tgccggccag cggcgggggg cgcagtgcac acgaggggg tggacttcgc ctgtgatatc  1020
tacatctggg cgcccttggc cgggacttgt ggggtccttc tcctgtcact ggttatcacc  1080
ctttactgca accacaggaa ccgtttctct gttgttaaac ggggcagaaa gaagctcctg  1140
tatatattca acaaccattt atgagacca gtacaaacta ctcaagagga agatggctgt  1200
agctgccgat tccagaagaa agaagaagga ggatgtgaac tgagagtgaa gttcagcagg  1260
```

-continued

| | | |
|---|---|---|
| agcgcagacg ccccgcgta ccagcagggc cagaaccagc tctataacga gctcaatcta | 1320 |
| ggacgaagag aggagtacga tgttttggac aagagacgtg gccggaccc tgagatgggg | 1380 |
| ggaaagccga gaaggaagaa ccctcaggaa ggcctgtaca atgaactgca gaaagataag | 1440 |
| atggcggagg cctacagtga gattgggatg aaaggcgagc gccggagggg caaggggcac | 1500 |
| gatggccttt accagggtct cagtacagcc accaaggaca cctacgacgc ccttcacatg | 1560 |
| caggccctgc cccctcgctg a | 1581 |

<210> SEQ ID NO 54
<211> LENGTH: 1557
<212> TYPE: DNA
<213> ORGANISM: Artificial sequence
<220> FEATURE:
<223> OTHER INFORMATION: The sequence is synthesized

<400> SEQUENCE: 54

| | | |
|---|---|---|
| atgcttctcc tggtgacaag ccttctgctc tgtgagttac cacacccagc attcctcctg | 60 |
| atcccaggcg cgcatgccga agttaagctg gtcgaaagcg gtggtgatct tgtcaagccg | 120 |
| ggtgggtctc tcaagctctc ctgcgctgct agtggcttca ccttctctag ctacgggatg | 180 |
| tcatgggtcc ggcagacccc cgataaaaga ctggaatggg ttgcgactat aagccgcggt | 240 |
| ggcagttaca cctactaccc tgattccgtc aaagggcgct ttaccataag cagagataac | 300 |
| gccaaaaaca cactgtactt gcagatgagt tcacttaaaa gtgaggatac ggccatgtac | 360 |
| tattgcgccc gccgggaaac ctatgatgag aaggggttcg cttattgggg caaggtacg | 420 |
| actgtaacgg tctcatcagg tggtggggga agcggtgggg gagggtcagg aggggtggg | 480 |
| agcgatatag agttgaccca atctcccagt agtcttaccg tcacggcggg agaaaaagta | 540 |
| acgatgagct gcaagtctag tcaatcactt cttaacagtg gaaatcaaaa aaattatctc | 600 |
| acctggtatc aacagaagcc aggacaaccg cctaaattgc tgatatattg ggcgagtacc | 660 |
| agagaatcag gcgtgccgga ccgatttacc ggttcaggtt ctggtcggga cttactctg | 720 |
| actatttcca gtgttcaggc agaagatctt gccgtgtatt attgccagaa tgataattca | 780 |
| cacccgttga catttgggc gggcacaaag ttggagctca aagctagctt cgtgccggtc | 840 |
| ttcctgccag cgaagcccac cacgacgcca gcgccgcgac caccaacacc ggcgcccacc | 900 |
| atcgcgtcgc agcccctgtc cctgcgccca gaggcgtgcc ggccagcggc ggggggcgca | 960 |
| gtgcacacga gggggctgga cttcgcctgt gatatctaca tctgggcgcc cttggccggg | 1020 |
| acttgtgggg tccttctcct gtcactggtt atcacccttt actgcaacca caggaaccgt | 1080 |
| ttctctgttg ttaaacgggg cagaaagaag ctcctgtata tattcaaaca accatttatg | 1140 |
| agaccagtac aaactactca agaggaagat ggctgtagct gccgatttcc agaagaagaa | 1200 |
| gaaggaggat gtgaactgag agtgaagttc agcaggagcg cagacgcccc cgcgtaccag | 1260 |
| cagggccaga accagctcta taacgagctc aatctaggac gaagagagga gtacgatgtt | 1320 |
| ttggacaaga cgtggccg ggaccctgag atggggggaa agccgagaag gaagaaccct | 1380 |
| caggaaggcc tgtacaatga actgcagaaa gataagatgg cggaggccta cagtgagatt | 1440 |
| gggatgaaag gcgagcgccg gaggggcaag ggcacgatg cctttacca gggtctcagt | 1500 |
| acagccacca aggacaccta cgacgccctt cacatgcagg ccctgccccc tcgctga | 1557 |

<210> SEQ ID NO 55
<211> LENGTH: 1560
<212> TYPE: DNA

<213> ORGANISM: Artificial sequence
<220> FEATURE:
<223> OTHER INFORMATION: The sequence is synthesized

<400> SEQUENCE: 55

```
atgcttctcc tggtgacaag ccttctgctc tgtgagttac cacacccagc attcctcctg      60
atcccaggcg cgcatgccga actggtaatg acccaatcac cagcttcact tgctgtctct     120
cttgggcaac gagctactat ctcatgtaga gcctccgaga gtgtcgattc ctatggcaaa     180
tctttcatgc actggtacca actcaaacct ggccaaccac ccaagctcct gatatataga     240
gccagtaact tggaaagtgg ggttcctgcc cggttctccg gtagtggttc aagaacagat     300
ttcacgctga caatagatcc agtggaagcg acgatgccg ccacatatta ttgccaacaa      360
aataatgagg atccgtggac ctttggcgga gggaccaagc ttgaaattaa aggttcaacg     420
tccggaagtg gaaaaccagg tagcggagag ggctctacaa aaggcgaggt tcaactcgaa     480
cagagtggtc cagagctggt caagcctggt gcgagtgtta aaatgtcctg taaagcgtcc     540
ggctacacat ttaccaacta ttacatgaaa tgggtgaagc aatctcacgg aaagagtttg     600
gagtggatag ggacctgaa tcctaacaat ggagatacgt tctataacca aaagttcaag      660
ggaaaagcaa cgctcacggt cgataagagc agtaatacgg cctatatgca gttgaacagc     720
ctgacaagcg aggactcagc tgtctactac tgtgctcgca ctggccggta tgaagagaat     780
gcgatggact actgggggca ggggacaagc gtaacggttt ctagcgctag cttcgtgccg     840
gtcttcctgc cagcgaagcc caccacgacg ccagcgccgc gaccaccaac accggcgccc     900
accatcgcgt cgcagcccct gtccctgcgc ccagaggcgt gccggccagc ggcgggggc      960
gcagtgcaca cgagggggct ggacttcgcc tgtgatatct acatctgggc gcccttggcc    1020
gggacttgtg gggtccttct cctgtcactg gttatcaccc tttactgcaa ccacaggaac    1080
cgtttctctg ttgttaaacg gggcagaaag aagctcctgt atatattcaa acaaccattt    1140
atgagaccag tacaaactac tcaagaggaa gatgctgta gctgccgatt ccagaagaa      1200
gaagaaggag gatgtgaact gagagtgaag ttcagcagga gcgcagacgc ccccgcgtac    1260
cagcagggcc agaaccagct ctataacgag ctcaatctag gacgaagaga ggagtacgat    1320
gttttggaca agagacgtgg ccgggaccct gagatggggg gaaagccgag aaggaagaac    1380
cctcaggaag gcctgtacaa tgaactgcag aaagataaga tggcggaggc ctacagtgag    1440
attgggatga aggcgagcg ccggaggggc aaggggcacg atggccttta ccagggtctc     1500
agtacagcca ccaaggacac ctacgacgcc cttcacatgc aggccctgcc ccctcgctga    1560
```

<210> SEQ ID NO 56
<211> LENGTH: 589
<212> TYPE: DNA
<213> ORGANISM: Artificial sequence
<220> FEATURE:
<223> OTHER INFORMATION: cytomegalovirus

<400> SEQUENCE: 56

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
```

```
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatc                589
```

<210> SEQ ID NO 57
<211> LENGTH: 18
<212> TYPE: DNA
<213> ORGANISM: Artificial sequence
<220> FEATURE:
<223> OTHER INFORMATION: T7 phage

<400> SEQUENCE: 57

```
taatacgact cactatag                                                   18
```

<210> SEQ ID NO 58
<211> LENGTH: 44
<212> TYPE: DNA
<213> ORGANISM: Artificial sequence
<220> FEATURE:
<223> OTHER INFORMATION: Homo sapiens

<400> SEQUENCE: 58

```
aaataagaga gaaagaaga gtaagaagaa atataagagc cacc                       44
```

<210> SEQ ID NO 59
<211> LENGTH: 94
<212> TYPE: DNA
<213> ORGANISM: Homo sapiens

<400> SEQUENCE: 59

```
gctgccttct gcggggcttg ccttctggcc atgcccttct tctctccctt gcacctgtac    60
ctcttggtct ttgaataaag cctgagtagg aagt                                 94
```

<210> SEQ ID NO 60
<211> LENGTH: 34
<212> TYPE: DNA
<213> ORGANISM: Artificial sequence
<220> FEATURE:
<223> OTHER INFORMATION: P1 phage

<400> SEQUENCE: 60

```
ataacttcgt atagcataca ttatacgaag ttat                                 34
```

<210> SEQ ID NO 61
<211> LENGTH: 23
<212> TYPE: DNA
<213> ORGANISM: Artificial sequence
<220> FEATURE:
<223> OTHER INFORMATION: Vaccinia virus

<400> SEQUENCE: 61

```
taacgataat agatacggaa cgg                                             23
```

<210> SEQ ID NO 62
<211> LENGTH: 23

```
<212> TYPE: DNA
<213> ORGANISM: Artificial sequence
<220> FEATURE:
<223> OTHER INFORMATION: Vaccinia virus

<400> SEQUENCE: 62
gtgtatgaaa tgctttaagg agg                                              23
```

THERAPEUTIC AGENTS COMPRISING NUCLEIC ACIDS AND CAR-MODIFIED IMMUNE CELLS, AND USES THEREOF

SEQUENCE LISTING

A Sequence Listing in ASCII text format, submitted pursuant to 37 C.F.R. § 1.821, entitled UP-206521-Sequence-listing-revised.txt, 70 kilobytes in size, created on May 7, 2021 and filed via EFS-Web, is hereby incorporated by reference in its entirety.

FIELD OF THE INVENTION

The present invention belongs to the field of medical bioengineering, and particularly to a therapeutic agent comprising nucleic acids and CAR-modified immune cells, a labeling polypeptide, a chimeric antigen receptor, a coding nucleic acid, an expression vector, a recombinant virus, a kit and uses thereof.

BACKGROUND OF THE INVENTION

Cancer immunotherapy is a treatment method that specifically clears away tiny residual cancer lesions or significantly inhibits the proliferation of cancer cells by activating the immune system of the body. This treatment method has the advantages of long effective duration and small side effects, and is called the fourth mode of modern cancer treatment. In recent years, a lot of progress has been made in cancer immunotherapy. Journal "Science" listed cancer immunotherapy as a important scientific breakthrough in 2013. The chimeric antigen receptor CAR-modified immune cells are currently the most effective and promising tumor cell immunotherapy product. CAR immune cells technology has the specificity of antibody drugs and the sustainability of cell therapy and is a precision medicine and personalized medicine. In the next 5 years, immunotherapy, including CAR immunotherapy, is expected to replace chemotherapy and become the standard therapy for cancer treatment. Currently, CAR immunotherapy mainly uses T-cells as a carrier and has made revolutionary progress in the treatment of malignant blood cancers. The global market has reached ten billions of dollars. However, the current results of CAR-T in the treatment of solid tumors are not very well and problems such as safety, effectiveness and mass production still need to be solved. After these problems are resolved, CAR immunotherapy will gradually flood into the solid tumor market of 100 billions of dollars.

CAR is an artificially modified receptor, and therefore a specific receptor that recognizes any antigen can be grafted onto immune effector cells. The basic design of CAR includes a tumor-associated antigen (TAA) binding region (usually derived from the scFV fragment of a monoclonal antibody antigen binding region), an extracellular hinge region, a transmembrane region and an intracellular signal region. Since different regions of this receptor have different sources, this receptor is called chimeric receptor. Simply put, CAR-T is a connection of an antibody that recognize an antigen on the surface of tumor cell and signal molecules which is necessary to activate T cells, such that T cells can directly attack cancer cells under the guidance of the antibody. CAR immune cells technology overcomes a challenging problem in the development of anti-tumor immunotherapy, that is, the immune escape mechanism of tumor formation. The escape mechanism can protect the tumor from the attack of the immune system and mainly includes decreased processing ability to antigens, the decreased expression of histocompatibility complex, decreased expression of antigens on tumor surface, decreased expression of cytokines and increased expression of immunosuppressive molecules. The targets of CAR immune cells are different from that of cytotoxic T lymphocytes. Instead of attacking the antigen presented by the antigen presentation pathway on the tumor surface, it attacks specific molecules on the tumor surface which can be proteins or other non-protein molecules. The expression of these molecules has nothing to do with the processing ability to tumor cell antigen and the expression of histocompatibility complex. Therefore, the function of CAR immune cells is not restricted by the regulation of histocompatibility complex.

However, CAR-T technology still has great challenges in the treatment of solid tumors. The main difficulties include: 1) Solid tumors express highly heterogeneous, that is, divers, tumor antigens which makes it easy for cancer cells to escape from the surveillance of the immune system. This is different from blood cancers. For example, CD19 leukemia is basically CD19 positive. Due to the diversity of solid tumor antigens, it is difficult to find a suitable targeted site that is suitable for killing all cancer cells and residual targeted site-negative cancer cells will cause tumor recurrence. 2) Many tumor antigens of solid tumors are also expressed in normal tissues, which makes it difficult to design tumor-specific CARs, the off-target probability is high, and the risk of targeting/off-target toxicity is high. 3) T-cells are poor in tumor homing. The cells of solid tumor are wrapped by a dense matrix to form the tumor microenvironment. The matrix, which is assembled by the recruited normal tissues and bone marrow-derived (stromal) cells, prevents immune cells from penetrating this matrix barrier. 4) Solid tumors have strong Immunosuppressive ability and many cells in the tumor microenvironment can inhibit the anti-cancer function of immune cells. Therefore, the CAR-T that infiltrates into solid tumors cannot achieve a highly effective cancer cell killing effect.

SUMMARY OF THE INVENTION

In order to solve the above-mentioned problems in the prior art, the present invention provides a therapeutic agent, a labeling polypeptide, a chimeric antigen receptor, a coding nucleic acid, an expression vector, a recombinant virus, a kit and uses thereof.

Specifically, the present invention provides:
(1) A therapeutic agent for treatment of tumors and/or cancers, comprising:
(a) a first composition, wherein the first composition comprises a first active ingredient in a first pharmaceutically acceptable carrier, and the first active ingredient includes or contains a nucleic acid having a labeling polypeptide coding sequence for being introduced into a tumor cell and/or a cancer cell; the labeling polypeptide has a extracellular antigen determining region, a spacer portion and a transmembrane portion that are operatively linked, which can be expressed to form modification on the surface of the tumor cell and/or cancer cell; an amino acid sequence of the extracellular antigen determining region comprises one or more amino acid sequences of epitope polypeptide; and wherein, in the natural state, an amino acid sequence of a protein on cell membrane or a secreted protein of mammal does not comprise the amino acid sequence of the epitope polypeptide; and (b) a second composition, wherein the second composition comprises a second active ingredient in a second pharmaceutically acceptable carrier, and the second active ingredient comprises a chimeric antigen receptor-modified immune cell; the chimeric antigen receptor-modified immune cell can specifically recognize and bind to the extracellular antigen determining region of the labeling polypeptide.

(2) The therapeutic agent of (1), wherein the amino acid sequence of the epitope polypeptide is derived from an amino acid sequence of a protein that exists in the nature, or the amino acid sequence of the epitope polypeptide is an artificially synthesized amino acid sequence that does not exist in the nature.

(3) The therapeutic agent of (2), wherein the protein that exists in the nature includes mammalian intracellular proteins, viral proteins, and all other non-mammalian proteins.

(4) The therapeutic agent of (1), wherein the amino acid sequence of the epitope polypeptide includes an amino acid sequence of the following tags: Myc tag, HA tag, Strep tag II, Flag tag, HAT tag, S tag, S1 tag, protein C tag, tag-100 tag, E2 tag, TAP tag, HSV tag, KT3 tag, V5 tag, VSV-G tag, His tag or RFP tag.

(5) The therapeutic agent of (1), wherein the amino acid sequence of the extracellular antigen determining region is as shown in SEQ ID NO: 1, SEQ ID NO: 2, SEQ ID NO: 3, SEQ ID NO: 4 or SEQ ID NO: 5.

(6) The therapeutic agent of (1), wherein the spacer portion is derived from the hinge region of CD8α, the hinge region of IgG or the hinge region of IgD; preferably, an amino acid sequence of the spacer portion is as shown in SEQ ID NO: 6; wherein the transmembrane portion is derived from the transmembrane region of CD8, CD3ζ, CD4 or CD28; preferably, an amino acid sequence of the transmembrane portion is as shown in SEQ ID NO: 7.

(7) The therapeutic agent of (1), wherein an amino acid sequence of the labeling polypeptide is as shown in SEQ ID NO: 11, SEQ ID NO: 12, SEQ ID NO: 13, SEQ ID NO: 14 or SEQ ID NO: 15.

(8) The therapeutic agent of (1), wherein the nucleic acid includes DNA or RNA; and the RNA includes mRNA transcribed from the DNA.

(9) The therapeutic agent of (1), wherein the first active ingredient is a recombinant virus, and the genome of the recombinant virus has the labeling polypeptide coding sequence; wherein the recombinant virus includes replication-selective recombinant oncolytic virus or replication-defective recombinant virus.

(10) The therapeutic agent of (9), wherein the recombinant oncolytic virus is derived from a genetically mutated virus with oncolytic effect or a wild-type virus with oncolytic effect; preferably, the recombinant oncolytic virus is derived from adenovirus, poxvirus, herpes simplex virus, measles virus, Semliki forest virus, vesicular stomatitis virus, polio virus, retrovirus, reovirus, Seneca valley virus, Echo-type enterovirus, Coxsackie virus, Newcastle disease virus and Malaba virus with oncolytic effect.

(11) The therapeutic agent of (1), wherein the chimeric antigen receptor includes an antigen-binding domain, a spacer region, a transmembrane region and an intracellular domain that are operatively and orderly linked, and the antigen-binding domain can specifically recognize and bind to the extracellular antigen determining region of the labeling polypeptide.

(12) The therapeutic agent of (11), wherein an amino acid sequence of the antigen-binding domain is as shown in SEQ ID NO: 42, SEQ ID NO: 43 or SEQ ID NO: 44.

(13) The therapeutic agent of (11), wherein the intracellular domain is derived from a lymphocyte intracellular activation signal transduction region and an optional lymphocyte costimulatory signal transduction region, wherein the intracellular activation signal transduction region is selected from an intracellular activation signal transduction region of CD3ζ or DAP12; the optional lymphocyte costimulatory signal transduction region is selected from a costimulatory signal transduction region of 4-1BB, CD28, CD27, OX40, GITR, and/or ICOSS.

(14) The therapeutic agent of (11), wherein the spacer region is derived from a hinge region of CD8α, a hinge region of IgG or a hinge region of IgD, and a transmembrane region is derived from a transmembrane region of CD8α, CD3ζ. CD4 or CD28.

(15) The therapeutic agent of (11), wherein the amino acid sequence of the chimeric antigen receptor is as shown in SEQ ID NO: 46, SEQ ID NO: 47 or SEQ ID NO: 48.

(16) The therapeutic agent of (1), wherein the immune cells include T cells or NK cells; wherein the NK cells include autologous NK cells, allogeneic NK cells, or NK cell strains, and the T cells include naive T cells or their precursor cells, effector T cells, memory T cells, NKT cells, or T cell strains.

(17) The therapeutic agent of (1), wherein the first composition and the second composition are present separately in the therapeutic agent without being mixed together.

(18) The therapeutic agent of (8), wherein the first composition comprises a therapeutically effective amount of the DNA or a therapeutically effective amount of the mRNA.

(19) The therapeutic agent of (9), wherein the first composition comprises a therapeutically effective amount of the recombinant virus.

(20) The therapeutic agent of (1), wherein the second composition comprises a therapeutically effective amount of the chimeric antigen receptor-modified immune cell.

(21) The therapeutic agent of (8), wherein the DNA is formulated to be administered by intratumoral injection or intravenously; and the mRNA is formulated to be administered by intratumoral injection or intravenously.

(22) The therapeutic agent of (9), wherein the recombinant virus is formulated to be administered by intratumoral injection or intravenously.

(23) The therapeutic agent of (1), wherein the chimeric antigen receptor-modified immune cell is formulated to be administered intravenously or locally.

(24) The therapeutic agent of (1), wherein the therapeutic agent is composed of the first composition and the second composition.

(25) Use of the therapeutic agent of any one of (1) to (24) in the preparation of drugs for treatment of tumors and/or cancers.

(26) The use of (25), wherein the tumors and/or cancers include: breast cancer, head and neck tumor, synovial cancer, kidney cancer, connective tissue cancer, melanoma, lung cancer, esophageal cancer, colon cancer, rectal cancer, brain cancer, liver cancer, bone cancer, choriocarcinoma, gastrinoma, pheochromocytoma, prolactinoma, von Hippel-Lindau disease, Zollinger- Ellison syndrome, anal cancer, cholangiocarcinoma, bladder cancer, ureteral carcinoma, glioma, neuroblastoma, meningioma, spinal cord tumor, osteochondroma, Ewing's sarcoma, cancer of unknown primary site, carcinoid, fibrosarcoma, Paget's disease, cervix carcinoma, gallbladder cancer, eye cancer, Kaposi's sarcoma, prostate cancer, testicular cancer, cutaneous squamous cell carcinoma, mesothelioma, multiple myeloma, ovarian cancer, pancreatic endocrine tumor, glucagon tumor, pancreatic cancer, penile cancer, pituitary cancer, soft tissue sarcoma, retinoblastoma, small bowel cancer, gastric cancer, thymic cancer, trophoblastic carcinoma, hydatidiform mole, endometrial cancer, vaginal cancer, vulvar cancer, mycosis fungoides, insulinoma, heart cancer, meningeal cancer, peritoneal cancer, pleural cancer and blood cancer.

(27) A labeling polypeptide, characterized in that the labeling polypeptide has an extracellular antigen determining region, a spacer portion and a transmembrane portion that are operatively linked and the labeling polypeptide can be expressed to form modification on the surface of a tumor cell and/or a cancer cell; an amino acid sequence of the extracellular antigen determining region comprises one or more amino acid sequences of epitope polypeptide; and wherein, in the natural state, an amino acid sequence of a protein on cell membrane or a secreted protein of mammal does not comprise the amino acid sequence of the epitope polypeptide.

(28) The labeling polypeptide of (27), wherein the amino acid sequence of the epitope polypeptide is derived from an amino acid sequence of a protein that exists in the nature, or the amino acid sequence of the epitope polypeptide is an artificially synthesized amino acid sequence that does not exist in the nature.

(29) The labeling polypeptide of (28), wherein the protein that exists in the nature includes mammalian intracellular proteins, viral proteins, and all other non-mammalian proteins.

(30) The labeling polypeptide of (27), wherein the amino acid sequence of the epitope polypeptide includes an amino acid sequence of the following tags: Myc tag, HA tag, Strep tag II, Flag tag, HAT tag, S Tag, S1 tag, protein C tag, tag-100 tag, E2 tag, TAP tag, HSV tag, KT3 tag, V5 tag, VSV-G tag, His tag or RFP tag.

(31) The labeling polypeptide of (27), wherein the amino acid sequence of the extracellular antigen determining region is as shown in SEQ ID NO: 1, SEQ ID NO: 2, SEQ ID NO: 3, SEQ ID NO: 4 or SEQ ID NO: 5.

(32) The labeling polypeptide of (27), wherein the spacer portion is derived from a hinge region of CD8α, a hinge region of IgG or a hinge region of IgD; preferably, an amino acid sequence of the spacer portion is as shown in SEQ ID NO: 6; wherein the transmembrane portion is derived from a transmembrane region of CD8, CD3ζ, CD4 or CD28; preferably, an amino acid sequence of the transmembrane portion is as shown in SEQ ID NO: 7.

(33) The labeling polypeptide of (27), wherein an amino acid sequence of the labeling polypeptide is as shown in SEQ ID NO: 11, SEQ ID NO: 12, SEQ ID NO: 13, SEQ ID NO: 14 or SEQ ID NO: 15.

(34) An isolated nucleic acid having a coding sequence of the labeling polypeptide of any one of (27) to (33).

(35) The nucleic acid of (34), wherein the nucleic acid orderly comprises operatively linked promoter, signal peptide coding sequence and the coding sequence of the labeling polypeptide of any one of (27) to (33).

(36) The nucleic acid of (34), wherein the nucleic acid includes DNA and mRNA.

(37) A recombinant expression vector, wherein the recombinant expression vector orderly comprises operatively linked promoter, signal peptide coding sequence and the coding sequence of the labeling polypeptide of any one of (27) to (33).

(38) An isolated recombinant virus, wherein a genome of the recombinant virus comprises orderly and operatively linked promoter, signal peptide coding sequence and a coding sequence of the labeling polypeptide of any one of (27) to (33), and wherein the labeling polypeptide can be expressed to form modification on the surface of a tumor cell and/or a cancer cell; and the recombinant virus includes replication-selective recombinant oncolytic virus or replication-deficient recombinant virus.

(39) The recombinant virus of (38), wherein the recombinant virus is replication-selective recombinant oncolytic virus, and the recombinant oncolytic virus is derived from a genetically mutated virus with oncolytic effect or a wild-type virus with oncolytic effect; preferably, the recombinant oncolytic virus is derived from adenovirus, poxvirus, herpes simplex virus, measles virus, Semliki forest virus, vesicular stomatitis virus, polio virus, retrovirus, reovirus, Seneca valley virus, Echo-type enterovirus, Coxsackie virus, Newcastle disease virus and Malaba virus with oncolytic effect.

(40) A chimeric antigen receptor which comprises an antigen-binding domain, a spacer region, a transmembrane region and an intracellular domain that are orderly and operatively linked and is characterized in that the antigen-binding domain can recognize and bind to the extracellular antigen determining region of the labeling polypeptide of any one of (27) to (33).

(41) The chimeric antigen receptor of (40), wherein an amino acid sequence of the antigen-binding domain is as shown in SEQ ID NO: 42, SEQ ID NO: 43 or SEQ ID NO: 44.

(42) The chimeric antigen receptor of (40), wherein the intracellular domain is derived from a lymphocyte intracellular activation signal transduction region and an optional lymphocyte costimulatory signal transduction region, wherein a intracellular activation signal transduction region is selected from the intracellular activation signal transduction region of CD3ζ or DAP12; the optional lymphocyte costimulatory signal transduction region is selected from a costimulatory signal transduction regions of 4-1BB, CD28, CD27, OX40, GITR, and/or ICOSS.

(43) The chimeric antigen receptor of (40), wherein the spacer region is derived from a hinge region of CD8α, a hinge region of IgG or a hinge region of IgD, and the transmembrane region is derived from a transmembrane region of CD8α, CD3ζ, CD4 or CD28.

(44) The chimeric antigen receptor of (40), wherein an amino acid sequence of the chimeric antigen receptor is as shown in SEQ ID NO: 46, SEQ ID NO: 47 or SEQ ID NO: 48.

(45) An isolated DNA having a coding sequence of the chimeric antigen receptor of any one of (40) to (44).

(46) The DNA of (45), a nucleotide sequence of which is as shown in SEQ ID NO: 53, SEQ ID NO: 54 or SEQ ID NO: 55.

(47) An isolated mRNA transcribed from the DNA of (45) or (46).
(48) A recombinant expression vector, wherein the recombinant expression vector orderly comprises operatively linked promoter, signal peptide coding sequence and a coding sequence of the chimeric antigen receptor of any one of (40) to (44).
(49) A chimeric antigen receptor modified immune cell, the surface of the immune cell is modified by the chimeric antigen receptor of any one of (40) to (44).
(50) The chimeric antigen receptor modified immune cell of (49), wherein the immune cell is NK cell or T cell; wherein the NK cells include autologous NK cells, allogeneic NK cells or NK cell strains, and The T cells include primitive T cells or their precursor cells, effector T cells, memory T cells, NKT cells, or T cell strains.
(51) A kit of combinational drugs with synergistic effects for treatment of tumors and/or cancers, comprising:
a first container comprising the first composition of the therapeutic agent of any one of (1) to (24);
a second container comprising the second composition of the therapeutic agent of any one of (1) to (24), wherein the first container is separate from the second container; and
instructions specifying the timing and routes of administration.
(52) Use of the nucleic acid of any one of (34) to (36) in the preparation of drugs for the treatment or prevention of tumors and/or cancers.
(53) Use of the recombinant virus of (38) or (39) in the preparation of drugs for the treatment or prevention of tumors and/or cancers.
(54) Use of the chimeric antigen receptor modified immune cell of (49) or (50) in the preparation of drugs for treatment or prevention of tumors and/or cancers.
(55) Use of the kit of (51) in the preparation of drugs for treatment or prevention of tumors and/or cancers.
(56) The use of any one of (52) to (55), wherein the tumors and/or cancers include: breast cancer, head and neck tumor, synovial cancer, kidney cancer, connective tissue cancer, melanoma, lung cancer, esophageal cancer, colon cancer, rectal cancer, brain cancer, liver cancer, bone cancer, choriocarcinoma, gastrinoma, pheochromocytoma, prolactinoma, von Hippel-Lindau disease, Zollinger-Ellison syndrome, anal cancer, cholangiocarcinoma, bladder cancer, ureteral carcinoma, glioma, neuroblastoma, meningioma, spinal cord tumor, osteochondroma, chondrosarcoma, Ewing's sarcoma, cancer of unknown primary site, carcinoid, fibrosarcoma, Paget's disease, cervix carcinoma, gallbladder cancer, eye cancer, Kaposi's sarcoma, prostate cancer, testicular cancer, cutaneous squamous cell carcinoma, mesothelioma, multiple myeloma, ovarian cancer, pancreatic endocrine tumor, glucagon tumor, pancreatic cancer , penile cancer, pituitary cancer, soft tissue sarcoma, retinoblastoma, small bowel cancer, gastric cancer, thymic cancer, trophoblastic carcinoma, hydatidiform mole, endometrial cancer, vaginal cancer, vulvar cancer, mycosis fungoides, insulinoma, heart cancer, meningeal cancer, peritoneal cancer, pleural cancer and blood cancer.
(57) A method for treating a tumor and/or cancer, comprising:
administering the first composition of the therapeutic agent of any one of (1) to (24) to a patient suffering from tumor and/or cancer; and
administering the second composition of the therapeutic agent of any one of (1) to (24) to the patient suffering from tumor and/or cancer.
(58) The method of (57), comprising the following steps in a sequential manner:
1) administering the first composition to the patient suffering from tumor and/or cancer; and
2) administering the second composition to the patient suffering from tumor and/or cancer after the administration of the first composition.
(59) The method of (57), wherein the tumor and/or cancer include: breast cancer, head and neck tumor, synovial cancer, kidney cancer, connective tissue cancer, melanoma, lung cancer, esophageal cancer, colon cancer, rectal cancer, brain cancer, liver cancer, bone cancer, choriocarcinoma, gastrinoma, pheochromocytoma, prolactinoma, von Hippel-Lindau disease, Zollinger-Ellison syndrome, anal cancer, cholangiocarcinoma, bladder cancer, ureteral carcinoma, glioma, neuroblastoma, meningioma, spinal cord tumor, osteochondroma, chondrosarcoma, Ewing's sarcoma, cancer of unknown primary site, carcinoid, fibrosarcoma, Paget's disease, cervix carcinoma, gallbladder cancer, eye cancer, Kaposi's sarcoma, prostate cancer, testicular cancer, cutaneous squamous cell carcinoma, mesothelioma, multiple myeloma, ovarian cancer, pancreatic endocrine tumor, glucagon tumor, pancreatic cancer , penile cancer, pituitary cancer, soft tissue sarcoma, retinoblastoma, small bowel cancer, gastric cancer, thymic cancer, trophoblastic carcinoma, hydatidiform mole, endometrial cancer, vaginal cancer, vulvar cancer, mycosis fungoides, insulinoma, heart cancer, meningeal cancer, peritoneal cancer, pleural cancer and blood cancer.

Compared with the prior art, the present invention has the following advantages and positive effects:

In order to improve the effect of CAR-modified immune cells in the treatment of tumors and widen the application of CAR-modified immune cells in the treatment of tumors, the present invention proposes a combined utilization of an exogenous labeling polypeptide to label the surface of tumor cells and/or cancer cells and CAR-modified immune cells that recognize the labeling polypeptide, so as to effectively solve the problems of the heterogeneity of the expression of tumor (especially solid tumors) antigen and evasion of tumor cells and/or cancer cells from immune surveillance, improves the recognition sensitivity of CAR-modified immune cells on tumor cells and/or cancer cells and effectively reduce the risk of targeting/off-target toxicity, thereby improving the efficacy of CAR-modified immune cells in killing tumor cells. When an oncolytic virus is used as a vector to mediate the expression of an exogenous labeling polypeptide in tumor cells, in addition of an oncolytic killing effect of the oncolytic virus, the CAR-modified cell targeting the labeling polypeptide can effectively eliminate residual tumor cells infected by the oncolytic virus. At the same time, since oncolytic viruses destroy the tumor microenvironment, the tumor homing ability of CAR-modified cells will be improved, which further enhance the effectiveness of the treatment for solid tumor.

Specifically, the present invention firstly designs the amino acid sequence of the labeling polypeptide having an extracellular antigen determining region, a spacer portion and a transmembrane portion and the nucleic acid with the coding sequence of the labeling polypeptide, so that the tumor cells and/or cancer cells can express the labeling polypeptide which will be finally modified on the surface of the tumor cells and/or cancer cells after the nucleic acid being transfected into tumor cells and/or cancer cells or after the tumor cells and/or cancer cells being infected by the recombinant virus upon the insertion of the nucleic acid into the viral genome. Since the amino acid sequence of the extracellular antigen determining region of the labeling polypeptide comprises one or more amino acid sequences of epitope polypeptide, the present invention effectively solves the problems of the expression heterogeneity of solid tumor antigen and the evasion of tumor from immune surveillance. The present invention also proposes the combination of an active ingredient includes or contains the nucleic acid encoding the labeling polypeptide and a CAR-modified immune cell that recognizes the extracellular antigen determining region (especially the epitope peptide), so as to improve recognition sensitivity of CAR-modified immune cells on tumor cells and further improve the ability of CAR-modified immune cells to kill tumor cells. Moreover, due to the fact that the amino acid sequence of the epitope polypeptide is not comprised in the amino acid sequence of the protein on cell membrane or secreted protein of mammal in the natural state, CAR-modified immune cells that recognizes the extracellular antigen determining region (especially the epitope peptide) of the exogenous labeling polypeptide will not recognize and kill other normal cells in the patient that are not modified with the exogenous labeling polypeptide. Therefore, the present invention greatly reduces the possible off-target toxicity of CAR-modified immune cells on patients.

Furthermore, the present invention introduces the nucleic acid coding the labeling polypeptide into tumor cells and/or cancer cells via oncolytic viruses, so that the oncolytic viruses can, at the same time of killing tumor cells and/or cancer cells, further reach a synergistic therapeutic effect achieved by combining above-mentioned significant enhancement of the expression of foreign epitope peptides on the surface of tumor cells and the effect of the CAR-modified immune cells. As the oncolytic virus destroys the tumor microenvironment, the tumor homing ability of CAR-modified immune cells is improved, thereby further enhancing the effectiveness of tumor (especially solid tumor) treatment. In addition, CAR-modified immune cells can also effectively eliminate those tumor cells that after being infected by oncolytic viruses, cannot complete the replication cycle and produce a sufficient number of progeny viruses and thus cannot be lysed; thereby achieving further synergistic effect. In addition, the antigens released by the tumor cells lysed by the oncolytic virus can further activate the body's own anti-tumor immunity, which can achieve better tumor killing effects than that of oncolytic viruses or CAR-modified immune cells used alone. Therefore, synergistic therapeutic effect is achieved.

The present invention provides a novel tumor treatment concept from the above conception, which has strong development prospect to become an effective anti-tumor biological drug.

Definitions

As used herein, the terms "tumor", "cancer", "tumor cell" and "cancer cell" cover the meanings generally recognized in the art.

As used herein, the term "oncolytic virus" refers to a virus that can replicate selectively in and lyse tumor cells.

As used herein, the term "therapeutically effective amount" or "therapeutically effective dose" refers to an amount of a functional agent or of a pharmaceutical composition useful for exhibiting a detectable therapeutic or inhibitory effect or invoking an antitumor response. The effect can be detected by any assay method known in the art.

As used herein, the term "administer" or "administration" refers to providing a compound, a composite or a composition (including viruses and cells) to a subject.

As used herein, the term "patient" refers to a human or non-human organism. Thus, the methods and compositions described herein are applicable to both human and veterinary diseases. In certain embodiments, the patient has a tumor. In some cases, the patient may suffer from one or more types of cancer simultaneously.

As used herein, the term "synergistic effect" refers to an effect arising between two or more agents that produce an effect greater than the sum of their individual effects.

As used herein, the term "pfu", or "plaque forming unit" refers to the number of viruses forming a plaque.

As used herein, the term "VP" refers to number of viral particles.

As used herein, the term "VP/kg" refers to number of viral particles per kilogram of patient's body weight.

As used herein, the term "TCID50" stands for median tissue culture infective dose and refers to the viral dose that leads to infection and causes a cytopathic effect in 50% of the tissue culture.

As used herein, the term "MOI", or "multiplicity of infection" refers to the ratio between the number of viruses and the number of cells, i.e., the number of virus particles used to initiate viral infection per cell. MOI=pfu/cell, that is, the number of cells×MOI=Total PFU.

BRIEF DESCRIPTION OF THE DRAWINGS

FIG. 5 shows the result of labeling tumor cells using electrotransfection technique and the expression of labeling polypeptides on the surface of tumor cells detected by flow cytometry in Preparation Example 1 of the present invention. FIGS. 5C-E show the results of TT3 labeled human ovarian cancer cell SKOV3-luc, human colorectal cancer cell HCT116-luc, and human liver cancer cell SK-HEP-1, respectively. The abscissas in the figures are the fluorescence intensity reading displayed by the flow cytometer, and the ordinates in the figures are the relative cell number.

DETAILED DESCRIPTION

Figure 1:
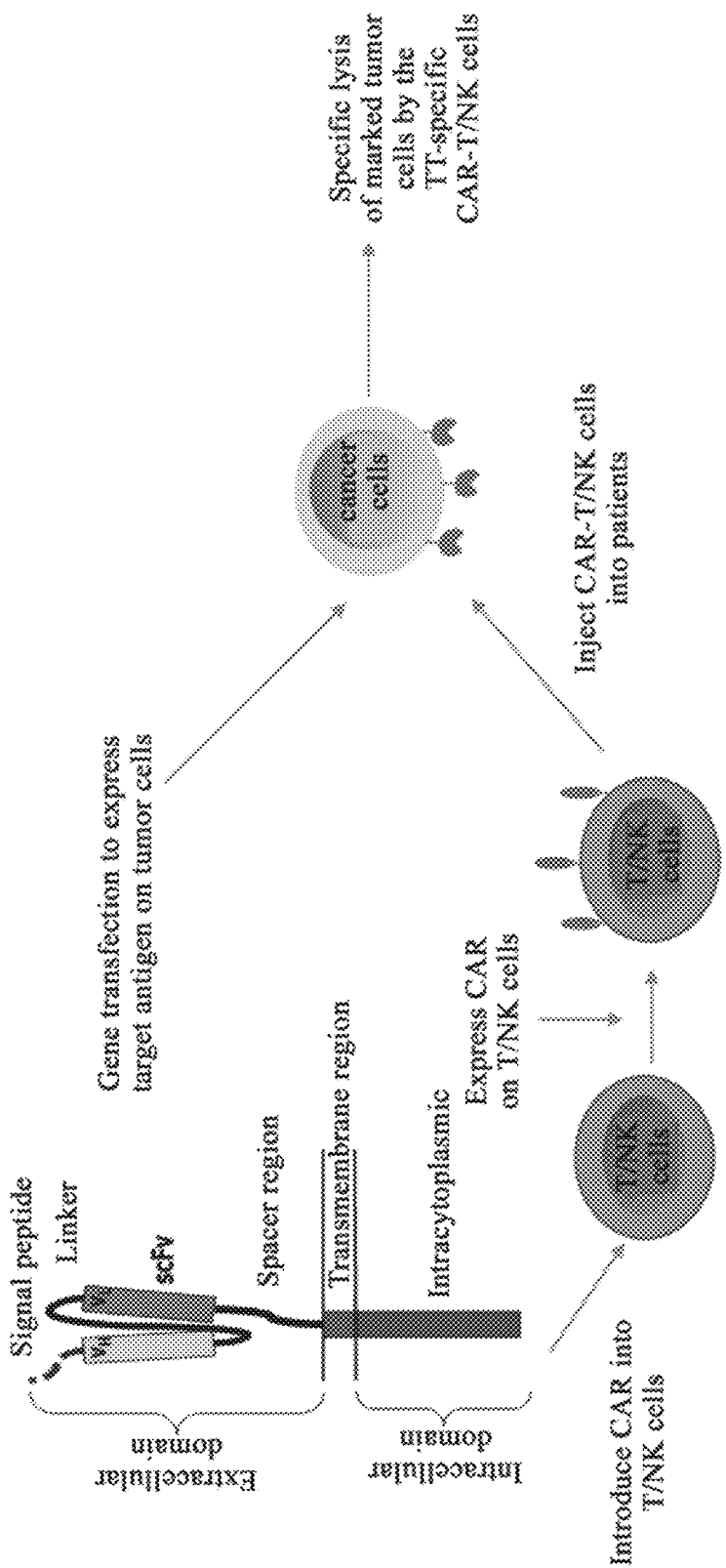
FIG. 1 is a schematic diagram showing one conception of the present invention.
Figure 2:
FIG. 2 is a schematic diagram showing the structure of a nucleic acid comprising a labeling polypeptide coding sequence in an embodiment of the present invention, which comprises a promoter, a signal peptide, an extracellular antigen determining region, a spacer portion and a transmembrane portion from the 5' end to 3' end.

The present disclosure is further explained with the following detailed description of preferred embodiments with references to the accompanying drawings, which is not to be taken in a limiting sense, and it will be apparent to those skilled in the art that various modifications or improvements can be made accordingly without departing from the spirit of the present disclosure and these are therefore within the scope of the present disclosure.

The present inventor was aware of the above-mentioned defects in the prior art and designed a labeling polypeptide through theoretical research and experimental verification. The labeling polypeptide can be expressed to form modification on the surface of the tumor cells and/or cancer cells and has an extracellular antigen determining region. The present invention also proposes a strategy that uses the labeling polypeptide to label the tumor cells and/or cancer cells and combines CAR-modified immune cells that recognize the labeling polypeptide, so as to effectively solve the problems of the expression heterogeneity of tumor (especially solid tumors) antigen and evasion of tumor cells and/or cancer cells from immune surveillance, improve the recognition sensitivity of CAR-modified immune cells on tumor cells and/or cancer cells and effectively reduce the risk of targeting/off-target toxicity, thereby improving the efficacy of CAR-modified immune cells in killing tumor cells.

Specifically, one aspect of the present invention provides a therapeutic agent for the treatment of tumors and/or cancers, comprising:
(a) a first composition, wherein the first composition comprises a first active ingredient in a first pharmaceutically acceptable carrier, and the first active ingredient includes or contains a nucleic acid having a labeling polypeptide coding sequence for being introduced into a tumor cell and/or a cancer cell; the labeling polypeptide has a extracellular antigen determining region, a spacer portion and a transmembrane portion that are operatively linked, which can be expressed to form modification on the surface of the tumor cell and/or cancer cell; the amino acid sequence of the extracellular antigen determining region comprises one or more amino acid sequences of epitope polypeptide; and wherein, in the natural state, the amino acid sequence of a protein on cell membrane or a secreted protein of mammal does not comprise the amino acid sequence of the epitope polypeptide; and
(b) a second composition, wherein the second composition comprises a second active ingredient in a second pharmaceutically acceptable carrier, and the second active ingredient comprises a chimeric antigen receptor-modified immune cell; the chimeric antigen receptor-modified immune cell can specifically recognize and bind to the extracellular antigen determining region of the labeling polypeptide.

The active ingredients in the therapeutic agent will be described in detail below.

Labeling Polypeptide

The present invention specifically designs the amino acid sequence of a labeling polypeptide which is used to modify the surface of tumor cells and/or cancer cells, wherein the labeling polypeptide has an extracellular antigen determining region, a spacer portion and a transmembrane portion that are operatively linked, and can be expressed to form modification on the surface of tumor cells and/or cancer cells; the amino acid sequence of the extracellular antigen determining region comprises one or more amino acid sequences of epitope polypeptide; wherein, in the natural state, the amino acid sequence of proteins on cell membrane or secreted proteins of mammal do not comprise the amino acid sequence of the epitope polypeptide.

The term "extracellular antigen determining region" as used herein refers to the part of the labeling polypeptide that is located outside the cell membrane and contains the epitope polypeptide when it is expressed on the cell surface.

Preferably, the amino acid sequence of the epitope polypeptide is derived from the amino acid sequence of a protein that exists in the nature, or is an artificially synthesized amino acid sequence that does not exists in the nature. The proteins that exist in the nature include mammalian intracellular proteins and proteins of organisms other than mammals. Proteins of organisms other than mammals include viral proteins, bacterial proteins, fungal proteins, protozoan proteins, plant proteins, and proteins of other animals except for mammals.

In some embodiments of the present invention, the amino acid sequences of the epitope polypeptides are derived from the amino acid sequences of the following tags: Myc tag, HA tag, Strep tag II, Flag tag, HAT tag, S tag, S1 tag, Protein C tag, tag-100 tag, E2 tag, TAP tag, HSV tag, KT3 tag, V5 tag, VSV-G tag, His tag or RFP tag, etc.

The amino acid sequences and nucleotide sequences of the above tags are known and available from public databases commonly used in the art.

In a preferred embodiment of the present invention, the amino acid sequences of the epitope polypeptides are derived from the amino acid sequences of the following tags: human Myc tag (corresponding labeling polypeptide is denoted as TT1), influenza virus HA tag (corresponding labeling polypeptide is denoted as TT2), Strep tag II (corresponding labeling polypeptide is denoted as TT3). Further preferably, the amino acid sequence of the epitope polypeptide is consistent with the amino acid sequence of position 410 to 419 of the human Myc protein; or the amino acid sequence of the epitope polypeptide is consistent with the amino acid sequence of position 119 to 127 of the influenza virus HA protein, or the amino acid sequence of the epitope polypeptide is consistent with Strep tag II (for the detailed description of Strep tag II, see the document "Molecular Interaction Between the Strep-tag Affinity Peptide and its Cognate Target, Streptavidin, Thomas G. M. Schmidt, Jurgen Koepke, Ronald Frank and Arne Skerra"). In other embodiments of the present invention, the amino acid sequences of the epitope polypeptides of TT1 and TT2 can extend to upstream and downstream of the above sequence by no more than 10 amino acids, wherein, the amino acid sequence of the human Myc protein can be the amino acid sequence numbered P01106 isoform1 in UniProtKB, and the amino acid sequence of the influenza virus HA protein can be the amino acid sequence numbered Q03909 in UniProtKB.

In a particular embodiment, the amino acid sequence of the extracellular antigen determining region of the labeling polypeptide comprises one or more amino acid sequences of the epitope polypeptide, wherein, when the amino acid sequence of the extracellular antigen determining region of the labeling peptide comprises a plurality of amino acid sequences of the epitope polypeptides, every two adjacent epitope polypeptides are operatively linked. For example, they may be connected by a linker or be connected directly without any linker. The amino acid sequence of the linker may be, for example, G (as used in labeling polypeptides C1&2a, C1&2b), GGS (as used in C1&2a, C1&2b), GGGGSGGGGS (as used in TT1-TT3).

In order to enhance the immunogenicity of the labeling polypeptide, the extracellular antigen determining region of the labeling polypeptide preferably comprises n epitope polypeptides, where n is an integer greater than or equal to 1, for example, n=1, 2, 3, 4 . . . etc. Preferably, n is an integer of 1-10; it is also preferable that n is an integer of 2-5; and it is also preferable that n=2 or 3. For example, the extracellular antigen determining region of the labeling polypeptide may comprise 3 repeated epitope polypeptides derived from the Myc tag (see, for example, TT1), or comprise 3 repeated epitope polypeptides derived from the HA tag (see, for example, TT2), or comprise 3 repeated epitope polypeptides derived from the Strep tag II (see, for example, TT3), or comprise 3 repeated epitope polypeptides derived from the Myc tag and 3 repeated epitope polypeptides derived from the HA tag (see, for example, C1&2a), or comprise 2 repeated epitope polypeptides derived from the Myc tag and 2 repeated epitope polypeptides derived from HA Tag (see, for example, C1&2b).

In one embodiment of the present invention, the amino acid sequences of the extracellular antigen determining regions are shown as SEQ ID NO: 1 (corresponding to TT1), SEQ ID NO: 2 (corresponding to TT2), SEQ ID NO: 3 (corresponding to TT3), SEQ ID NO: 4 (corresponding to C1&2a) and SEQ ID NO: 5 (corresponding to C1&2b).

Preferably, the transmembrane portion is derived from the transmembrane region of CD8, CD3ζ, CD4 or CD28 whose full-length amino acid sequence and nucleotide sequence are known and available from public databases commonly used in the art. More preferably, the transmembrane portion is derived from the transmembrane region of human CD8α. Still more preferably, the amino acid sequence of the transmembrane portion comprises the amino acid sequence as shown in SEQ ID NO: 7. CD8 is a transmembrane glycosylated membrane protein composed of α and β subunits. It works with T cell surface receptor to make T cell to bind to specific antigen. CD8 specifically binds to MHC I and mediates the killing effect of cytotoxic T cells. The transmembrane region is usually a hydrophobic alpha helix that spans the cell membrane.

In the labeling polypeptide of the present invention, the transmembrane portion and the extracellular antigen determining region can be connected by a spacer portion. The structure of this region should be flexible, so that the extracellular antigen determining region can be adapted to different directions to promote the recognition and binding of corresponding CAR. The simplest form of the spacer portion is the hinge region of immunoglobulin IgGI, and can also be a portion of immunoglobulin $C_{H2}C_{H3}$ region. The present invention has found through researches and experimentations that the spacer portion is preferably derived from the hinge region of CD8α and the transmembrane portion is preferably derived from the transmembrane region of CD8α. Preferably, the amino acid sequence of the spacer portion is as shown in SEQ ID NO: 6. More preferably, the spacer portion and the transmembrane portion constitute a spacer transmembrane portion, and the amino acid sequence of the spacer transmembrane portion is consistent with the amino acid sequences of position Y to 210 of CD8α, and 118≤Y ≤128, Y is an integer. Wherein, the UniProtKB number of the amino acid sequence of CD8α can be P01732. That is to say, the amino acid sequence of the spacer transmembrane portion is preferably selected from position 118 to 210 of CD8α and comprises the amino acids at position 128 to 210. For example, the amino acid sequence of the spacer transmembrane portion is shown as any one of the amino acid sequences selected from the following group:

position 118 to 210, position 119 to 210, position 120 to 210, position 121 to 210, position 122 to 210, position 123 to 210, position 124 to 210, position 125 to 210, position 126 to 210, position 127 to 210, or position 128 to 210 of CD8α.

The terms "spacer portion" and "transmembrane portion" used herein are known in the art. For details, please refer to "'Immunology introductory theory', Yu Shanqian, Higher Education Press, 2008"; and "'Immunobiology', Seventh edition, Kenneth Murphy, Paul Travers, Mark Walport, etc.".

In the nucleic acid having the labeling polypeptide coding sequence of the present invention, a signal peptide coding sequence is preferably comprised before the 5' end of the labeling polypeptide coding sequence, and the signal peptide has the function of guiding the secretion of the target protein to the cell surface. The present invention found that the combination of the extracellular antigen determining region with the signal peptide from the GM-CSFα chain allow the labeling polypeptide to be expressed on the surface of tumor cells. The GM-CSFα chain signal peptide is the leader sequence for targeting the labeling polypeptide of the present invention to the secretory pathway, the coding sequence of which is first translated into protein in the cell together with the coding sequence of the labeling polypeptide and guide the synthesized protein into intracellular secretion pathway. The signal peptide is removed before the labeling polypeptide is expressed on the cell surface. The full-length amino acid sequence and nucleotide sequence of the GM-CSFα chain are known and available from public databases commonly used in the art. Preferably, the amino acid sequence of the signal peptide is selected from position 1 to 22 of human GM-CSFα chain. More preferably, the amino acid sequence of the signal peptide is as shown in SEQ ID NO: 8. Wherein, the amino acid sequence of GM-CSFα chain is derived from UniProtKB-P15509.

In a specific embodiment of the present invention, the labeling polypeptide comprises the following amino acid sequences that are orderly and operatively linked: an extracellular antigen determining region (which comprises one or more amino acid sequences of the epitope polypeptide), spacer portion and transmembrane portion. In a more specific embodiment of the present invention, the amino acid sequence of the epitope polypeptide of the extracellular antigen determining region is derived from the amino acid sequence of the epitope polypeptide of the following peptide: Myc tag derived from the human intracellular protein Myc, HA tag derived from the HA protein of influenza virus, the artificially synthesized sequence Strep tag II that does not exists in the nature. The spacer portion is derived from the hinge region of human CD8α, and the transmembrane portion is derived from the transmembrane region of human CD8α.

As mentioned above, the signal peptide is operatively linked with the extracellular antigen determining region, the extracellular antigen determining region is operatively linked with the spacer portion and the spacer portion is operatively linked with the transmembrane portion. For example, they may connect by a linker or connected directly without any linker. In an embodiment of the present invention, the signal peptide and the extracellular antigen determining region are connected by a linker, such as GAHADITS (as used in TT1-TT3), GAHAAQLTLTKGNK (as used in C1&2a), GAHA (as used in C1&2b). The extracellular antigen determining region and the spacer portion are connected by a linker, such as, -Ala-Ser- and G, and the spacer portion and the transmembrane portion are connected directly without a linker.

The present invention further found that the labeling polypeptide can express two epitope polypeptides at the same time. Specifically, the present invention designed the labeling polypeptide C1&2a and its antigen determining region contains three repeats of Myc tag and three repeats of HA tag. The present invention also designed a labeling polypeptide C1&2b, the antigen determining region of which contains two repeats of Myc tag and two repeats of HA tag. In order to further stabilize the expression of the labeling polypeptide on the cell membrane surface, a TIGIT spacer was added to the spacer portion of C1&2b. The amino acid sequence of the added spacer is consistent with the amino acid sequence of position 24 to 140 of TIGIT. Wherein, the amino acid sequence of TIGIT is derived from UniProtKB-Q495A1. More preferably, the amino acid sequence of the added TIGIT spacer is as shown in SEQ ID NO: 9 and the amino acid sequence of the C1&2b spacer transmembrane portion is as shown in SEQ ID NO: 10.

Preferably, the amino acid sequence of the labeling polypeptide is as shown in SEQ ID NO: 11 (corresponding to TT1), SEQ ID NO: 12 (corresponding to TT2), SEQ ID NO: 13 (corresponding to TT3), SEQ ID NO: 14 (corresponding to C1&2a) or SEQ ID NO: 15 (corresponding to C1&2b).

```
SEQ ID NO: 11:
GAHADITSEQKLISEEDLGGGGSGGGGSEQKLISEEDLGGGGSGGGGSEQKLISEEDLGG

GGSGGGGSASFVPVFLPAKPTTTPAPRPPTPAPTIASQPLSLRPEACRPAAGGAVHTRGLDF

ACDIYIWAPLAGTCGVLLLSLVITLYCNHRN
``` wherein, the boldface shows the epitope polypeptide, the gray portion shows the spacer 10 portion from the CD8 hinge region, and the underline shows the transmembrane portion from the CD8 transmembrane region.

```
SEQ ID NO: 12:
GAHADITSYPYDVPDYAGGGGSGGGGSYPYDVPDYAGGGGSGGGGSYPYDVPDYAGGG

GSGGGGSASFVPVFLPAKPTTTPAPRPPTPAPTIASQPLSLRPEACRPAAGGAVHTRGLDFA

CDIYIWAPLAGTCGVLLLSLVITLYCNHRN
``` wherein, the boldface shows the epitope polypeptide, the gray shows the spacer portion from the CD8 hinge region, and the underline shows the transmembrane portion from the CD8 transmembrane region.

```
SEQ ID NO: 13:
GAHADITSNWSHPQFEKGGGGSGGGGSNWSHPQFEKGGGGSGGGGSNWSHPQFEKGG

GGSGGGGSASFVPVFLPAKPTTTPAPRPPTPAPTIASQPLSLRPEACRPAAGGAVHTRGLDF

ACDIYIWAPLAGTCGVLLLSLVITLYCNHRN
``` wherein, the boldface shows the epitope polypeptide, the gray shows the spacer portion from the CD8 hinge region, and the underline shows the transmembrane portion from the CD8 25 transmembrane region.

SEQ ID NO: 14:
GAHAAQLTLTKGNKEQKLISEEDLGEQKLISEEDLGEQKLISEEDLGGSYPYDVPDYAGYPY

DVPDYAGYPYDVPDYAASFVPVFLPAKPTTTPAPRPPTPAPTIASQPLSLRPEACRPAAGGAV

HTRGLDFACDIYIWAPLAGTCGVLLLSLVITLYCNHRN wherein, the boldface shows the epitope polypeptide, the gray shows the spacer portion from the CD8 hinge region, and the underline shows the transmembrane portion from the CD8 transmembrane region.

SEQ ID NO: 15:
GAHAEQKLISEEDLGEQKLISEEDLGGSYPYDVPDYAGYPYDVPDYAGTGTIETTGNISAEK

GGSIILQCHLSSTTAQVTQVNWEQQDQLLAICNADLGWHISPSFKDRVAPGPGLGLTLQSLTV

NDTGEYFCIYHTYPDGTYTGRIFLEVLESSVAEHGARFQIASFVPVFLPAKPTTTPAPRPPTPA

PTIASQPLSLRPEACRPAAGGAVHTRGLDFACDIYIWAPLAGTCGVLLLSLVITLYCNHRN wherein, the boldface shows the epitope polypeptide, the dark gray shows the part from the TIGIT spacer in the spacer portion, the light gray shows the part from the CD8 hinge region in the spacer portion, and the underline shows the transmembrane portion from the CD8 transmembrane region.

Nucleic Acid Having Labeling Polypeptide Coding Sequence

The labeling polypeptide coding sequence comprises an extracellular antigen determining region coding sequence, a spacer portion coding sequence and a transmembrane portion coding sequence, the extracellular antigen determining region coding sequence encodes the extracellular antigen determining region of the labeling polypeptide, the spacer portion coding sequence encodes the spacer portion of the labeling polypeptide and the transmembrane portion coding sequence encodes the transmembrane portion of the labeling polypeptide. The extracellular antigen determining region coding sequence comprises one or more coding sequences of epitope polypeptides; wherein, in natural state, the coding sequence of a protein on cell membrane or a secreted protein of mammalian does not comprise the coding sequence of the epitope polypeptide.

In some embodiments of the present invention, the epitope polypeptide coding sequence is derived from the coding sequences of the following tags: Myc tag, HA tag, Strep tag II, Flag tag, HAT tag, S tag, S1 tag, protein C tag, Tag-100 tag, E2 tag, TAP tag, HSV tag, KT3 tag, V5 tags, VSV-G tag, His tag or RFP tag, etc.

Preferably, the epitope polypeptide coding sequence is derived from the coding sequences of the following tags: the coding sequence of Myc tag, the coding sequence of HA tag, and the coding sequence of Strep tag II.

In a specific embodiment, the coding sequence of the extracellular antigen determining region of the labeling polypeptide comprises one or more coding sequences of the epitope polypeptide, wherein when the coding sequence of the extracellular antigen determining region of the labeling polypeptide comprise a plurality of coding sequences of the epitope polypeptide, every two adjacent coding sequences of the epitope polypeptide are operatively linked. For example, they may be connected by a linker coding sequence or be connected directly without any linker coding sequence.

As mentioned above, in order to enhance the immunogenicity of the labeling polypeptide, the extracellular antigen determining region of the labeling polypeptide preferably comprises n epitope polypeptides, where n is an integer greater than or equal to 1, for example, n=1, 2, 3, 4, etc. Preferably, n is an integer of 1-10; it is also preferable that n is an integer of 2-5; and it is also preferable that n=2 or 3. For example, the extracellular antigen determining region of the labeling polypeptide may include three repeated epitope polypeptides derived from human Myc protein, or two repeated epitope polypeptides derived from influenza virus HA protein. Therefore, the coding sequence of the extracellular antigen determining region of the labeling polypeptide preferably comprises 3 repeats or 2 repeats of the coding sequence of the epitope polypeptide correspondingly.

In a preferred embodiment of the present invention, the nucleotide sequence of the coding sequence of the extracellular antigen determining region is as shown in SEQ ID NO: 16 (corresponding to TT1), SEQ ID NO: 17 (corresponding to TT2), SEQ ID NO: 18 (corresponding to TT3), SEQ ID NO: 19 (corresponding to C1&2a) or SEQ ID NO: 20 (corresponding to C1&2b).

Preferably, the transmembrane portion coding sequence is derived from the coding sequence of the transmembrane region of CD8, CD3ζ, CD4 or CD28. More preferably, the transmembrane portion coding sequence is derived from the coding sequence of the transmembrane region of human CD8α. Still more preferably, the nucleotide sequence of the coding sequence of the transmembrane portion comprises the nucleotide sequence as shown in SEQ ID NO:21.

In the labeling polypeptide coding sequence, the transmembrane portion coding sequence and the extracellular antigen determining region coding sequence may be connected by the spacer portion coding sequence. The simplest form of the spacer portion is the hinge region of immunoglobulin IgGI, and it can also be a portion of $C_{H2}C_{H3}$ region of immunoglobulin. The present invention found through researches and experimentations that the coding sequence of the spacer portion is preferably derived from the coding sequence of the hinge region of CD8α, and the coding sequence of the transmembrane portion is preferably derived from the coding sequence of the transmembrane region of CD8α. Preferably, the nucleotide sequence of the coding sequence of the spacer portion is as shown in SEQ ID NO: 22. More preferably, the coding sequence of the spacer portion and the coding sequence of the transmembrane region portion constitute the coding sequence of the spacer transmembrane portion, and the spacer portion and the transmembrane portion may be connected directly without a linker.

In the nucleic acid having the labeling polypeptide coding sequence of the present invention, a signal peptide coding sequence is preferably comprised before the 5' end of the labeling polypeptide coding sequence and the signal peptide coding sequence encodes the signal peptide. The signal peptide has the function of guiding the secretion of the target protein to the cell surface, which is the leader sequence for targeting the labeling polypeptide of the present invention to the secretory pathway. The coding sequence thereof is first translated into a protein in the cell together with the coding sequence of the labeling polypeptide to guide the synthesized protein enter into the intracellular secretory pathway. The signal peptide is removed before the labeling polypeptide is expressed on the cell surface.

Preferably, the nucleotide sequence of the signal peptide coding sequence is derived from the signal peptide coding sequence of human GM-CSFα chain. More preferably, the nucleotide sequence of the signal peptide coding sequence is as shown in SEQ ID NO: 23.

In a specific embodiment of the present invention, the nucleic acid having the labeling polypeptide coding sequence comprises the following coding sequences operatively and orderly linked: a signal peptide coding sequence, an extracellular antigen determining region coding sequence (which comprises one or more the coding sequence(s) of the epitope polypeptide(s)), the spacer portion coding sequence and the transmembrane portion coding sequence. In a more specific embodiment of the present invention, the coding sequence of the epitope polypeptide of the extracellular antigen determining region is derived from the coding sequence of the following tags: Myc tag, HA tag or Strep tag II; the signal peptide coding sequence is derived from the coding sequence of the signal peptide of human GM-CSFα chain; the spacer portion coding sequence is derived from the coding sequence of the hinge region of human CD8α, and the transmembrane portion coding sequence is derived from the coding sequence of the transmembrane region of human CD8α.

As mentioned above, the signal peptide coding sequence and the extracellular antigen determining region coding sequence, the extracellular antigen determining region coding sequence and the spacer portion coding sequence, the spacer portion coding sequence and the transmembrane portion coding sequence are operatively linked, for example, they may be connected by a linker coding sequence or be connected directly without any linker coding sequence. In one embodiment of the present invention, the signal peptide coding sequence and the extracellular antigen determining region coding sequence are connected by a linker coding sequence, such as GGCGCGCATGCCGACATTACTAGT (as used in any one of the nucleic acids having the TT1-TT3 coding sequence, respectively), GGCGCG-CATGCCGCTCAGTTGACAT-TGACGAAGGGCAATAAA (as used in the nucleic acid having C1&2a coding sequence), GGCGCGCATGCC (as used in the nucleic acid having C1&2b coding sequence). The extracellular antigen determining region coding sequence and the spacer portion coding sequence are connected by a linker coding sequence, such as GCTAGC, GGG. The spacer portion coding sequence and the transmembrane portion coding sequence are connected directly without a linker coding sequence.

Preferably, a TIGIT spacer region coding sequence is added to the C1&2b spacer portion coding sequence, wherein the TIGIT spacer region coding sequence encodes the amino acid of position 24 to 140 of TIGIT, wherein, the amino acid sequence of TIGIT is derived from UniProtKB-Q495A1. Preferably, the TIGIT spacer region coding sequence comprises the nucleotide sequence as shown in SEQ ID NO: 24. Preferably, the coding sequence of the spacer transmembrane portion of C1&2b comprises the nucleotide sequence as shown in SEQ ID NO:25.

Preferably, the nucleotide sequence of the nucleic acid having the labeling polypeptide coding sequence is as shown in SEQ ID NO: 26 (corresponding to TT1), SEQ ID NO: 27 (corresponding to TT2), SEQ ID NO: 28 (corresponding to TT3), SEQ ID NO: 29 (corresponding to C1&2a) or SEQ ID NO: 30 (corresponding to C1&2b).

Preferably, the nucleic acid having the labeling polypeptide coding sequence includes DNA or RNA; and the RNA includes mRNA transcribed from the DNA.

Preferably, the nucleic acid comprises in sequence an operatively linked promoter and the labeling polypeptide coding sequence. Examples of the promoter include any promoters known in the art for promoting the transcription of downstream DNA sequence, such as CMV promoter, T7 promoter and the like.

Recombinant Virus

In one embodiment of the present invention, the first active ingredient is a recombinant virus and the genome thereof has a promoter, a signal peptide coding sequence and the labeling polypeptide coding sequence that are orderly and operatively linked; wherein the recombinant virus includes replication-selective recombinant oncolytic virus or replication-deficient recombinant virus.

Preferably, the recombinant oncolytic virus is derived from a genetically mutated virus with oncolytic effect and a wild-type virus with oncolytic effect; preferably, the recombinant oncolytic virus is derived from an adenovirus, poxvirus, herpes simplex virus, measles virus, Semliki forest virus, vesicular stomatitis virus, polio virus, retrovirus, reovirus, Seneca valley virus, Echo-type enterovirus, Coxsackie virus, Newcastle disease virus and Malaba virus with oncolytic effect.

Oncolytic virus therapy has a long history. Many types of viruses have been modified for oncolytic virus development, including adenovirus, herpes virus, poxvirus, picornavirus, paramyxovirus, reovirus, parvovirus and rhabdovirus. Up to now, two oncolytic viruses (H101 and T-VEC) have been approved for clinical tumor treatment. Oncolytic viruses are artificially modified viruses whose pathogenic genes have been knocked out and are basically unable to replicate in normal tissue cells, but can selectively replicate in tumor cells to exert oncolytic effects. Take vaccinia virus as an example, oncolytic vaccinia virus is generally constructed by knocking out the endogenous thymidine kinase (TK) gene of vaccinia virus or double knocking out TK and vaccinia growth factor (VGF) genes using homologous recombination technique by means of genetic bioengineering. TK is one of the key enzymes in DNA synthesis. Vaccinia virus needs to use TK to form a high-concentration nucleic acid pool during the replication process to complete the smooth replication of progeny virus. Vaccinia virus often promotes the proliferation of the host and surrounding cells through VGF gene products, and achieves their own replication and proliferation, while the damage to normal cells of the vaccinia virus without the VGF gene is greatly reduced. Due to the deletion of TK and VGF genes, the ability of the virus to replicate in normal cells is restricted and the expression of exogenous gene inserted into oncolytic virus vectors will also be greatly restricted. However, TK gene is highly expressed in most of the environment of tumor cells, which provides a favorable environment for the replication and packaging of vaccinia viruses, so that vaccinia viruses have the functions of selectively replicating and oncolytic in tumor cells and allow the exogenous gene inserted into the tumor virus vector to be highly expressed, In addition to the direct oncolytic effect, oncolytic viruses can also make tumor cells release holographic tumor antigens to activate the inherent anti-tumor immunity of the body and at the same time have a certain regulatory effect on the tumor microenvironment.

In the present invention, the labeling polypeptide coding sequence is inserted into the genome of the oncolytic virus, thereby introducing the labeling polypeptide coding nucleic acid into tumor cells and/or cancer cells, so that the oncolytic virus can kill tumor cells and/or cancer cells and at the same time the expression of exogenous epitope peptide on the surface of tumor cells is combined with the effect of CAR-modified immune cells to achieve a synergistic therapeutic effect. As the oncolytic virus destroys the tumor microenvironment, the tumor homing ability of CAR-modified immune cells is improved, thereby further enhancing the effectiveness of solid tumor treatment. In addition, CAR-modified immune cells can also effectively eliminate those tumor cells that after being infected by oncolytic viruses, cannot complete the replication cycle and produce a sufficient number of progeny viruses and thus cannot be lysed; thereby achieving further synergistic effect. In addition, the antigens released by the tumor cells lysed by the oncolytic virus can further activate the body's own anti-tumor immunity, which can achieve better tumor killing effects than using oncolytic viruses or CAR-modified immune cells alone, thereby achieving synergistic therapeutic effect.

In one embodiment of the present invention, a nucleic acid (the nucleotide sequence of which may be, for example, any one of SEQ ID NOs: 26 -30) having the labeling polypeptide coding sequence is inserted into the genome of the obtained replication-selective recombinant oncolytic vaccinia virus.

Preferably, the recombinant oncolytic virus is a recombinant oncolytic vaccinia virus that is functionally defective in the TK gene and the VGF gene. The TK gene can be functionally defective by inserting exogenous nucleotide sequences. The VGF gene can be functionally defective by gene knockout or inserting exogenous nucleotide sequences, but it is preferable to knock out the VGF gene.

The term "functional defect" or "functionally defective" used herein when referring to the gene of an oncolytic virus means that the oncolytic virus is unable to exert the function that the gene should have, that is, the function is lost. This purpose can be achieved by, for example, inserting extraneous fragment into the gene or knocking out the gene.

More preferably, the recombinant oncolytic vaccinia virus is Wyeth strain or WR strain.

The labeling polypeptide coding sequence can be inserted into the TK gene to obtain the recombinant oncolytic virus of the present invention. The labeling polypeptide coding sequence can also be inserted into the VGF gene to obtain the recombinant oncolytic virus of the present invention.

In a preferred embodiment, the recombinant oncolytic vaccinia virus is obtained by genetically modifying the VSC20 vaccinia virus which is a vaccinia virus with the VGF gene deleted. For preparation methods, please refer to the scientific literature: "McCart, JA, et al. Systemic cancer therapy with a tumor-selective vaccinia virus mutant lacking thymidine kinase and vaccinia growth factor genes. Cancer Res (2001) 61: 8751-8757". The genetic modification includes inserting an exogenous labeling polypeptide coding sequence into the TK gene of the VSC20 vaccinia virus to make the TK gene functionally defective.

The genome of the recombinant virus may also integrate other exogenous genes, such as exogenous screening gene which includes puromycin gene, gpt gene and/or LacZ gene. The exogenous screening gene can be knocked out by a gene knockout system (for example, LoxP) when purifying the gene encoding the exogenous labeling polypeptide.

In some embodiments, the present invention adopts the vaccinia virus early/late promoter p7.5 to control the exogenous screening gene, artificially synthesizes the vaccinia virus early promoter pSEL to control signal peptide sequence and the exogenous labeling polypeptide coding sequence, and inserts the exogenous screening gene coding sequence, the signal peptide coding sequence and the labeling polypeptide coding sequence into the TK gene region of the vaccinia virus VSC20 strain through in vitro intracellular recombination technique to construct an oncolytic virus. The two promoters respectively initiate the expression of the genes that they respectively regulate in a back-to-back manner.

In another embodiment of the present invention, Crisper-Cas9 gene editing technique is used to construct a recombinant oncolytic vaccinia virus.

Preferably, the Crisper-Cas9 gene editing method can perform cutting and homologous recombination at two sites simultaneously so as to achieve the purpose of knocking out a sequence and inserting a transgene at one time.

Preferably, the Crisper-Cas9 gene editing method can cut the target sequence and the donor sequence simultaneously to improve the efficiency of homologous recombination.

Figure 3:
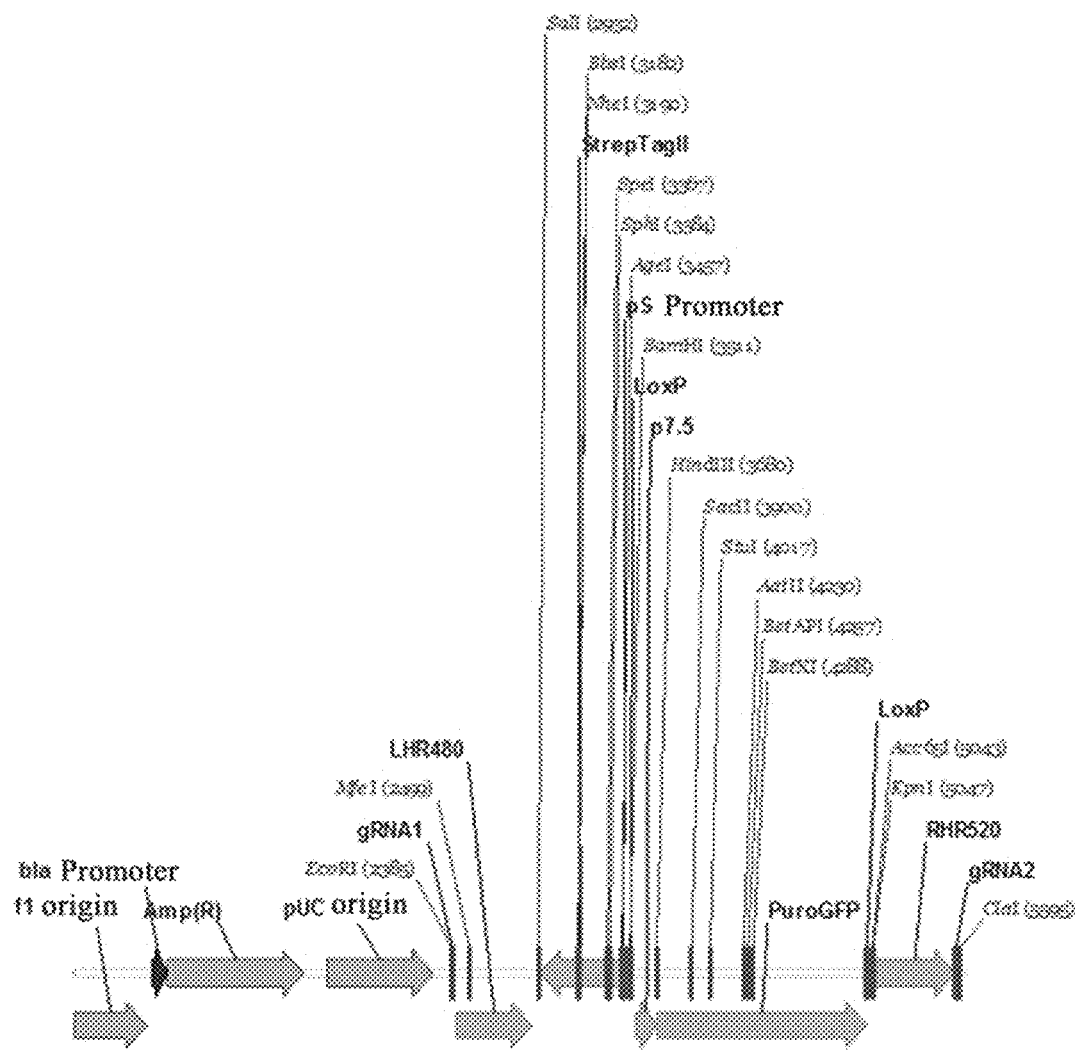
FIG. 3 is a schematic diagram of the structure of the donor plasmid when using Crisper Cas9 technology to prepare recombinant oncolytic vaccinia virus in an embodiment of the present invention. From left side to right side are bla promoter, ampicillin resistance gene, pUC initiation site, splice site of leader RNA-1 (gRNA1), left homology arm (LHR480), labeling polypeptide TT3 coding sequence, signal peptide coding sequence (not shown), pS promoter, LoxP site, p7.5 promoter, PuroGFP Coding sequence, LoxP site, right homology arm (RHR520), and splice site of leader RNA-2 (gRNA2).
Figure 4:
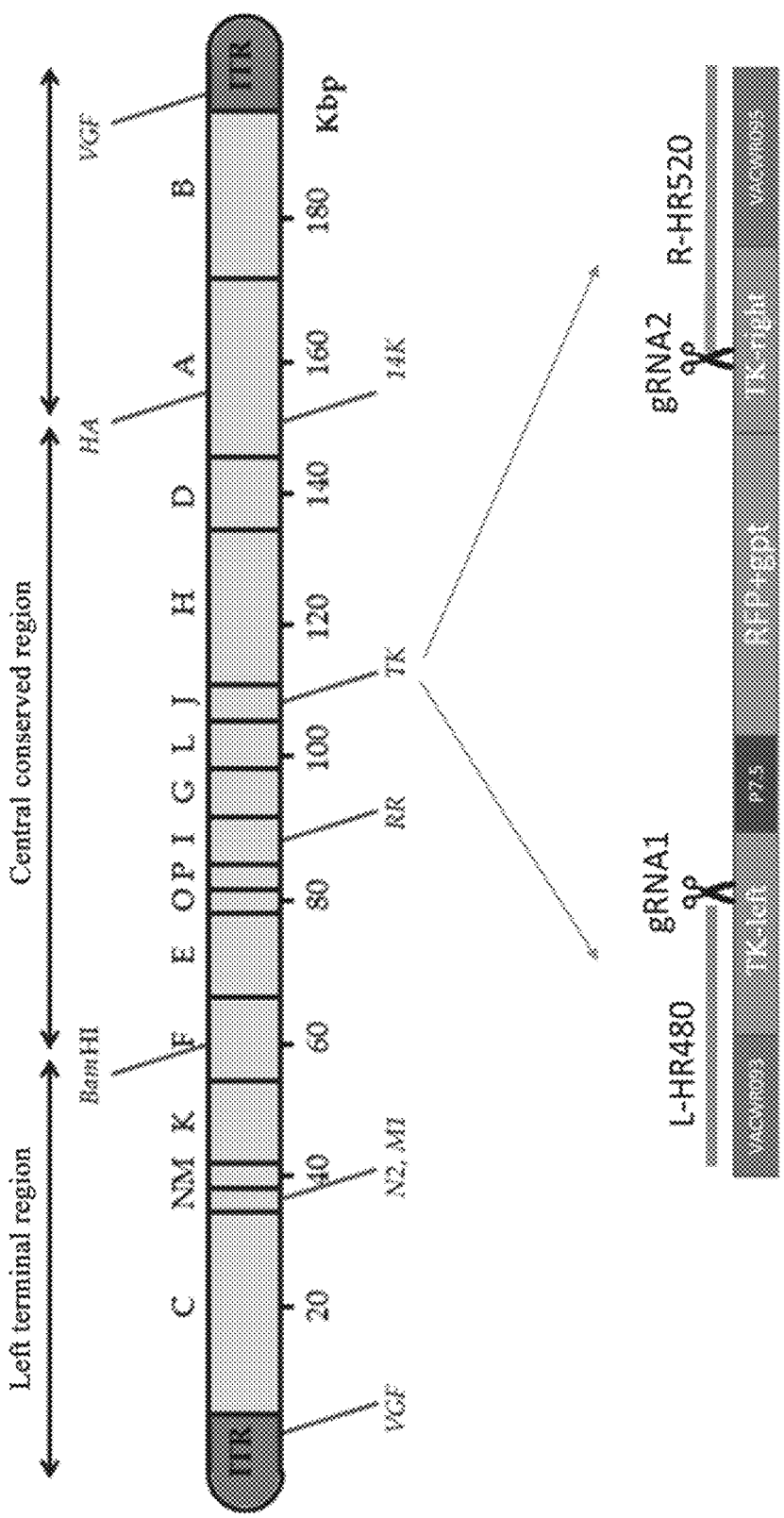
FIG. 4 is a schematic diagram of Crisper Cas9 cutting the TK site of the DDVV-RFP oncolytic vaccinia virus genome in an embodiment of the present invention. The upper FIG. represents the DDVV-RFP oncolytic vaccinia virus genome, and the lower figure schematically shows the cutting on the left portion and right portion of the TK gene mediated by two leader RNAs.
Figure 5A:
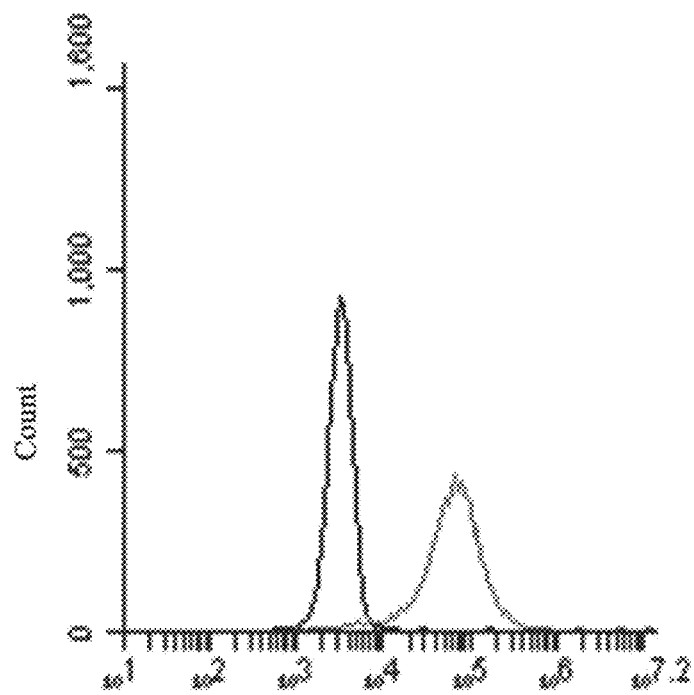
FIGS. 5A and 5B show the results of Jurkat immortalized T lymphocytes labeled with TT1 and TT2, respectively.
Figure 5B:
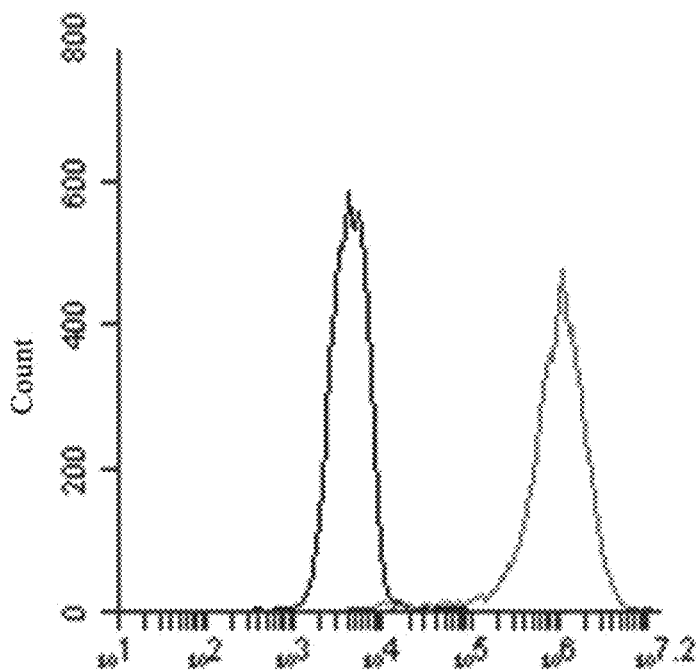
Figure 5C:
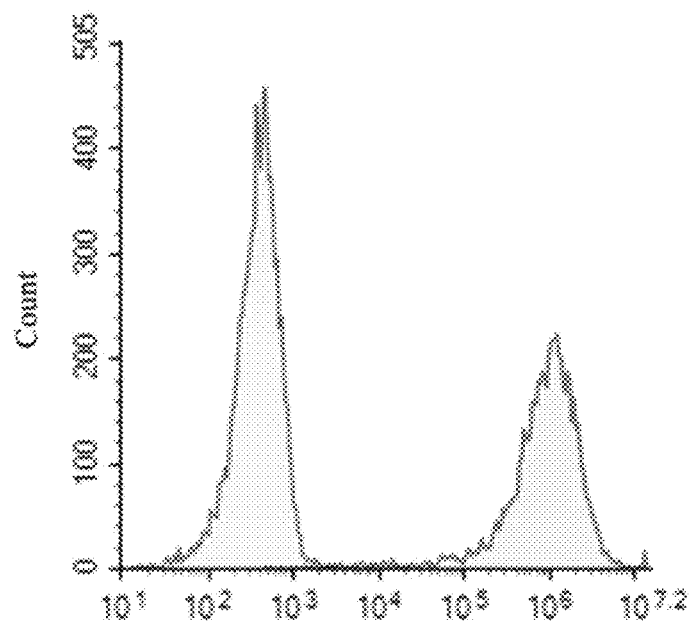
Figure 5D:
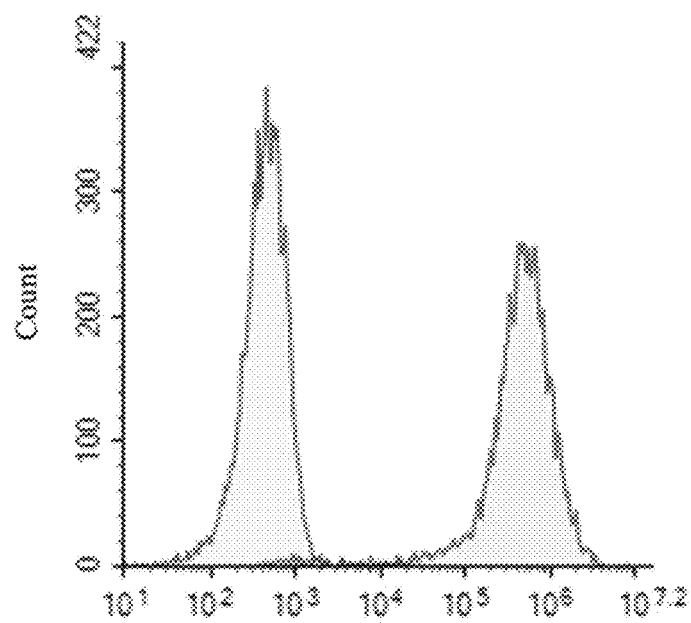
Figure 5B:
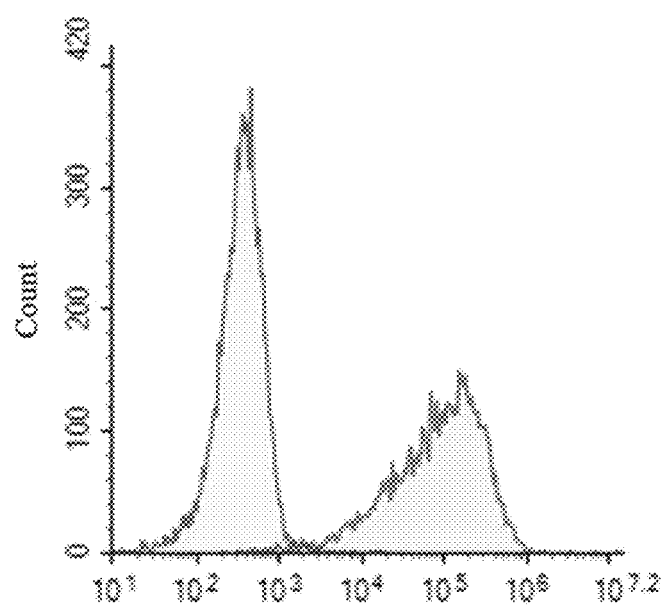

The design of cutting and homologous recombination of the Crisper-Cas9 gene editing method of the present invention is shown in FIG. 3 and FIG. 4.

Specifically, the Crisper-Cas9 system may include leader RNA and donor DNA.

Preferably, the leader RNAs includes leader RNA-1 and leader RNA-2. The nucleotide sequence of the leader RNA-1 is preferably consistent with the nucleotide sequence at position 123 to 145 of the vaccinia virus TK gene, and the nucleotide sequence of the leader RNA-2 is preferably consistent with nucleotide sequence at position 411 to 433 of the vaccinia virus TK gene. The Genbank number of the nucleotide sequence of the TK gene can be AA089373.1. Preferably, the nucleotide sequence of the leader RNA-1 is as shown in SEQ ID NO: 31, and the nucleotide sequence of the leader RNA-2 is as shown in SEQ ID NO: 32.

Preferably, in the donor DNA, the nucleotide sequence of the left homology arm is as shown in SEQ ID NO: 33 and the nucleotide sequence of the right homology arm is as shown in SEQ ID NO: 34.

Preferably, the nucleotide sequence of the donor DNA comprises the above-mentioned signal peptide coding sequence (for example, SEQ ID NO: 23) and the labeling polypeptide coding sequence, and also comprises the puro- GFP coding sequence. The nucleotide sequence of the puro-GFP coding sequence is as shown in SEQ ID NO: 35.

The puro-GFP coding sequence is preferably under the control of the promoter of the nucleotide sequence as shown in SEQ ID NO: 36, and the signal peptide coding sequence and the labeling polypeptide coding sequence are preferably under the control of the promoter of the nucleotide sequence as shown in SEQ ID NO: 37.

In a preferred embodiment of the present invention, the nucleotide sequence of the donor DNA is as shown in SEQ ID NO: 38.

Chimeric Antigen Receptor

The chimeric antigen receptor comprises in sequence an antigen-binding domain, a spacer region, a transmembrane region, and an intracellular domain that are operatively linked. The antigen-binding domain can specifically recognize and bind to the extracellular antigen determining region of the labeling polypeptide. The spacer region is used to separate the antigen-binding domain and the transmembrane region and the intracellular domain is used for signal transmission.

For the definitions of the terms "antigen-binding domain", "spacer region", "transmembrane region" and "intracellular domain" used in the present invention, please refer to "'Immunology introductory theory', Yu Shanqian, Higher Education Press, 2008"; and "'Immunobiology', seventh edition, Kenneth Murphy, Paul Travers, Mark Walport, etc".

The antigen-binding domain is preferably a single-chain antibody (ScFv) comprising a light chain and a heavy chain which can be connected to each other through a linker, as shown in FIG. 1.

The present invention further found that it is preferable that the amino acid sequence of the light chain of the antigen-binding domain targeting TT1 is consistent with the amino acid sequence at position 1 to 111 of the light chain of anti-Myc antibody (such as clone 9e10) (in other embodiments of the present invention, the amino acid sequence of the light chain of the antigen-binding domain targeting TT1 can be extended by no more than 10 amino acids downstream of the above sequence), and the amino acid sequence of the heavy chain is consistent with the amino acid sequence at position 23 to 143 of the heavy chain of anti-Myc antibodies (such as clone 9e10) (in other embodiments of the present invention, the amino acid sequence of the heavy chain of the antigen-binding domain targeting TT1 can extended by no more than 10 amino acids upstream and downstream of the above sequence).

Preferably, the amino acid sequence of the light chain of the antigen-binding domain targeting TT2 is consistent with the amino acid sequence at position 2 to 121 of the light chain of an anti-HA antibody (such as clone 12ca5) (in other embodiments of the present invention, the amino acid sequence of the light chain of the antigen-binding domain targeting TT2 can be extended by no more than 10 amino acids downstream of the above sequence), the amino acid sequence of the heavy chain is consistent with the amino acid sequence at position 2 to 114 of the heavy chain of an anti-HA antibody (such as clone 12ca5) (in other embodiments of the present invention, the amino acid sequence of the heavy chain of the antigen-binding domain targeting TT2 can be extended by no more than 10 amino acids downstream of the above sequence).

Preferably, the amino acid sequence of the light chain of the antigen-binding domain targeting TT3 is consistent with the light chain of the anti-Strep tag II antibody (see, for example, patent document EP2871189A1), and the amino acid sequence of the heavy chain is consistent with the heavy chain of the anti-Strep tag II antibody (see, for example, patent document EP2871189A1).

Wherein, the amino acid sequence of the light chain of the anti-Myc antibody (clone 9e10) can be derived from the amino acid sequence of PDB: 2ORB_L (https://www.ncbi.nlm.nih.gov/protein/2ORB_L), and the amino acid sequence of the heavy chain of the anti-Myc antibody (Clone 9e10) can be derived from the amino acid sequence of GenBank: CAA73271.1 (https://www.ncbi.nlm.nih.gov/protein/CAA73271.1?report=genbank&log$=protalign&blast_rank=1&RID=P597FX1S014). The amino acid sequence of the linker connecting the light chain and the heavy chain is as shown in SEQ ID NO:39. The amino acid sequence of the light chain of the anti-HA antibody (clone 12ca5) can be derived from the amino acid sequence of PDB: 5XCS_B (https://www.ncbi.nlm.nih.gov/protein/1258501213), and the amino acid sequence of the heavy chain of the anti-HA antibody (clone 12ca5) can be derived from the amino acid sequence PDB: 5XCS_A (https://www.ncbi.nlm.nih.gov/protein/5XCS_A). The amino acid sequence of the linker connecting the light chain and the heavy chain can be as shown in SEQ ID NO:40. The amino acid sequence of the light chain and the heavy chain of the anti-Strep tag antibody can be derived from the amino acid sequence disclosed in the patent document EP2871189A1, and the amino acid sequence of the linker connecting the light chain and the heavy chain can be as shown in SEQ ID NO:41.

More preferably, the amino acid sequences of the antigen-binding domains targeting TT1, TT2 and TT3 are as shown in SEQ ID NOs: 42-44, respectively.

The intracellular domain plays a role in signal transmission to activate T or NK cells. The intracellular domain of the CAR initially used for T cells has only one signal molecule, which is usually the receptor-related FcεRIγ of immunoglobulin E (one subunit of the receptor with high affinity to IgE) or CD3ζ, the basic transduction molecule of T cell antigen receptor signal. Some intracellular domains comprise T cell activation domains composed of one or more T cell activation motifs.

Preferably, the intracellular domain is derived from the lymphocyte intracellular activation signal transduction region and optionally the lymphocyte costimulatory signal transduction region (may include 0 to 2 costimulatory signal transduction regions). Preferably, the intracellular activation signal transduction region is derived from the intracellular signal region of CD3ζ and DAP12, and the costimulatory signal transduction region is derived from the intracellular signal region of 4-1BB, CD28, CD27, OX40, GITR and/or ICOS.

More preferably, the present invention has discovered that combining the above-mentioned antigen-binding domain with intracellular signal regions from 4-1BB and CD3ζ can obtain a CAR that enable T or NK cells to exert strong targeting tumoricidal activity. Preferably, the amino acid sequence of the intracellular domain is selected from position 209 to 255 of 4-1BB and position 52 to 164 of CD3ζ, wherein, the amino acid sequence number of CD3 is UniProtKB-P20963, and the amino acid sequence number of 4-1BB is UniProtKB-Q07011. The amino acid sequence of the intracellular domain is more preferably as shown in SEQ ID NO:45.

The present invention further selects the spacer region and the transmembrane region, thereby obtaining a CAR with a particular combination of antigen-binding domain-spacer region-transmembrane region-intracellular domain. The spacer region connects the antigen-binding domain and the transmembrane region. The structure of this region should be flexible, so that the antigen-binding domain can be adapted to different directions to promote the corresponding recognition and binding to antigens. The simplest form of the spacer region is the hinge region of immunoglobulin IgG1, and it can also be a part of the $C_{H2}C_{H3}$ region of an immunoglobulin. The transmembrane region is generally a hydrophobic alpha helix that spans the cell membrane. The spacer region can be derived from the hinge region of CD8α, the hinge region of IgG or the hinge region of IgD. The transmembrane region can be derived from the transmembrane region of CD8α, the transmembrane region of CD3ζ, the transmembrane region of CD4 or the transmembrane region of CD28.

Through researches and experimentations, the present invention found that the spacer region is more preferably derived from the hinge region of CD8α, and the transmembrane region is more preferably derived from the transmembrane region of CD8α. CD8 is a transmembrane glycosylated membrane protein composed of α and β subunits, which works with T cell surface receptors to allow T cells to bind to specific antigen. CD8 specifically binds to MHC I and mediates killing effect of cytotoxic T cells.

More preferably, the spacer region and the transmembrane region constitute a spacer transmembrane region, and the amino acid sequence of the spacer transmembrane region is consistent with the amino acid sequence at position Y to 210 of CD8α, and 118≤Y≤128 wherein Y is an integer. The UniProtKB number of the amino acid sequence of CD8α can be P01732. In other words, the amino acid sequence of the spacer transmembrane region is preferably selected from position 118 to 210 of CD8α and comprises the amino acids at position 128 to 210. For example, the amino acid sequence of the spacer transmembrane region is as shown in any one of the amino acid sequences selected from the group: position 118 to 210, position 119 to 210, position 120 to 210, position 121 to 210, position 122 to 210, position 123 to 210, position 124 to 210, position 125 to 210, position 126 to 210, position 127 to 210, or position 128 to 210 of CD8α.

Preferably, the expression of the chimeric antigen receptor is guided by a signal peptide which has the function of guiding the secretion of the target protein to the cell surface. The present invention found that the combination of the above-mentioned antigen-binding domain and the signal peptide from the GM-CSFα chain can make the chimeric antigen receptor effectively expressed on the surface of immune effector cells. The GM-CSFα chain signal peptide is the leader sequence that targets the chimeric antigen receptor of the present invention to the secretory pathway, the coding sequence of which is first translated into protein in the cell together with the coding sequence of the chimeric antigen receptor to guide the synthesized protein to enter into intracellular secretion pathway. The signal peptide is removed before the chimeric antigen receptor is expressed on the cell surface.

Preferably, the amino acid sequence of the signal peptide is selected from position 1 to 22 of the amino acid sequence of GM-CSF, wherein the amino acid sequence number of the signal peptide is UniProtKB-P15509. More preferably, the amino acid sequence of the signal peptide is as shown in SEQ ID NO:8.

In a specific embodiment of the present invention, the chimeric antigen receptor comprises in sequence an antigen-binding domain, a spacer region, a transmembrane region, and an intracellular domain that are operatively linked. In a more specific embodiment of the present invention, the antigen-binding domain is ScFv, the light chain and the heavy chain are respectively derived from the light chain and the heavy chain of anti-Myc, HA or Strep tag antibody, the spacer region is derived from the hinge region of human CD8α, the transmembrane region is derived from the transmembrane region of human CD8α, and the intracellular domain is derived from the combination of the intracellular signaling region of CD3ζ and 4-1BB.

In the present invention, the signal peptide, the antigen-binding domain, the spacer region, the transmembrane region and the intracellular domain are connected in sequence. The signal peptide and the antigen-binding domain, the antigen-binding domain and the spacer region, the spacer region and the transmembrane region, the transmembrane region and the intracellular domain are operatively linked. For example, they may be connected by a linker or be connected directly without any linker. In one embodiment of the present invention, the signal peptide and the antigen-binding domain are connected by a linker, such as GAHA, the antigen-binding domain and the spacer region are connected by a linker (the linker, for example, is -Ala-Ser-), while the spacer region and the transmembrane region, the transmembrane region and the intracellular domain are connected directly without a linker.

In a preferred embodiment of the present invention, the amino acid sequence of the chimeric antigen receptor is as shown in SEQ ID NO: 46 (corresponding to targeting TT1), SEQ ID NO: 47 (corresponding to targeting TT2) or SEQ ID NO: 48 (corresponding to targeting TT3).

```
SEQ ID NO: 46:
GAHADIVLTQSPAFLAVSLGQRATISCRASESVDNYGFSFMNWFQQKPGQPPKLLIYAIS

NRGSGVPARFSGSGSGTDFSLNIHPVEEDDPAMYFCQQTKEVPWTFGGGTKLEIKGSTSGS

GKPGSGEGSTKGQVQLQESGGDLVKPGGSLKLSCAASGFTFSHYGMSWVRQTPDKRLEW

VATISRGTYTYPDSVKGRFTISRDNDKNALYLQMDSLKSEDTAMYYCARRSEFYYYGNTY

YYSAMDYWGQGASVTVSSASFVPVFLPAKPTTTPAPRPPTPAPTIASQPLSLRPEACRPAAG

GAVHTRGLQFACDIYIWAPLAGTCGVLLLSLVITLYCNHRNRFSVVKRGRKKLLYIFKQPFMR

PVQTTQEEDGCSCRFPEEEEGGCELRVKFSRSADAPAYQQGQNQLYNELNLGRREEYDVL
```

-continued
DKRRGRDPEMGGKPRRKNPQEGLYNELQKDKMAEAYSEIGMKGERRRGKGHDGLYQGLS

TATKDTYDALHMQALPPR

The dark gray shows the scFv of the chimeric antigen receptor, the italic shows the linker that connects the light chain and the heavy chain, the light gray shows the spacer region, the single underline shows the transmembrane region, the boldface shows the part from 4-1BB in the intracellular signal region, and the double underline shows the part from CD3ζ in the intracellular signal region.

SEQ ID NO: 47:
GAHAEVKLVESGGDLVKPGGSLKLSCAASGFTFSSYGMSWVRQTPDKRLEWVATISRG

GSYTYYPDSVKGRFTISRDNAKNTLYLQMSSLKSEDTAMYYCARRETYDEKGPAYWGQGTT

VTVSSGGGGSGGGGSGGGGSDIELTQSPSSLTVTAGEKVTMSCKSSQSLLNSGNQKNYLT

WYQQKPGQPPKLLIYWASTRESGVPDRFTGSGSGRDFTLTISSVQAEDLAVYYCQNDNSHP

LTFGAGTKLELKASFVPVFLPAKPTTTPAPRPPTPAPTIASQPLSLRPEACRPAAGGAVHTRGL

DFACDIYIWAPLAGTCGVLLLSLVITLYCNHRNRFSVVKRGRKKLLYIFKQPFMRPVQTTQEE

DGCSCRFPEEEEGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQGLSTATKDTYDA

LHMQALPPR

The dark gray shows the ScFv of the chimeric antigen receptor, the italic shows the linker that connects the light chain and the heavy chain, the light gray shows the spacer region, the single underline shows the transmembrane region, the boldface shows the part from 4-1BB in the intracellular signal region, and the double underline shows the part from CD3ζ in the intracellular signal region.

SEQ ID NO: 48:
GAHAELVMTQSPASLAVSLGQRATISCRASESVDSYGKSFMHWYQLKPGQPPKLLIYRA

SNLESGVPARFSGSGSRTDFTLTIDPVEADDAATYYCQQNNEDPNTFGGGTKLEIKGSTSGS

GKPGSGEGSTKGEVQLEQSGPELVKPGASVKMSCKASGYTFTNYYMNWVKQSHGKSLEWI

GDINPNNGDTFYNQKFKGKATLTVDKSSNTAYMQLNSLTSEDSAVYYCARTGRYEENAMDY

WGQGTSVTVSSASFVPVFLPAKPTTTPAPRPPTPAPTIASQPLSLRPEACRPAAGGAVHTRG

LDFACDIYIWAPLAGTCGVLLLSLVITLYCNHRNRFSVVKRGRKKLLYIFKQPFMRPVQTTQE

EDGCSCRFPEEEEGGCELRVKFSRSADAPAYQQGONQLYNELNLGRREEYDVLDKRRGRD

PEMGGKPRRKNPQEGLYNELQKDKMAEAYSEIGMKGERRRGKGHDGLYQGLSTATKDTYD

ALHMQALPPR

The dark gray shows the ScFv of the chimeric antigen receptor, the italic shows the linker that connects the light chain and the heavy chain, the light gray shows the spacer region, the single underline shows the transmembrane region, the boldface shows the part from 4-1BB in the intracellular signal region, and the double underline shows the part from CD3ζ in the intracellular signal region.

Chimeric Antigen Receptor Encoding DNA

The coding DNA of the chimeric antigen receptor of the present invention comprises in sequence an antigen-binding domain coding element, a spacer region coding element, a transmembrane coding element and an intracellular domain coding element that are operatively linked, which is characterized in that, the antigen-binding domain encoded by the antigen-binding domain coding element can recognize and bind to the extracellular antigen determining region of the labeling polypeptide of the present invention.

The nucleotide sequence of coding element of the antigen-binding domain encodes the amino acid sequence of the antigen-binding domain. Preferably, the nucleotide sequence of the coding element of the antigen-binding domain targeting TT1 is as shown in SEQ ID NO:49. Preferably, the nucleotide sequence of the coding element of the antigen-binding domain targeting TT2 is as shown in SEQ ID NO:50. Preferably, the nucleotide sequence of the coding element of the antigen-binding domain targeting TT3 is as shown in SEQ ID NO:51.

The nucleotide sequence of the intracellular domain coding element encodes the amino acid sequence of the intracellular domain. Preferably, the coding element of the intracellular activation signal transduction region is derived from the encoding DNAs of the intracellular signal region of CD3ζ and DAP12, and the coding element of the co-stimulatory signal transduction region is derived from the encoding DNAs of intracellular signal region of 4-1 BB, CD28, CD27, OX40, GITR and/or ICOS. More preferably, the coding element of the intracellular domain is derived from the encoding DNAs of intracellular signal region of 4-1 BB and CD3ζ. More preferably, the nucleotide sequence of the coding element of the intracellular domain is as shown in SEQ ID NO:52.

The spacer region coding element is preferably derived from CD8α hinge region coding DNA, IgG hinge region coding DNA or IgD hinge region coding DNA. The transmembrane region coding element is preferably derived from CD8α transmembrane region coding DNA, CD3ζ transmembrane region coding DNA, CD4 transmembrane region coding DNA or CD28 transmembrane region coding DNA. Wherein, the spacer region coding element is more preferably derived from the hinge region coding DNA of CD8α, and the transmembrane region coding element is more preferably derived from the transmembrane region coding DNA of CD8α.

Preferably, the spacer region coding element and the transmembrane region coding element constitute a spacer transmembrane region coding element, and the nucleotide sequence of which encodes the amino acid sequence of the spacer transmembrane region. Preferably, the nucleotide sequence of the spacer region coding element comprises the sequence as shown in SEQ ID NO:22.

Preferably, the expression of the chimeric antigen receptor is guided by a signal peptide, and the nucleotide sequence of the signal peptide encodes the amino acid sequence of the signal peptide. Preferably, the amino acid sequence of the signal peptide is selected from position 1 to 22 of the amino acid sequence of GM-CSFα. Preferably, the nucleotide sequence of the signal peptide coding element is as shown in SEQ ID NO:23.

In a specific embodiment of the present invention, the chimeric antigen receptor encoding DNA comprises in sequence an antigen-binding domain coding element, a spacer region coding element, a transmembrane region coding element and an intracellular region coding element that are operatively linked, which is characterized in that the coding elements of the light chain and the heavy chain of the antigen-binding domain are derived from the coding DNA of the light chain and heavy chain of the anti-Myc tag, HA tag or Strep tag II antibody, respectively, the spacer region coding element is derived from the hinge region coding DNA of CD8α, the transmembrane region coding element is derived from the transmembrane region coding DNA of CD8α, and the intracellular domain is derived from the intracellular signal region coding DNAs of 4-1BB and CD3ζ.

Preferably, the nucleotide sequences of the DNA having the signal peptide coding sequence and the chimeric antigen receptor coding sequence is as shown in SEQ ID NO: 53 (corresponding to targeting TT1), SEQ ID NO: 54 (corresponding to targeting TT2) or SEQ ID NO: 55 (corresponding to targeting TT3).

CAR-Modified Immune Cells

The immune cells include T cells or NK cells; wherein, the NK cells include autologous NK cells, allogeneic NK cells or NK cell strain, and the T cells include primitive T cells or their precursor cells, effector T cells, memory T cell, NKT cell, or T cell strain.

The modification of chimeric antigen receptor to immune cells can be performed through lentiviral infection and mRNA electrotransfection.

Preferably, the first composition and the second composition are present separately in the therapeutic agent without being mixed together.

The nucleic acid having the labeling polypeptide coding sequence includes DNA or RNA; the RNA includes mRNA transcribed from the DNA. Preferably, the first composition comprises a therapeutically effective amount of the DNA or a therapeutically effective amount of the mRNA. Preferably, the first composition comprises the DNA or mRNA at a dose of 0.01-10 mg/day.

Preferably, the first composition comprises a therapeutically effective amount of the recombinant virus. More preferably, the first composition comprises a total dose of $5\times10^7$ to $5\times10^{12}$ virus particles or $5\times10^7$ to $5\times10^{12}$ PFU of the recombinant oncolytic vaccinia virus per treatment course.

Preferably, the second composition comprises a therapeutically effective amount of the CAR-modified immune cells. Preferably, a total dose of $1\times10^4$ to $1\times10^9$ cells/Kg body weight of the CAR-modified immune cells per treatment course is comprised.

The DNA can be formulated to be administered via intratumoral injection or intravenously; the mRNA can be formulated to be administered via intratumoral injection or intravenously. For example, it can be administered by direct intratumoral injection in the form of plasmids, or by intratumoral injection after being packaged by a liposome, or by intratumoral injection after the connection to nanoparticles (such as polymers like poly-L-lysine, polyamino acid, polyethyleneimine and chitosan, and the like), or by electrotransfection after intratumoral injection to enhance the transfection rate.

The recombinant virus can be formulated to be administered by intratumoral injection or intravenously.

The CAR-modified immune cells can be formulated to be administered via intravenous or topical administration.

Preferably, the therapeutic agent is composed of the first composition and the second composition.

Those skilled in the art can understand that the therapeutic agent of the present invention may also comprise suitable pharmaceutically acceptable excipients, including pharmaceutical or physiological carriers, excipients, diluents (includes physiological saline, PBS solution), and various additives including sugars, lipids, polypeptides, amino acids, antioxidants, adjuvants, preservatives, etc.

The present invention also provides the use of the therapeutic agent in the preparation of drugs for the treatment of tumors and/or cancers.

The tumors and/or cancers include breast cancer, head and neck tumor, synovial cancer, kidney cancer, connective tissue cancer, melanoma, lung cancer, esophageal cancer, colon cancer, rectal cancer, brain cancer, liver cancer, bone cancer, choriocarcinoma, gastrinoma, pheochromocytoma, prolactinoma, von Hippel-Lindau disease, Zollinger-Ellison syndrome, anal cancer, cholangiocarcinoma, bladder cancer, ureteral carcinoma, glioma, neuroblastoma, meningioma, spinal cord tumor, osteochondroma, chondrosarcoma, Ewing's sarcoma, cancer of unknown primary site, carcinoid, fibrosarcoma, Paget's disease, cervix carcinoma, gallbladder cancer, eye cancer, Kaposi's sarcoma, prostate cancer, testicular cancer, cutaneous squamous cell carcinoma, mesothelioma, multiple myeloma, ovarian cancer, pancreatic endocrine tumor, glucagon tumor, pancreatic cancer , penile cancer, pituitary cancer, soft tissue sarcoma, retinoblastoma, small bowel cancer, gastric cancer, thymic cancer, trophoblastic carcinoma, hydatidiform mole, endometrial cancer, vaginal cancer, vulvar cancer, mycosis fungoides, insulinoma, heart cancer, meningeal cancer, peritoneal cancer, pleural cancer and blood cancer.

The present invention also provides the above-mentioned labeling polypeptide of the present invention. The various embodiments of the labeling polypeptide are as described above.

Preferably, the amino acid sequence of the labeling polypeptide is as shown in SEQ ID NO: 11, SEQ ID NO: 12, SEQ ID NO: 13, SEQ ID NO: 14 or SEQ ID NO: 15.

The present invention also provides an isolated nucleic acid having the coding sequence of the labeling polypeptide of the present invention. The various embodiments of the nucleic acid are as described above.

The nucleic acid comprises in sequence an promoter, a signal peptide coding sequence and the coding sequence of the labeling polypeptide of the present invention that are operatively linked.

The nucleic acid comprises DNA and mRNA. Preferably, the nucleic acid is DNA, and its nucleotide sequence is as shown in SEQ ID NO: 26, SEQ ID NO: 27, SEQ ID NO: 28, SEQ ID NO: 29 or SEQ ID NO: 30.

The present invention also provides a recombinant expression vector, wherein the recombinant expression vector comprises in sequence an promoter, a signal peptide coding sequence, and the coding sequence of the labeling polypeptide of the present invention that are operatively linked.

In order to labeling a tumor cell with two or more labeling polypeptides simultaneously, the recombinant expression vector may comprise two or more coding sequences of the labeling polypeptide of the present invention.

Preferably, the recombinant expression vector (for example, pFastbac1-TT1, pFastbac1-TT2, pFastbac1-TT3, pFastbac1-C1&2a, pFastbac1-C1&2b) used to prepare the m RNA of the labeling polypeptide comprises in sequence a CMV promoter, a T7 promoter, a 5'UTR with kozak sequence, and a GM-CSFα chain signal peptide coding sequence before the coding sequence of the labeling peptide according to the present invention; and comprises a 3'UTR of the alpha globulin with polyA signal after the coding sequence of the labeling polypeptide of the present invention. The combination of the mentioned functional elements of the recombinant expression vector of the present invention can promote DNA transcription and translation, and enhance the stability of mRNA. The present invention also optimizes the structure of the above-mentioned functional elements as recited below, so as to better exert their due functions. Preferably, in the present invention, the sequence of the CMV promoter is as shown in SEQ ID NO:56. The function of the CMV promoter is to start the transcription of the downstream DNA sequences.

Preferably, in the present invention, the sequence of the T7 promoter is as shown in SEQ ID NO:57. The function of the T7 promoter is to start the transcription of the downstream DNA sequences.

Preferably, in the present invention, the sequence of the 5'UTR with the kozak sequence is as shown in SEQ ID NO: 58 and the function of the 5'UTR with the kozak sequence is to enhance the translation efficiency of mRNA.

Preferably, in the present invention, the sequence of the GM-CSF α chain signal peptide coding sequence is as shown in SEQ ID NO:23.

Preferably, in the present invention, the sequence of the 3'UTR of alpha globulin is as shown in SEQ ID NO: 59, which comprises a polyA signal. Its function is to enhance the stability of mRNA.

In a specific embodiment, the basic backbone of the recombinant expression vector is commercially available pFastbac1 vector which is then inserted with the above-mentioned elements.

Since the present invention optimizes the 3'UTR and 5'UTR structures, it is possible to use, for example, Tail-PCR to synthesize a DNA double-stranded template with PolyA in the positive strand and the corresponding PolyT in the reverse strand from the recombinant expression vector. By which, the instability of the DNA template is reduced, and mRNA can be synthesized in vitro. The number of the A in the PolyA of the positive chain (or the number of T in the PolyT of the reverse chain) is in the range of 140 to 170, preferably 150 to 170, more preferably more or less than 150 (for example, 150).

Methods of introducing this recombinant expression vector into tumor cells include methods via viral and non-viral. Non-viral methods include biological, physical, and chemically mediated gene transfection methods. Biological transfection methods include direct injection, receptor-mediated gene transfer, etc. Physical transfection methods include electrotransfection, microinjection, etc. Chemical transfection methods include liposomes and various cationic polymer-mediated transfections.

The present invention also provides an isolated recombinant virus, wherein the genome of the recombinant virus comprises in sequence a promoter, a signal peptide coding sequence, and a coding sequence of the labeling polypeptide of the present invention that are operatively linked, wherein the labeling polypeptide can be expressed to form modification on the surface of tumor cells and/or cancer cells; and the recombinant virus includes a replication-selective recombinant oncolytic virus or a replication-deficient recombinant virus.

Preferably, the recombinant virus is a replication-selective recombinant oncolytic virus, and the recombinant oncolytic virus is derived from a genetically mutated virus with oncolytic effect and a wild-type virus with oncolytic effect; preferably, the recombinant oncolytic virus is derived from adenovirus, poxvirus, herpes simplex virus, measles virus, Semliki forest virus, vesicular stomatitis virus, polio virus, retrovirus, reovirus, Seneca valley virus, Echo-type enterovirus, Coxsackie virus, Newcastle disease virus and Malaba virus with oncolytic effect.

The various embodiments of the recombinant virus are as described above.

The present invention also provides a recombinant expression vector (pFastbac1-TT3-PuroGFP (the nucleotide sequence of which is as shown in SEQ ID NO: 38)) for preparing recombinant virus, which comprises the coding sequence of the TT3 labeling peptide described above (i.e., SEQ ID NO: 28) operatively linked to pS promote, the coding sequence of the puro-GFP screening gene described above operatively linked to the p7.5 promoter, the LoxP site, left and right homology arms and gRNA cleavage site donor DNA. The recombinant expression vector is used to construct a recombinant oncolytic vaccinia virus using Crisper-Cas9 gene editing technique.

The present invention optimizes the structure of the above-mentioned functional elements as recited below, so as to better exert their due functions.

Preferably, in the present invention, the sequence of the pS promoter is as shown in SEQ ID NO:37. The function of pS promoter is to start transcription of downstream TT3 labeling polypeptide coding sequence.

Preferably, in the present invention, the sequence of the p7.5 promoter is as shown in SEQ ID NO:36. The function of the p7.5 promoter is to start transcription of the downstream puro-GFP coding sequence.

Preferably, in the present invention, the sequence of the LoxP site is as shown in SEQ ID NO:60. The function of LoxP site is to provide convenience for removing the screening gene.

Preferably, in the present invention, the sequence of the left homology arm is as shown in SEQ ID NO: 33 and the sequence of the right homology arm is as shown in SEQ ID NO: 34. The function of the homology arms is to homologously recombine the vaccinia virus genome with the donor plasmid.

Preferably, in the present invention, the sequence of the gRNA-1 cleavage site is as shown in SEQ ID NO: 61 and the sequence of the gRNA-2 cleavage site is as shown in SEQ ID NO: 62. The function of the gRNA cleavage site is to enable Crisper-Cas9 to cut the donor plasmid so as to improve the efficiency of homologous recombination.

In a specific embodiment, the basic backbone of the recombinant expression vector is commercially available pFastbac1 vector which is then inserted with each element described above.

The present invention also provides a chimeric antigen receptor which comprises orderly an antigen-binding domain, a spacer region, a transmembrane region, and an intracellular domain that are operatively linked, which is characterized in that the antigen-binding domain can recognize and bind to the extracellular antigen determining region of the labeling polypeptide of the present invention.

The various embodiments of the chimeric antigen receptor are as described above.

Preferably, the amino acid sequence of the chimeric antigen receptor is as shown in SEQ ID NO: 46 (corresponding to targeting TT1), SEQ ID NO: 47 (corresponding to targeting TT2) or SEQ ID NO: 48 (corresponding to targeting TT3).

The present invention also provides an isolated DNA having the coding sequence encoding the chimeric antigen receptor of the present invention.

The various embodiments of the DNA having the coding sequence of the chimeric antigen receptor are as described above.

Preferably, the nucleotide sequence of the DNA is as shown in SEQ ID NO: 53 (corresponding to targeting TT1), SEQ ID NO: 54 (corresponding to targeting TT2) or SEQ ID NO: 55 (corresponding to targeting TT3).

The present invention also provides an isolated mRNA transcribed from the DNA of the present invention.

The present invention also provides a recombinant expression vector (for example, pFastbac1-aTT1-CD8a-4-1BB-CD3ζ, pFastbac1-aTT2-CD8a-4-1BB-CD3ζ, pFastbac1-aTT3-CD8a-4-1BB-CD3ζ), wherein the recombinant expression vector comprises orderly a promoter, a signal peptide coding sequence, and a chimeric antigen receptor coding sequence of the present invention that are operatively linked.

Preferably, the recombinant expression vector comprises orderly a CMV promoter, a T7 promoter, a 5'UTR with a kozak sequence, and a GM-CSF α chain signal peptide coding sequence before the coding sequence of the chimeric antigen receptor of the present invention; and comprises a 3'UTR of the alpha globulin with polyA signal after the coding sequence of the chimeric antigen receptor of the present invention. The combination of the mentioned functional elements of the recombinant expression vector of the present invention can promote DNA transcription and translation and enhance the stability of mRNA. The present invention also optimizes the structure of the above-mentioned functional elements as recited below so as to better exert their due functions.

Preferably, in the present invention, the sequence of the CMV promoter is as shown in
SEQ ID NO:56. The function of CMV promoter is to start transcription of downstream DNA sequence.

Preferably, in the present invention, the sequence of the T7 promoter is as shown in SEQ ID NO:57. The function of the T7 promoter is to start transcription of downstream DNA sequences.

Preferably, in the present invention, the sequence of the 5'UTR with the kozak sequence is as shown in SEQ ID NO: 58 and the function thereof is to enhance the translation efficiency of mRNA.

Preferably, in the present invention, the sequence of the GM-CSF α chain signal peptide coding sequence is as shown in SEQ ID NO:23.

Preferably, in the present invention, the sequence of the 3'UTR of alpha globulin is as shown in SEQ ID NO: 59, which comprises a polyA signal. Its function is to enhance the stability of mRNA.

In a specific embodiment, the basic backbone of the recombinant expression vector is commercially available pFastbac1 vector which is then inserted with the above-mentioned elements.

Since the present invention optimizes the 3'UTR and 5'UTR structures, it is possible to use, for example, Tail-PCR to synthesize a DNA double-stranded template with PolyA in the positive strand and the corresponding PolyT in the reverse strand from the recombinant expression vector. By which, the instability of the DNA template is reduced and mRNA can be synthesized in vitro. The number of the A in the PolyA of the positive chain (or the number of the T in the PolyT of the reverse chain) is in the range of 140 to 170, preferably 150 to 170, more preferably more or less than 150 (for example, 150).

The present invention also provides a CAR-modified immune cell, the surface of which is modified by the chimeric antigen receptor of the present invention.

The immune cells can be T cells or NK cells; wherein, the NK cells include autologous NK cells, allogeneic NK cells or NK cell strain, and the T cells include primitive T cells or their precursor cells, effector T cells, memory T cell, NKT cell, or T cell strain.

The chimeric antigen receptor can modify immune cells through lentivirus infection, transposon and mRNA electrotransfection.

The present invention also provides a kit of combinational drug with synergistic effect for treatment of tumors and/or cancers, comprising:

a first container containing the first composition of the therapeutic agent of the present invention;

a second container containing the second composition of the therapeutic agent of the present invention, wherein the first container is separate from the second container; and instructions specifying timing and routes of administration.

The present invention also provides the use of the isolated nucleic acid having the coding sequence of the labeling polypeptide of the present invention in the preparation of drugs for treatment or prevention of tumors and/or cancers.

The invention also provides the use of the recombinant virus in the preparation of drugs for treatment or prevention of tumors and/or cancers.

The present invention also provides the use of the CAR-modified immune cells in the preparation of drugs for treatment or prevention of tumors and/or cancers.

The invention also provides the use of the kit in the preparation of drugs for treatment or prevention of tumors and/or cancers.

The tumors and/or cancers include breast cancer, head and neck tumor, synovial cancer, kidney cancer, connective tissue cancer, melanoma, lung cancer, esophageal cancer, colon cancer, rectal cancer, brain cancer, liver cancer, bone cancer, choriocarcinoma, gastrinoma, pheochromocytoma, prolactinoma, von Hippel-Lindau disease, Zollinger-Ellison syndrome, anal cancer, cholangiocarcinoma, bladder cancer, ureteral carcinoma, glioma, neuroblastoma, meningioma, spinal cord tumor, osteochondroma, chondrosarcoma, Ewing's sarcoma, cancer of unknown primary site, carcinoid, fibrosarcoma, Paget's disease, cervix carcinoma, gallbladder cancer, eye cancer, Kaposi's sarcoma, prostate cancer, testicular cancer, cutaneous squamous cell carcinoma, mesothelioma, multiple myeloma, ovarian cancer, pancreatic endocrine tumor, glucagon tumor, pancreatic cancer , penile cancer, pituitary cancer, soft tissue sarcoma, retinoblastoma, small bowel cancer, gastric cancer, thymic cancer, trophoblastic carcinoma, hydatidiform mole, endometrial cancer, vaginal cancer, vulvar cancer, mycosis fungoides, insulinoma, heart cancer, meningeal cancer, peritoneal cancer, pleural cancer and blood cancer.

The present invention also provides a method for treatment of tumor and/or cancer, including:
administering the first composition of the therapeutic agent of the present invention to a patient suffering from tumor and/or cancer; and
administering the second composition of the therapeutic agent of the present invention to the patient suffering from tumor and/or cancer.

The first composition and the second composition in the therapeutic agent may be administered simultaneously (for example, as a mixture), separately but simultaneously (for example, administered by intratumoral and intravenous injection, respectively) or in sequence (for example, first composition is administered first, and then the second composition is administered).

Preferably, the method comprises the following steps in a sequential manner:
1) administering the first composition to the patient suffering from tumor and/or cancer; and
2) administering the second composition of the therapeutic agent to the patient suffering from tumor and/or cancer after the administration of the first composition.

Preferably, 1 to 30 days after the administration of the first composition, administering the second composition of the therapeutic agent to the patient suffering from tumor and/or cancer.

The phrase "1 to 30 days after the administration of the first composition, administering the second composition of the therapeutic agent to the patient suffering from tumor and/or cancer" means that the time interval between the first administration of the second composition and the first administration of the first composition is in the range of 1 to 30 days (for example, 1, 2, 3, 4, 5, 6, 7, 8, 9, 10, 11, 12, 13...30 days), or the time interval between the first administration of the second composition and the most recent administration of the first composition is 1 to 30 days (for example, 1, 2, 3, 4, 5, 6, 7, 8, 9, 10, 11, 12 , 13...30 days). Preferably, the time interval between the first administration of the second composition and the most recent administration of the first composition is 1 to 30 days (for example, 1, 2, 3, 4, 5, 6, 7, 8, 9, 10, 11, 12, 13 . . . 30 days).

In a preferred embodiment of the present invention, the administration dose of the nucleic acid is 0.01mg/day to 10 mg/day, 1 to 3 times per day, and consecutively for 1 to 7 days.

In a preferred embodiment of the present invention, the administration dose of the recombinant oncolytic vaccinia virus is: about $5 \times 10^7$ to $5 \times 10^{12}$ virus particles (for single administration or multiple administrations) for total dose per treatment course or any value in the range, or the administration dose of the recombinant oncolytic vaccinia virus is: about $5 \times 10^7$ to $5 \times 10^{12}$ PFU (for single or multiple administrations) for total dose per treatment course or any value in the range. Its precise dose also depends on the judgment of the practitioner and the unique circumstance of each individual. In the case of multiple administrations, it is administered 1 to 3 times a day, consecutively for 1 to 7 days.

In a preferred embodiment of the present invention, the administered dose of the CAR-modified immune cells is $1 \times 10^4$ to $1 \times 10^9$ cells/Kg body weight for total dose per treatment course. Preferably, it is administered 1 to 3 times a day, consecutively for 1 to 7 days.

In certain embodiments, the method for treatment of tumor and/or cancer further includes administering other medicaments for treatment of tumor and/or cancer to the patient, and/or medicaments for regulating the patient's immune system, to enhance the number and the function of CAR-modified immune cells in the body. Said other medicaments for treatment of tumor and/or cancer include but are not limited to: chemotherapy drugs, such as cyclophosphamide, fludarabine; radiotherapy drugs; immunosuppressants, such as cyclosporine, azathioprine, Methotrexate, mycophenolate, FK50; antibodies, such as antibodies against CD3, IL-2, IL-6, IL-17, TNFα.

The DNA can be formulated to be administered via intratumoral injection or intravenously; the mRNA can be formulated to be administered via intratumoral injection or intravenously. For example, it can be administered by direct intratumoral injection in the form of plasmids, by intratumoral injection after package in a liposome, or by intratumoral injection after connection to nanoparticles (such as polymers like poly-L-lysine, polyamino acid, polyethyleneimine and chitosan, etc.), or by electrotransfection after intratumoral injection to enhance the transfection rate.

The recombinant virus can be formulated to be administered via intratumoral injection or intravenously.

The CAR-modified immune cells can be formulated to be administered via intravenous or topical administration.

The following will further explain or illustrate the content of the present invention by way of examples, but these examples should not be construed as limiting the protection scope of the present invention.

EXAMPLES

Unless otherwise specified, the experimental methods used in the following examples are performed using conventional experimental procedures, operations, materials, and conditions in the field of medical biological engineering.

Unless otherwise specified, all the percentage concentrations (%) of the respective agents indicate percentage by volume (%(v/v)).

Unless otherwise specified, cell culture is conducted at the condition of 37° C., 5% $CO_2$, and humidification (95% relative humidity).

The sources of the experimental materials used in the following examples are as follows:

PBMC is derived from the peripheral blood of healthy donors.

Human recombinant IL-2 (hrIL2) was purchased from Peprotech.

DPBS was purchased from Gibco.

The electric shock cup was purchased from Bio-Rad.

Unless otherwise specified, FBS was purchased from Sigma.

Human ovarian cancer cell line SKOV3-luc, human T cell line Jurkat, human liver cancer cell line SK-HEP-1, African green monkey kidney cell CV-1, human osteosarcoma cell 143B cells were purchased from ATCC, and human colorectal cancer cell line HCT116-luc was purchased from Perkin Elmer.

Vaccinia virus (DDVV-RFP): the oncolytic vaccinia virus DDVV-RFP is known, which belongs to the oncolytic vaccinia virus WR strain (see, for example, "X Song, et al. T-cell Engager-armed Oncolytic Vaccinia Virus Significantly Enhances Antitumor Therapy. Molecular Therapy. (2014); 22 1, 102-111"), functionally deficient in both TK gene and VGF gene and carries an exogenous red fluorescent protein (RFP) gene. Since the RFP gene only plays a role of screening/reporting, the anti-tumor function of the oncolytic vaccinia virus DDVV-RFP is substantially equivalent to the oncolytic vaccinia virus functionally deficient in TK gene and VGF gene. Moreover, the oncolytic vaccinia virus DDw-RFP can also be obtained by genetic modification of VSC20 vaccinia virus using conventional techniques in the art. VSC20 vaccinia virus is a vaccinia virus lack of VGF gene. For the preparation method of VSC20 vaccinia virus, please see "McCart, JA, et al. Systemic cancer therapy with a tumor-selective vaccinia virus mutant lacking thymidine kinase and vaccinia growth factor genes. Cancer Res (2001) 61: 8751-8757". The genetic modification involves the use of an artificial synthetic vaccinia virus early/late promoter pSEL to regulate the exogenous DsRed gene (i.e., the RFP gene), and insertion of the DsRed gene into the TK gene region of the vaccinia virus VSC20 strain using in vitro intracellular recombination technique, thereby constructing the oncolytic vaccinia virus DDVV-RFP.

Preparation Example 1: Preparation of Tumor Cells Labeled Respectively with TT1, TT2, TT3, C1&2a, C1&2b by Electroporation Technique $5\times10^6$ Jurkat, HCT116-luc, SKOV3-luc or SK-HEP-1 cells and 5 μg of mRNAs with TT1 (SEQ ID NO: 11), TT2 (SEQ ID NO: 12) or TT3 (SEQ ID NO: 13), C1&2a (SEQ ID NO: 14), C1&2b (SEQ ID NO: 15) coding sequences (obtained by the method of Preparation Example 8 respectively), respectively, were mixed in electrotransfer fluid P3 (product name "P3Primary Cell 4D-X Kit L", Lonza, item number V4XP-3012), put in a 100 μl of Nucleocuvette™ tube (product name "P3Primary Cell 4D-X Kit L", Lonza, item number V4XP-3012), and placed in ice bath for 5 minutes. Then, the electroporator of 4D-Nucleofector™ system (Lonza) was used and the electrotransfection was performed using the tumor cell electrotransfection program thereof. After electrotransfection, the cells were taken out and placed in corresponding tumor cell culture medium. Jurkat culture medium is RPMI (Gibco)+10% FBS (Hyclone), SKOV3-luc and HCT116-luc culture medium is McCoy's 5A+10% FBS, and SK-HEP-1 culture medium is EMEM (Gibco)+10% FBS. DNase (Roche) was added to the medium to final concentration of 10 ng/mL, and then was placed in an incubator at 37° C. in 5% $CO_2$ to recover overnight. After 24 hours, the cells were harvested and the electrotransfected cells were identified using a flow cytometer (purchased from BD, C6Samplar). Tumor cells labeled receptively with TT1, TT2, TT3, C1&2a, or C1&2b were obtained.

Test Example 1: Verification of the Label of Tumor Cells with Labeling Peptides by Electroporation According to the method of Preparation Example 1, the mRNAs with TT1 (SEQ ID NO: 11), TT2 (SEQ ID NO: 12) or TT3 (SEQ ID NO: 13) coding sequences (obtained by the method of Preparation Example 8 respectively), respectively, was electrotransfected to Jurkat immortalized T lymphocytes, human ovarian cancer cell SKOV3-luc, human colorectal cancer cell HCT116-luc or human liver cancer cell SK-HEP-1 by 4D-Nucleofector™ system (Lonza), respectively. Staining was performed with a FITC-conjugated anti-Myc antibody (Santa Cruz), a FITC-conjugated anti-HA antibody (Biolegend), a FITC-conjugated anti-Strep tag II antibody (Genscript) (the dilution ratio is 1:50, respectively). The cells were identified by Flow cytometry (purchased from BD, C6Samplar).

The results are shown in FIG. 5, and the high-intensity expression of TT1, TT2 and TT3 on the surface of tumor cells can be successfully detected. Among them, Jurkat immortalized T lymphocytes were labeled by TT1 and TT2 (as shown in FIGS. 5A and 5B), human ovarian cancer cells SKOV3-luc (FIG. 5C), human colorectal cancer cell HCT116-luc (FIG. 5D) and human liver cancer cell SK-HEP-1 (FIG. 5E) were labeled by TT3. The left peak in the figure is the wild-type tumor cells stained with the above antibodies (negative control curve), while the right peak is the TT1 (A), TT2 (B) or TT3 (C-E) expression intensity curve in tumor cells after the electrotransfection of mRNAs encoding TT1, TT2 or TT3, respectively.

Preparation Example 2: Preparation of CAR-T Cells Targeting TT1, TT2, and TT3, Respectively $2\times10^6$ human PBMC cells were resuspended in 1 ml T cell culture medium (AIMV (Gibco) supplemented with 1% human AB serum (Valley Biomedical)), and OKT3 (eBioscience) with a final concentration of 100 ng/mland 300IU/ml of hrIL-2 (Peprotech) were added, then incubated into one well of a 24-well plate and placed in a humidified cell culture incubator (Thermo Fisher) at 37° C. in 5% $CO_2$. hrIL-2 with a final concentration of 300IU/ml was supplemented every 2 to 3 days. Fresh T cell culture medium was supplemented according to the condition of cell growth and the number of cells was adjusted to $1\times10^6$ cells/ml.

T cells cultured for 7 to 14 days ($1\times10^7$ cells) and 4pg of aTT3-CD8-41BB-CD3ζ mRNA (i.e., the mRNA corresponding to the nucleotide sequence as shown in SEQ ID NO: 55 (obtained by the method of Preparation Example 8)) were mixed in electrotransfer fluid P3 (product name "P3Primary Cell 4D-X Kit L", Lonza, item number V4XP-3012), and placed in a 100 μl of Nucleocuvette ™ tube (product name "P3Primary Cell 4D-X Kit L", Lonza, Item No. V4XP-3012), and frozen in an ice bath for 5 minutes. Then, the electrotransfection was performed using 4D-Nucleofector™ system (Lonza) and T cell electrotransfection program thereof. After electrotransfection, the cells were taken out and placed in T culture medium, 300IU/ml (final concentration) of hrIL2 and 10 ng/mL of DNase (Roche) were added, and then placed in an incubator at 37° C. in 5% $CO_2$ to recover overnight. After 24 hours, the cells were harvested, and the electrotransfected cells were identified by a flow cytometry. CAR-modified T cells targeting TT3 (i.e., aTT3-CD8-41BB-CD3ζ CAR) were obtained.

The preparation methods of CAR-T cells targeting TT1 and TT2 are similar with the above method except that aTT1-CD8-41BB-CD3ζ mRNA (i.e., the mRNA corresponding to the nucleotide sequence as shown in SEQ ID NO: 53 (obtained by the method of Preparation Example 8)), aTT2-CD8-41BB-CD3ζ mRNA (i.e., the mRNA corresponding to the nucleotide sequence as shown in SEQ ID NO: 54 (obtained by the method of Preparation Example 8)) were used.

Example 1: The Tumor-Killing Ability of CAR-T cells Targeting Labeling Polypeptide on Tumor Cells Labeled with the Labeling Polypeptide by Electrotransfection This example tested the killing ability of CAR-T cells targeting labeling polypeptides on Jurkat cells after being labeled by electrotransfection. The CAR-modified T cells targeting TT1 or TT2 or non-CAR-modified T cells obtained by the method of Preparation Example 2 were co-cultured respectively with the human T cell line Jurkat cells labeled with TT1 or TT2 by electrotransfection obtained by the method of Preparation Example 1 in a U-shaped 96-well plate, the number ratio (E:T) of the above CAR-T effector cells to target cells ranges from 1.25:1 to 20:1. Each experiment was repeated 3 times. After 2 hours of co-cultivation, DELFIA EuTDA Cytotoxicity Kit (Perkin Elmer, USA) was used to detect the ability of CAR-T cells to lyse tumor cells. The killing effect was calculated with the following formula: % specific lysis=((experimental group release (reading)–blank group release (reading))/(maximum release (reading)–blank group release (reading))×100.

Figure 6:
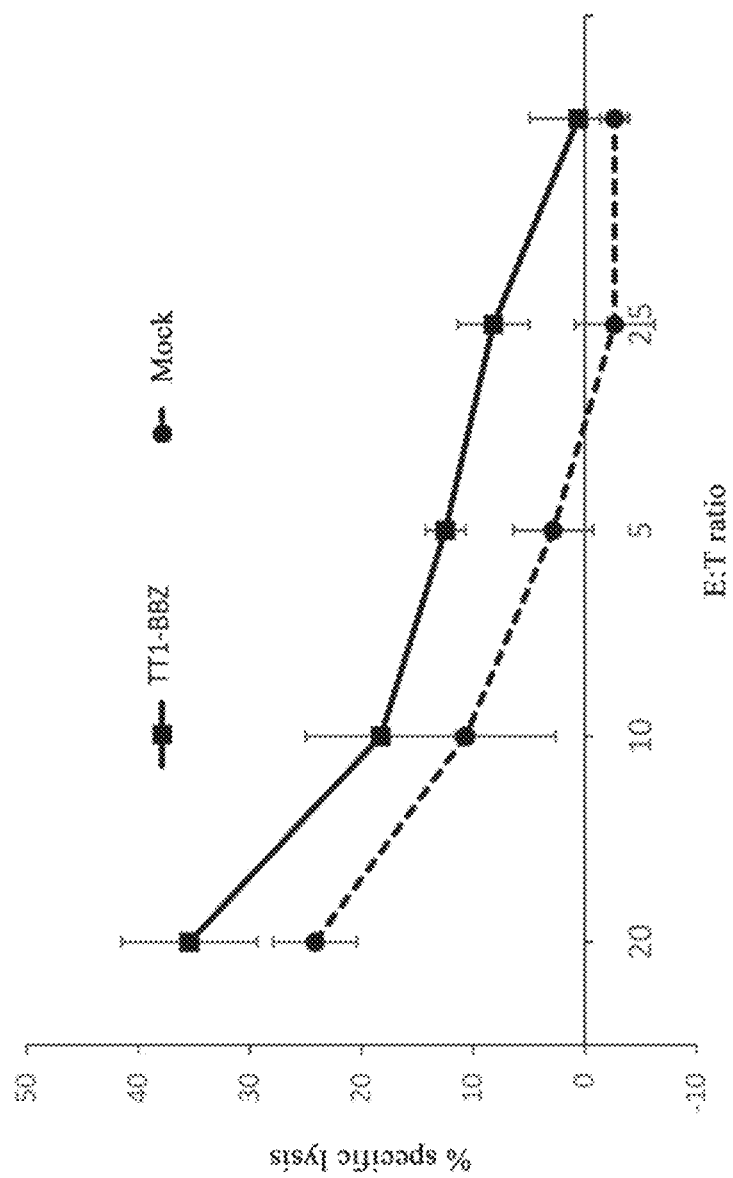
FIG. 6 shows the results of the in vitro killing experiment of CAR-T cells against TT1 on labeled Jurkat cells in Example 1 of the present invention. The ordinate represents % specific lysis (that is, the proportion of specific lysis) of tumor cells after being killed; the abscissa represents the ratio of effector cells to tumor cells; the solid line, namely "TT1-BBZ", shows the killing result of the CAR-modified T cell group targeting TT1 on the TT1-labeled Jurkat cells; the dotted line, namely "Mock", shows the killing result of the blank electrotransformed T cell group (negative control group) on the TT1-labeled Jurkat cells.
Figure 7:
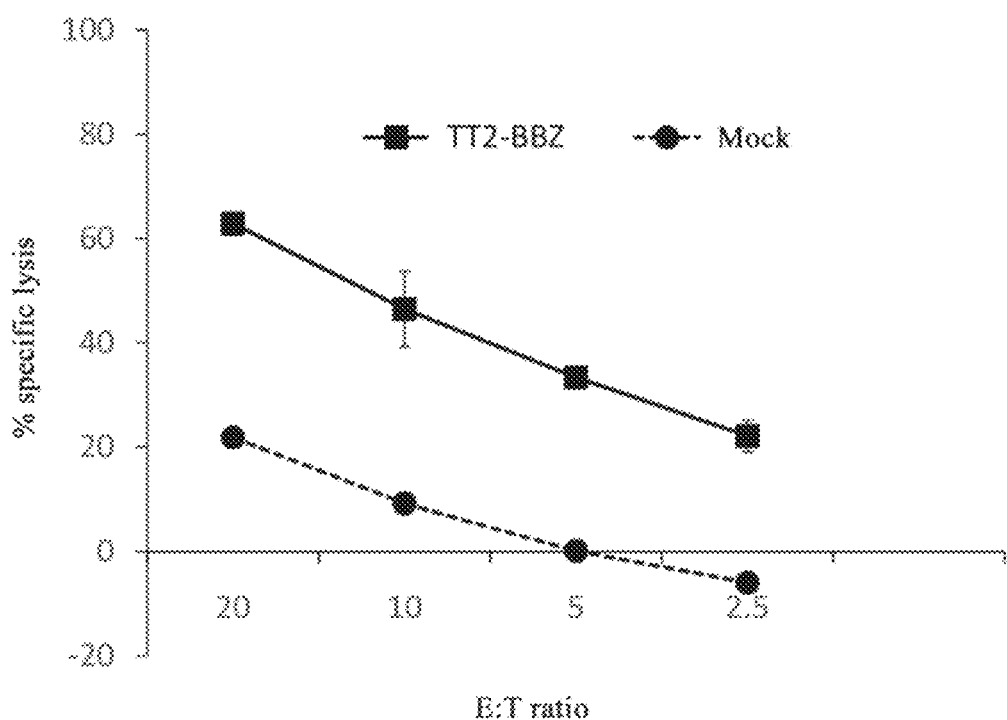
FIG. 7 shows the results of the in vitro killing experiment of CAR-T cells against TT2 on labeled Jurkat cells in Example 1 of the present invention. The ordinate represents the % specific lysis of tumor cells after being killed; the abscissa represents the ratio of effector cells to tumor cells; the solid line, namely "TT2-BBZ", shows that the killing result of the CAR-modified T cell group targeting TT2 on the TT2-labeled Jurkat cells; the dotted line, namely "Mock", shows the killing result of the blank electrotransformed T cell group (negative control group) on the TT2-labeled Jurkat cells.

The results were shown in FIGS. 6 and 7: Compared with the negative control T cell group (Mock group, without adding CAR-encoding mRNA, T cells was only electrotransfected with blank control), The killing ability of CAR-T cells targeting TT1 or TT2 on Jurkat cells electrotransfected with TT1 or TT2 was significantly increased, and the killing ratio can be increased by 15% and 40% respectively (E:T=20:1).

Example 2: CAR-T cells Targeting a Labeling Polypeptide can Kill a Variety of Tumor Cells Labeled with the Labeling Polypeptide by Electrotransfection This example tested the broad-spectrum applicability of CAR-T cells for killing tumor cells labeled by electrotransfection. The CAR-modified T cells targeting TT3 obtained by the method of Preparation Example 2 or wild-type T cells (as the negative control group of CAR) were respectively co-cultured with the human T cell line Jurkat or human colorectal cancer cell line HCT116-luc labeled with TT3 by electrotransfection in a U-shaped 96-well plate, and the number ratio of the above-mentioned effector cells to target cells (E:T) ranges from 2.5:1 to 20:1. Each experiment was repeated 3 times. After 2 hours of co-cultivation, the DELFIA EuTDA Cytotoxicity Kit (obtained from Perkin Elmer, USA) was used to detect the ability of CAR-T cells to lyse tumor cells. The killing effect was calculated using the following formula: % specific lysis=((experimental group release (reading)–blank group release (reading))/(maximum release (reading)–blank group release (reading))×100.

Figure 8:
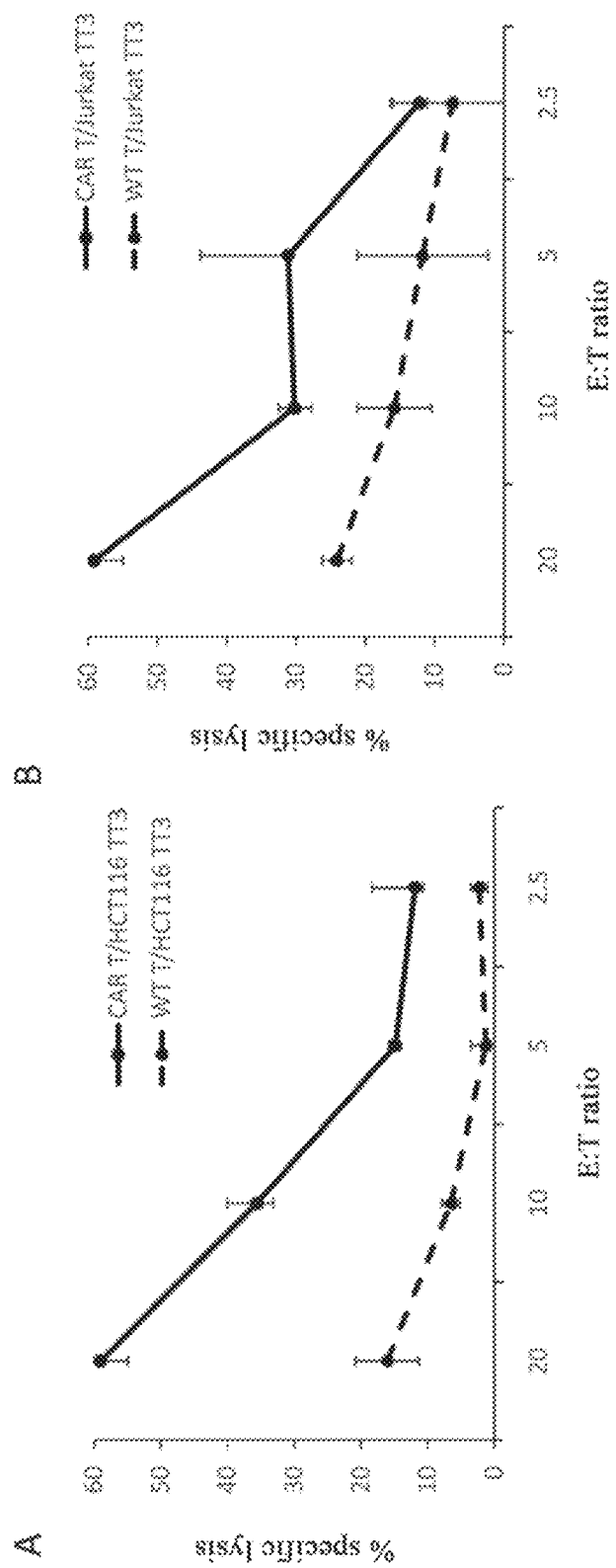
FIG. 8 shows the results of the in vitro killing experiment of CAR-T cells targeting TT3 on labeled HCT116-luc (A) and Jurkat (B) cells in Example 2 of the present invention. The ordinates represent % specific lysis of tumor cells after being killed; the abscissas represent the ratio of effector cells to tumor cells; the solid lines, namely "CAR T/HCT116 TT3" and "CAR T/Jurkat TT3" indicate respectively the results of the CAR modified T cell groups targeting TT3; the dotted lines, namely "WT T/HCT116 TT3" and "WT T/Jurkat TT3" show respectively the results of the wild-type T cell groups (negative control group).

The results are shown in FIG. 8: Compared with wild-type T cells, CAR-T cells targeting TT3 can not only significantly kill Jurkat cells labeled with TT3 by electrotransfection, but also kill HCT116-luc cells labeled with TT3 by electrotransfection, and the killing ratio can be increased by more than 40% (HCT116-luc cells) and 35% (Jurkat cells) respectively (E:T=20:1).

Example 3: CAR-T Cells Targeting Labeling Polypeptides can Specifically Kill Tumor Cells Labeled by Electrotransfection This example tested the specificity to the labeled tumor cell of the CAR-T cells targeting the labeling polypeptide of the present invention. The CAR-T cells targeting TT3 or mGFP-Z modified T cells (the GFP sequence (the Genbank number is YP_002302326.1) was used to replace the antigen binding domain in aTT3-CD8-41BB-CD3ζ CAR, used as the negative control group of CAR) obtained by the method of Preparation Example 2 was co-cultured respectively with the human colorectal cancer cell line HCT116-luc which is labeled with TT3 by electroporation or not labeled in a U-shaped 96-well plate. The ratio of the number of effector cells to target cells (E:T) ranges from 5:1 to 20:1. Each experiment was repeated 3 times. After 2 hours of co-cultivation, the DELFIA EuTDA Cytotoxicity Kit (obtained from PerkinElmer, USA) was used to detect the ability of CAR-T cells to lyse tumor cells. The killing effect was calculated using the following formula: % specific lysis= ((experimental group release (reading)–blank group release (reading))/(maximum release (reading)–blank group release (reading))×100.

Figure 9:
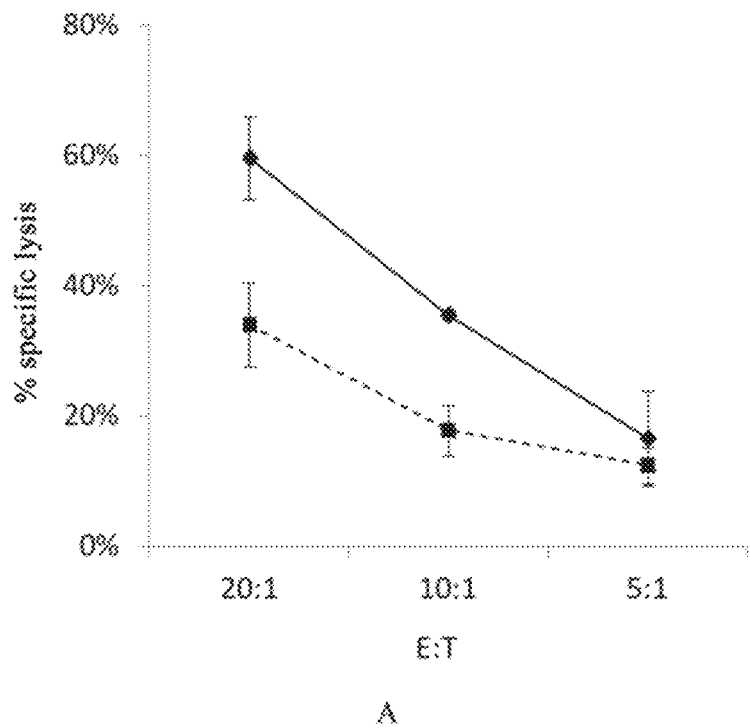
FIG. 9 shows the results of the in vitro killing experiment of CAR-T cells targeting TT3 on HCT116-luc that is labeled or not labeled with TT3 in Example 3 of the present invention. FIG. A shows the HCT116-luc labeled with TT3, and FIG. B shows the HCT116-luc not labeled with TT3. The ordinates represent the ratio of tumor cells being specifically lysed after being killed; the abscissas represent the ratio of effector cells to tumor cells; the solid lines, namely "αTT3-41BBζ", show the result of the CAR modified T cell groups targeting TT3; the dotted lines, namely "GFP-ζ", show the result of the mGFP-Z modified T cell groups (negative control group).
Figure 9:
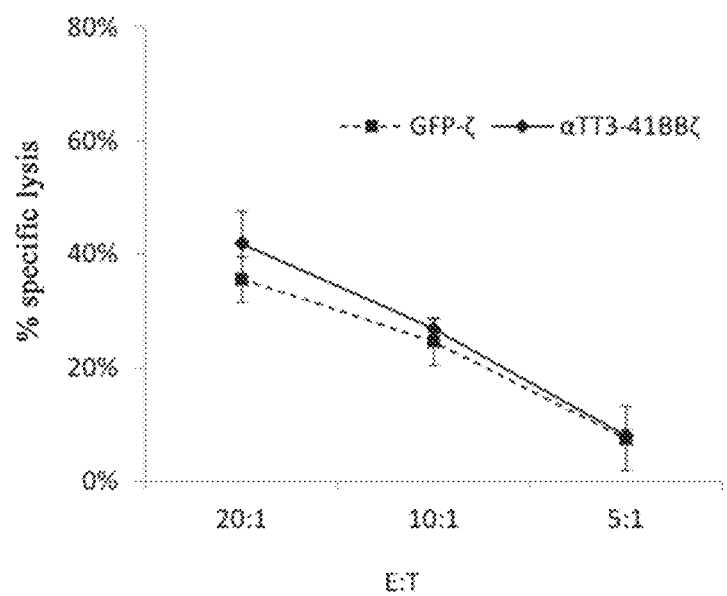

The results are shown in FIG. 9: Compared with the CAR negative control group (mGFP-Z), CAR-T cells targeting TT3 can significantly kill the HCT116-luc cells labeled with TT3 by electrotransfection (FIG. 9A), and the killing ratio can be increased by more than 20% (E:T 20:1). For the unlabeled HCT116-luc cells, the CAR negative control group and CAR-T cells targeting TT3 have almost no difference in killing HCT116-luc. This proves the specificity to TT3 of the CAR targeting TT3.

Example 4: Tumor Cells can be Labeled with Two Kinds of Epitope Polypeptides and Recognized by Corresponding CAR-T Cells The two epitope polypeptides were cloned into one carrier so that the tumor cells can be simultaneously labeled with the two epitope polypeptides, thereby different CAR-T cells can be used to track and kill the labeled tumor cells simultaneously or in sequence. Furthermore, according to the method recited in Preparation Example 8, two epitope polypeptides were cloned into the pFastbac1 vector (Life Technologies) using different spacer transmembrane regions, and vectors expressing the labeling polypeptides C1&2a and C1&2b were obtained (pFastbac1-C1&2a and pFastbac1-C1&2b, respectively), and then the mRNAs of C1&2a (SEQ ID NO: 14), C1&2b (SEQ ID NO: 15) coding sequence were prepared. Further, Jurkat cells labeled with C1&2a or C1&2b were obtained according to the method of Preparation Example 1. Wherein, C1&2a comprises 3 repeated epitope polypeptides derived from Myc tag and 3 repeated epitope polypeptides derived from HA tag. C1&2b comprises two repeated epitope polypeptides derived from Myc tag and two repeated epitope polypeptides derived from HA tag. The amino acid sequence of C1&2a is as shown in SEQ ID NO: 14 and the amino acid sequence of C1&2b is as shown in SEQ ID NO: 15. The nucleotide sequence of the nucleic acid with the coding sequence of the labeling polypeptide C1&2a is as shown in SEQ ID NO: 29, and the nucleotide sequence of the nucleic acid with the coding sequence of the labeling polypeptide C1&2b is as shown in SEQ ID NO: 30.

IFNγ ELISpot (Mabtech) was used to detect the IFNγ secretion of CAR-T after the stimulation by tumor cells. The T cells electrotransfected with the blank control (Mock-T) or electrotransfected with the mRNA of the CAR targeting TT1 or TT2 by electrotransfection obtained by the method of Preparation Example 2 were co-cultured respectively with the Jurkat cells labeled with C1&2a or C1&2b obtained by the method of Preparation Example 1 on an IFNα ELISPOT detection plate, and the ratio of the number of CAR-T effector cells to target cells (E:T) is 10:1. Each experiment was repeated 3 times. After 24 hours of co-cultivation, development was performed and ELISPOT points were counted by using the software Immunospot.

Figure 10:
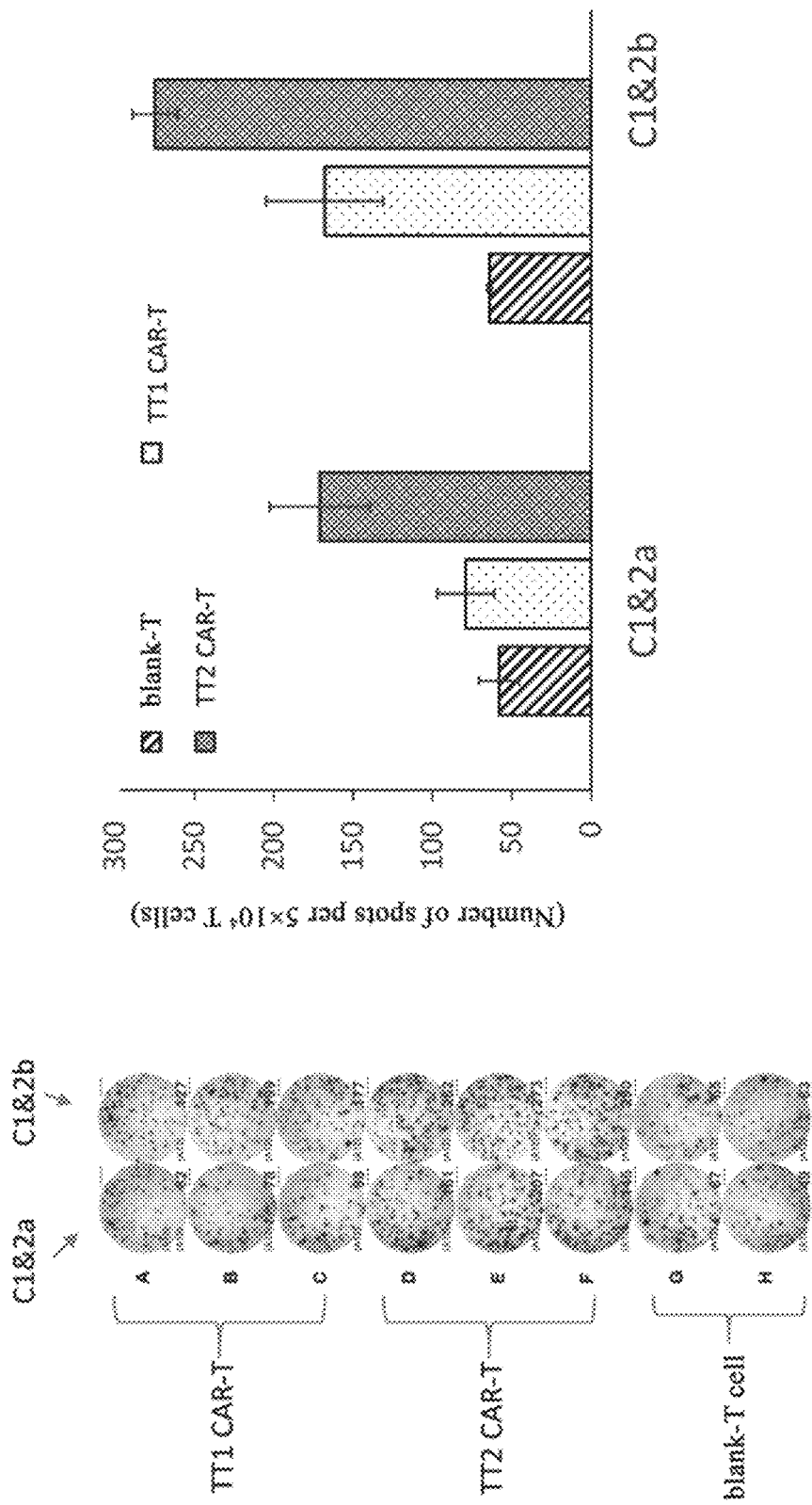
FIG. 10 shows the Elispot results of the release of IFN-γ after CAR-T cells targeting TT1 or TT2 are co-cultured with labeled Jurkat cells in Example 4 of the present invention. Left panel is a picture of the experimental wells of Elispot and the right panel is the statistical result of Elispot analysis. In the figures, "blank-T" indicates the T cell group not modified by CAR (control group), and "TT1 CAR-T" and "TT2 CAR-T" indicate the T cell group modified by CAR targeting TT1 or TT2, respectively. In the right panel, the abscissa represents Jurkat cells labeled with different labeling polypeptides, and the ordinate represents the relative number of IFN-γ (indicated by the number of spots per $5 \times 10^4$ T cells).

As shown in FIG. 10, the left panel is a representative picture of IFNγ ELISpot, and the right panel is the statistic result of the number of IFNγ spots. Compared with T cells without CAR modification, CAR-T cells targeting TT1 or TT2 can respond simultaneously to C1&2a or C1&2b labeled Jurkat cells. CAR-T cells targetingTT1 or TT2 has a stronger response to C1&2b than C1&2a.

Preparation Example 3: Preparation of Chimeric Antigen Receptor Modified NK Cells Targeting TT3

$20 \times 10^6$ human PBMC cells and 2mL of NK cell activator I (purchased from Shenzhen Dakewe, DKW35-CYT-NK001) were mixed homogenously in 400ml of NK culture medium (NK culture medium is AIM V® medium (purchased from Life Technologies)+1% human serum (purchased from Valley Biomedical, item number HP1022H1)), inoculated in a G-Rex100 cell culture device (purchased from Wilson Wolf), and added with IL2 (final concentration: 50 IU/l), placed in a cell culture incubator at 37° C., supplemented with the entire volume of IL2 every other day (final concentration: 50 IU/ml), cultured for 10 days, and then the cells were harvested and count. $20 \times 10^6$ cells was taken out from the harvested cells and uniformly mixed with another 2 mL of NK cell activator I in 400 ml of NK culture medium, and then inoculated back to the G-Rex100 cell culture device, and further cultured for 7 days at the same conditions. The remaining cells on the Day 10 mentioned above were frozen for later use, and the cells on the Day 16 were harvested and counted. $2 \times 10^6$ cells were taken out for cell phenotype analysis by a flow cytometry (using anti-CD3ζ and anti-CD56 antibodies, respectively: PE-conjugated anti-human CD3ζ antibody and APC-conjugated anti-human CD56 antibody (purchased from Miltenyi), 1:50 dilution).

NK cells cultured for 16 days ($1 \times 10^7$ cells) and 4 μg of aTT3-CD8-41BB-CD3ζ mRNA (obtained by the method of Preparation Example 8) were mixed in electrotransfer fluid P3 (product name "P3Primary Cell 4D-X Kit L", Lonza, item number V4XP-3012), placed in a 100 μl of Nucleocuvette™ tube (product name "P3Primary Cell 4D-X Kit L", Lonza, item number V4XP-3012), and frozen in an ice bath for 5 minutes. Then the 4D-Nucleofector™ system (Lonza) was used and the NK cells electrotransfection program thereof was selected for electrotransfection. After electrotransfection, the cells were taken out and placed in the NK cell culture medium, 50 IU/ml of IL2 and 10 ng/mL of DNase were added, and placed in an incubator at 37° C. in 5% $CO_2$ to recover overnight. After 24 hours, the cells were harvested, and the electrotransfected cells were identified using a flow cytometer (purchased from BD, C6 Samplar). CAR-modified NK cells targeting TT3 (i.e., aTT3-CD8-41BB-CD3ζ CAR) were obtained.

Example 5: Tumor Killing Ability of CAR-NK cells Targeting Labeling Polypeptides on Labeled Tumor Cells by Electrotransfection This example tested the killing ability of CAR-modified NK cells targeting labeling polypeptides to electrotransfected-labeled SKOV3-luc or SK-HEP-1 cells. The CAR-modified NK cells targeting TT3 or mGFP-Z-modified NK cells (the GFP sequence (the Genbank number is YP_002302326.1) was used to replace the antigen binding domain in aTT3-CD8-41BB-CD3ζCAR, used as the negative control group of CAR) were co-cultured respectively with the human ovarian cancer cell line SKOV3-luc or human hepatoma cell line SK-HEP-1 labeled with TT3 by electrotransfection in a U-shaped 96-well plate, and the ratio of the number of CAR-NK effector cells to target cells (E:T) is 10:1. Each experiment was repeated 3 times. After 2 hours of co-cultivation, the DELFIA EuTDA Cytotoxicity Kit (PerkinElmer, USA) was used to detect the ability of CAR-NK cells to lyse tumor cells. The killing effect was calculated using the following formula: % specific lysis'((experimental group release (reading)–blank group release (reading))/(maximum release (reading)–blank group release (reading))×100.

Figure 11:
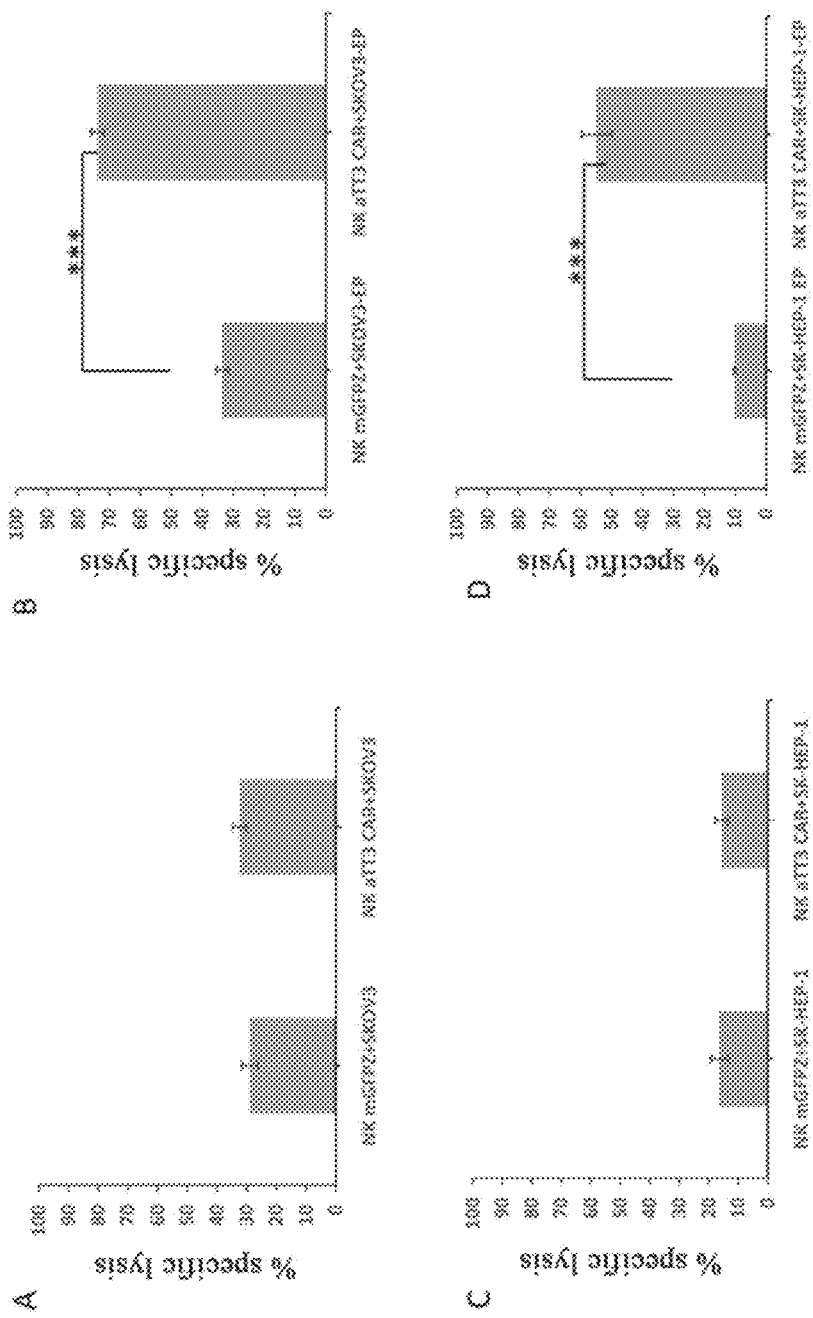
FIG. 11 shows the results of in vitro killing experiments of CAR-NK cells targeting TT3 (shown as NK aTT3 CAR in the figure) on labeled and unlabeled SKOV3-luc or SK-HEP-1 in Example 5 of the present invention. FIG. A is the result of SKOV3-lucthat is not labeled by TT3 (shown as SKOV3 in the figure), FIG. B is the result of SKOV3-luc that is labeled with TT3 by electrotransfer (shown as SKOV3-EP in the figure); Figure C is the result of SK-HEP-1 that is not labeled with TT3 (shown as SK-HEP-1 in the figure), Figure D is the result of SK-HEP-1 that is labeled with TT3 by electrotransfer (shown as SK-HEP-1-EP in the figure). Among them, mGFP-Z modified NK cells (shown as NK mGFPZ in the panel) were used as a negative control; the ordinates indicate the proportion of tumor cells specifically lysed after being killed; the abscissas indicate the different experimental groups; the ratio of effector cells to target cells is 10:1.

The results are shown in FIG. 11. Compared with the negative control group, CAR-NK cells targeting TT3 have significantly higher killing ability on SKOV3-luc and SK-HEP-1 cells electrotransfected with TT3, and the killing ratio can be increased about 40%, respectively.

Preparation Example 4: Preparation of HCT116-luc Cell Line Labeled Stably with TT3

First, the recombinant expression vector pFastbac1-TT3 which can be used for mRNA synthesis was linearized with ClaI restriction endonuclease, and then the linearized fragments were recovered by gel cutting. $4 \times 10^5$ HCT116-luc cells were inoculated to one well of a 6-well plate. 2 μg of linearized plasmid were mixed with 4 μl of P3000 (purchased from Life Technologies) and 125 μl of Opti-MEM (Gibco), which named as mixture 1; 6 μl Lipo3000 (purchased from Life Technologies) was mixed with 125 μl of Opti-MEM, which named as mixture 2. Mixture 1 and mixture 2 were mixed and named as mixture 3, and then incubated at room temperature for 15 minutes. The culture solution in the 6-well plate was discarded and 2 ml of McCoy's 5A+10% FBS culture solution was added and mixture 3 was added to the culture solution. After 24 hours of transfection, the culture medium was discarded and replaced with 2 ml of fresh McCoy's 5A+10% FBS medium. After one week of culture, HCT116-luc cells were stained with a FITC-conjugated anti-Strep Tag 11 antibody (purchased from Genscript, diluted by 1:50) (stained at 4° C. for half an hour), and single-cell sorting was performed by BD FACSAria IIsorter. Cells that express TT3 (that is, FITC positive) were sorted which can be used after multiplication culture.

Preparation Example 5: Preparation of Chimeric Antigen Receptor Modified T Cells Targeting TT3 by Lentivirus The nucleotide sequence of the DNA having the coding sequence of the chimeric antigen receptor targeting TT3 (as shown in SEQ ID NO: 55) was inserted into the third-generation self-inactivated lentiviral expression vector (CD810A-1; System Biosciences) according to conventional techniques in the art. The lentivirus was produced by HEK293FT cells (Life Technologies). The virus supernatant was harvested and concentrated by ultracentrifugation at 25,000 rpm for 3 hours. To prepare CAR-T cells transduced with lentivirus, Ficoll-Paque density gradient centrifugation (GE Healthcare) was firstly used to isolate human peripheral blood mononuclear cells (PBMCs) from fresh blood of healthy donors. After the isolated PBMCs were activated with human CD3/CD28 dynabeads® (Life Technologies), they were cultured in AIM-V (Life Technologies) medium supplemented with 5% human AB serum (Valley Biomedical) and 300 IU/ml of IL-2 (Peprotech). After one week of culture, the activated PBMC cells were infected with a lentivirus comprising the sequence of the chimeric antigen receptor targeting TT3, and were cultured for another week before use.

Example 6: CAR-T Cells Targeting TT3 Effectively Kills Tumor Cells Stably Labeled with TT3 by Lentivirus in Mice The mouse model implanted with human tumors was further used to test the in vivo tumor killing effect of CAR-T cells targeting TT3. The experimental mice were non-obese diabetic/severe combined immunodeficiency/IL-2Rγcnull (NSG) mice (aged 6 weeks to 8 weeks, female). Each mouse was implanted with $1\times10^7$ human colorectal cell line HCT116-luc labeled with TT3 (prepared by preparation example 4). Seven days after the tumor was implanted, the tumor growth was observed on the IVIS Spectrum imaging platform using in vivo biological imaging technology (BLI), and the tumor growth was recorded with an imager (purchased from Perkin Elmer, USA). Mice with similar BLI intensity (BLI intensity refers to the fluorescence intensity of tumor cells in mice recorded by in vivo imager) were randomly divided into 4 groups: phosphate buffered saline (PBS) group, control RNA CAR-T cell group, RNA CAR-T cell targeting TT3 group, and DNA CAR-T cell targeting TT3 group, 5 mice in each group. The control RNA CAR-T (transfected with mGFPZ-CAR) and the RNA CAR-T targeting TT3 were prepared by the method of Preparation Example 2, and the DNA CAR-T targeting TT3 was prepared by the preparation method of Preparation Example 5. All mice in CAR-T cell groups were injected intraperitoneally with $1\times10^7$ cells/time per mouse, and each mouse in the PBS group was injected intraperitoneally with 100 μL of PBS. The cell injection protocol is: injection on the Day 7 of tumor inoculation. The behavior and survival of the mice were closely observed, and the tumor development status was recorded by BLI. All optical signals and pictures were recorded and analyzed by Xenogen in vivo imaging software v2.5.

Figure 12:
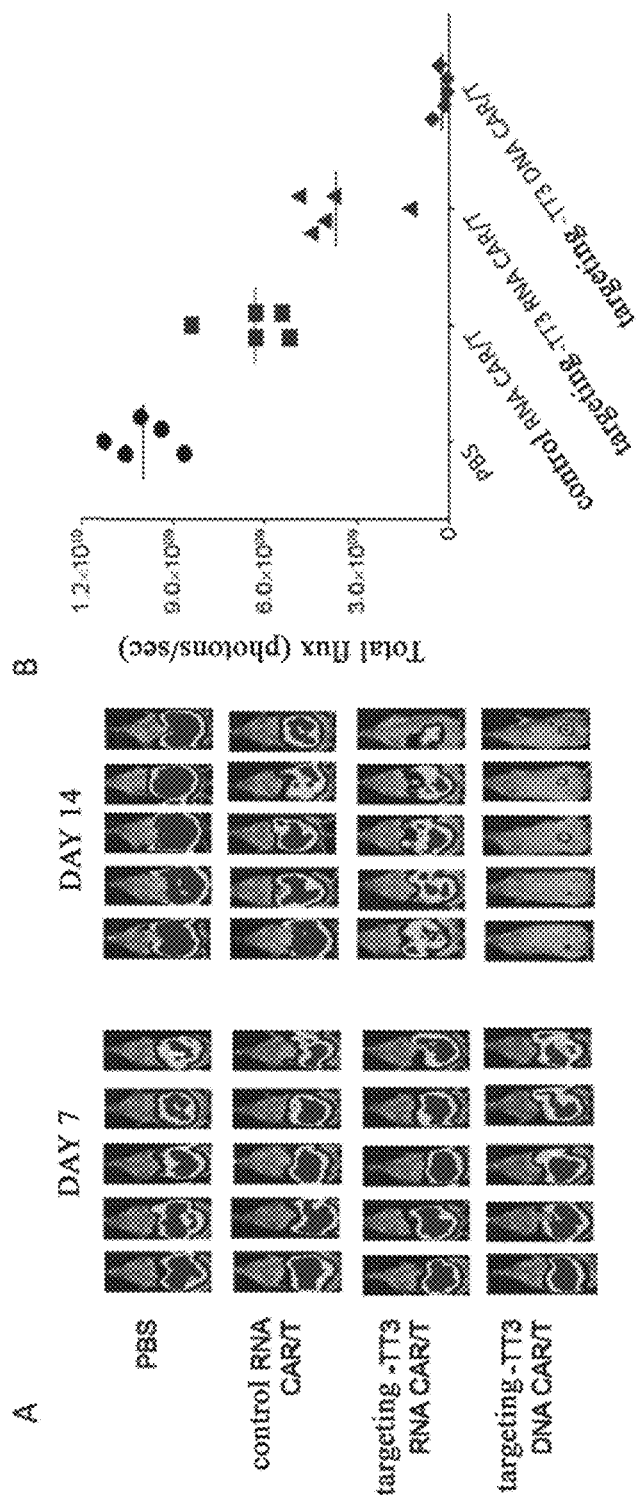
FIG. 12 shows the killing effect of adoptive reinfusion of CAR-T cells targeting TT3 on tumor cells in Example 6 of the present invention. Seven days after tumor inoculation, mice were given (1) PBS, (2) control RNA CAR-T, (3) RNA CAR-T targeting TT3, and (4) DNA CAR-T targeting TT3, respectively. FIG. A shows tumors in mice displayed by biofluorescence imaging on day 7 and day 14, respectively. FIG. B shows the BLI fluorescence intensity of tumor cells in mice on the day 14. In FIG. B, the abscissa represents the different treatment groups, and the ordinate represents the fluorescence intensity of tumor cells in the animals recorded by the in vivo imaging system. The emissivity (unit is "p/sec", that is, photon/sec) shown in the ordinate refers to the number of photons emitted from the surface of an animal per unit time.

As shown in FIG. 12, on the Day 14 after tumor implantation, the tumor growth status showed that the tumors in the PBS group continued to grow; the tumors in all 5 mice in the control RNA CAR-T cell group (shown as "control RNA CAR/T" in the figure) stopped growing, and the tumor size was significantly smaller than the PBS group; the tumor growth in the RNA CAR-T cell targeting TT3 group (shown as "RNA CAR/T targeting TT3" in the figure) was relieved, and the tumor size was significantly smaller than the control RNA CAR/T group; the tumor growth in the DNA CAR-T cell targeting TT3 group (shown as "DNA CAR/T targeting TT3" in the figure) showed a significant remission, and the tumors almost completely disappeared. It can be seen that CAR-modified T cells targeting TT3 can effectively kill tumors labeled with TT3 in vivo.

DNA CAR-T is better than RNA CAR-T because the CAR elements in the DNA CAR-T are continuously expressed and the CAR-T can continue to amplify in the body after encountering antigen; while in RNA CAR-T, the CAR elements are RNA which can only be expressed for 5 days to 7 days. During these 5 days to 7 days, the expression level will become lower and lower and the RNA will be gradually diluted as the amplification of the T cells. Therefore, DNA CAR-T is more effective than RNA CAR-T. DNA CAR-T merely requires a single injection, while RNA CAR-T requires multiple injections. However, only one injection was used herein.

Preparation Example 6: Preparation of a Recombinant Oncolytic Vaccinia Virus Comprising TT3 in the Genome by Crisper-Cas9

$4\times10^5$ CV-1 cells were resuspended in 2ml of DMEM (Gibco) medium supplemented with 10% FBS (Sigma) and inoculated into one well of a 6-well plate (Costar). After incubating overnight, the old medium was discarded. The vaccinia virus (DDVV-RFP) was diluted with serum-free DMEM medium and 1 ml of virus dilution (0.05 MOI) was added to the cells. After 4 hours of virus infection, the culture medium comprising virus was discarded and then 2 ml of DMEM culture medium comprising 5% FBS was added. 1.5 μg of Cas9 protein (purchased from IDT), 9 pmol of leader RNA-1 and 9 pmol of tracr RNA (purchased from IDT) were diluted in 37.5 μl of Opti-MEM (Gibco), incubated at room temperature for 10 minutes, named as mixture 1. Another 1.5 μg of Cas9 protein (purchased from IDT), 9 pmol of leader RNA-2 and 9 pmol of tracr RNA (purchased from IDT) were diluted in 37.5 μl of Opti-MEM (Gibco), incubated at room temperature for 10 minutes, named as mixture 2. 6 μl of Lipo3000 (purchased from Life Technologies) and 150 μl of Opti-MEM were mixed, named as mixture 3. Mixture 1, mixture 2, and 75 μl of mixture 3 were mixed together, incubated at room temperature for 15 minutes, named as mixture 4. 2 μg of donor plasmid pFastbacI-TT3-PuroGFP (as shown in FIG. 3), 4 μL of P3000 (purchased from Life Technologies) and 75 μl of Opti-MEM were mixed together, and then further mixed with 75 μl of mixture 3, incubated at room temperature for 15 minutes, named as mixture 5. Finally, mixtures 4 and 5 were mixed together and were added to the 6-well plate of CV-1 cells. At 48 hours after transfection, the supernatant and cells were collected, frozen and thaw repeatedly to obtain recombinant vaccinia virus. 143B cells were infected with the recombinant vaccinia virus and recombinants with green fluorescence can be seen. Green fluorescence was used to purify recombinants by spot screening and purified recombinant vaccinia virus (vvDD-TT3) carrying the TT3 coding sequence can be obtained.

The donor plasmid pFastbac1-TT3-PuroGFP (as shown in FIG. 3) was prepared by conventional techniques in the art, including: firstly, reforming pfastbac1 involving merely retaining pUC ori, AmpR, bla promoter, f1 ori and adding Ecor1, sai1, age1, Hindi, Kpn1 and Cla cloning sites to generate pBS1 plasmid; respectively synthesizing fragment 1 (ecor1-gRNA1-LHR480-sal1), fragment 2 (sail-TT3-age1), fragment 3 (age1-pSEL-loxp-p7.5-hind3), fragment 4 (hind3-puromycin-gfp-loxp-kpn1), fragment 5 (kpn1-RHR520-gRNA2-cla1) by IDT; connecting the five fragments into pBS1 in sequence. The nucleotide sequence of the resulting plasmid is as shown in SEQ ID NO: 38.

Preparation Example 7: Preparation of Tumor Cells Expressing TT3 on the Cell Surface by the Infection with Recombinant Oncolytic Vaccinia Virus On the Day 0, $1.5 \times 10^6$ cells of SKOV3-luc, HCT116-luc and SK-HEP-1 were inoculated to 10 cm of cell culture dishes respectively. On the Day 1, the cell culture medium (the cell culture medium of SKOV3-luc and HCT116-luc were McCoy5A+10% FBS, and the culture medium of SK-HEP-1 was EMEM+10% FBS) was discarded. The recombinant oncolytic vaccinia virus (vvDD-TT3) obtained by the method of Preparation Example 6 was diluted into 5 ml of corresponding serum-free cell culture medium respectively, and then added to SKOV3-luc, HCT116-luc and SK-HEP-1 cell culture dish, respectively. The MOI of infection was 0.02, 0.2, 0.02 respectively, and the cell culture dish was shaken gently every half an hour. After 2 hours of infection, the virus dilution was discarded and cell culture medium comprising 5% FBS (Sigma) (SKOV3-luc and HCT116-luc were McCoy5A, and SK-HEP-1 culture medium was EMEM) was added. After further culturing for 46 hours, the cells were harvested. Biotin-conjugated anti-Strep tag II antibody (Genscript) was used as the primary antibody and streptavidin-APC was used as the secondary antibody (both diluted by 1:50) for staining. Flow cytometer (purchased from BD, C6 Samplar) was used to detect the expression of TT3 on the cell surface.

Figure 13:
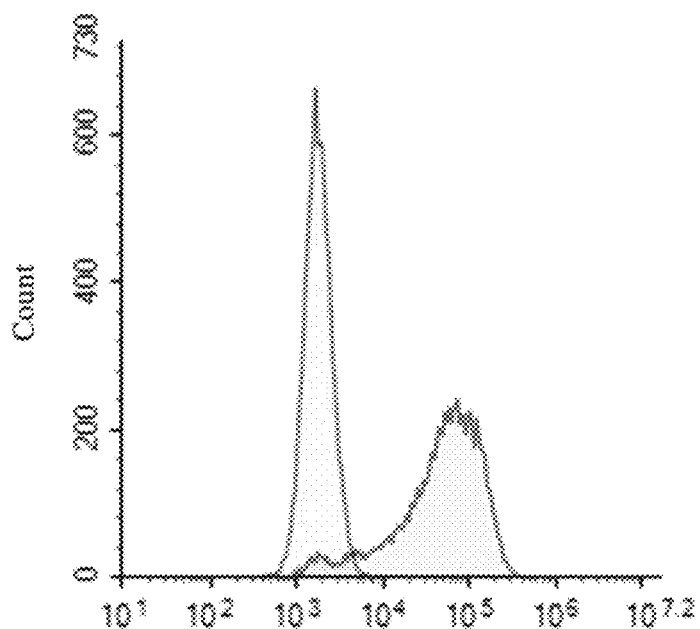
FIG. 13 shows the results of the expression of GFP and the expression of labeling polypeptide on the surface of tumor cells detected by flow cytometry after using recombinant oncolytic vaccinia virus to label tumor cells in Preparation Example 7 of the present invention. The left peak in each panel is a negative control curve of antibody-stained wild-type tumor cells (without infected with recombinant oncolytic vaccinia virus), and the right peak is the expression intensity curve of GFP (FIGS. A-C) or TT3 (FIGS. D-F) 48 hours after the tumor cells were infected with recombinant oncolytic vaccinia virus. FIGS. A and D are the results of SKOV3-luc cells; FIGS. B and E are the results of HCT116-luc cells; FIGS. C and F are the results of SK-HEP-1 cells. The abscissa in each panel represents the GFP or TT3 fluorescence intensity reading displayed by a flow cytometer, and the ordinate represents the relative cell number.
Figure 13:
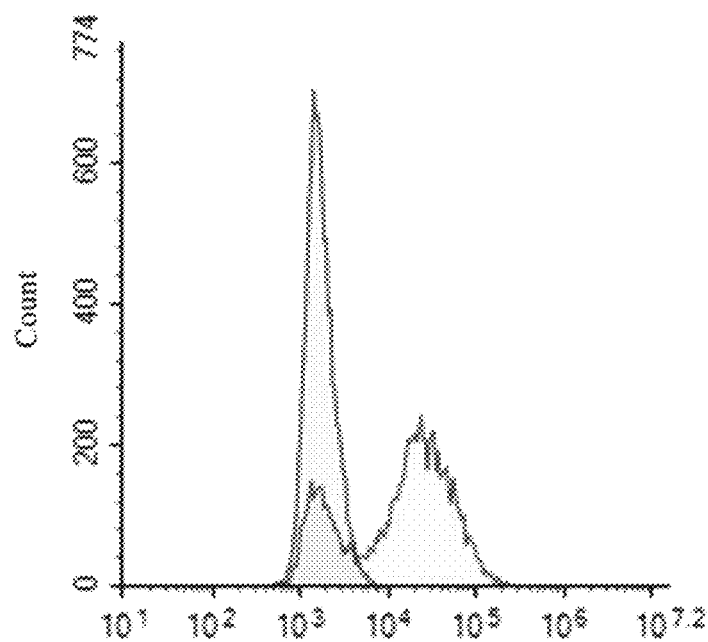
Figure 13:
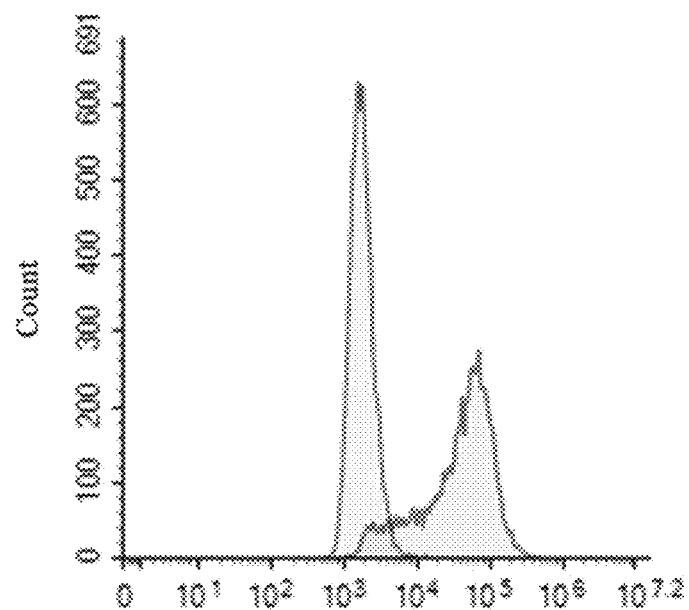
Figure 13:
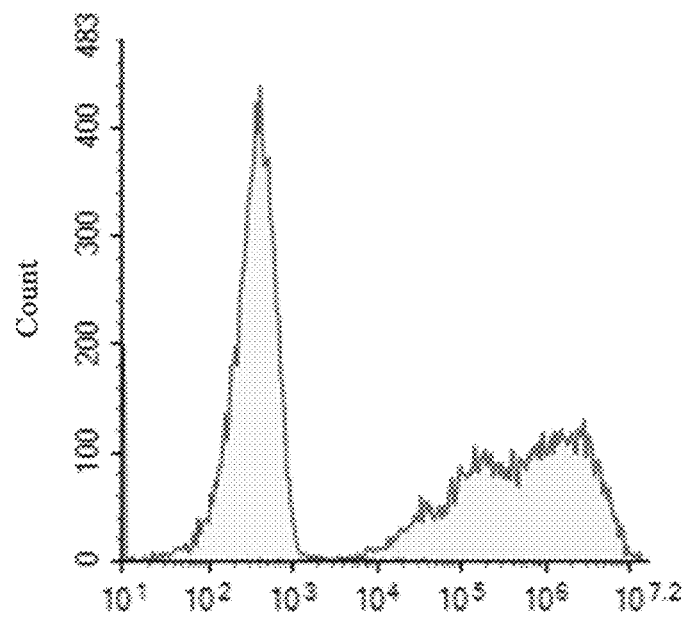
Figure 13:
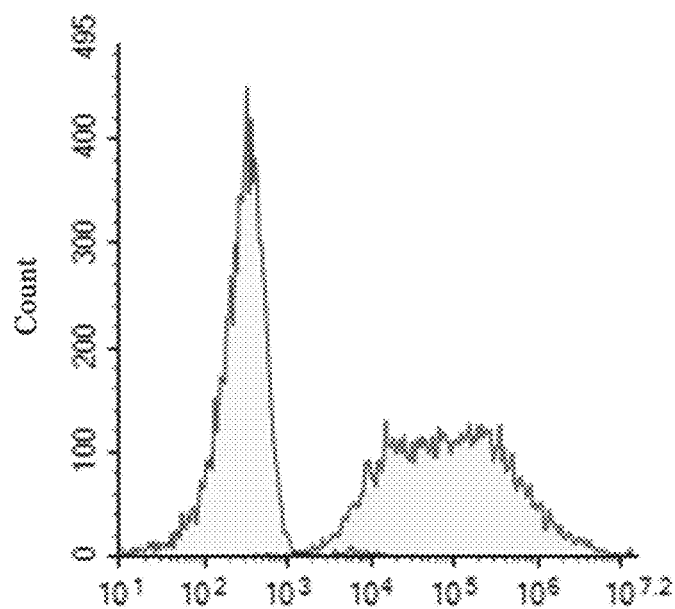
Figure 13:
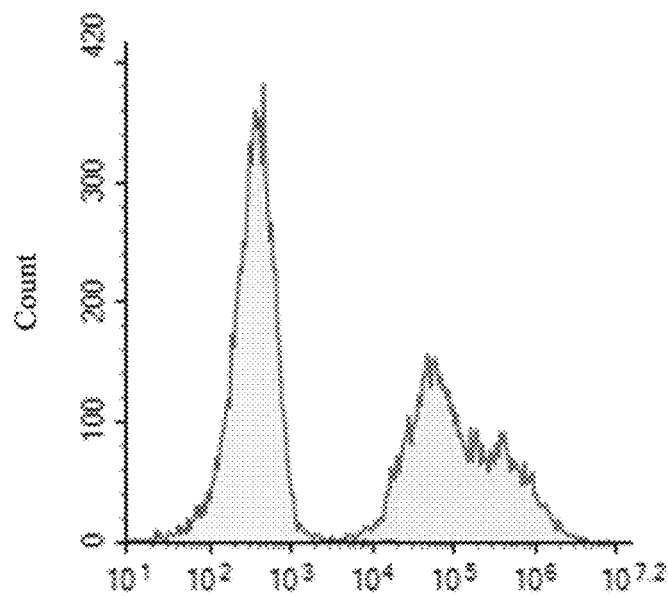

The results are shown in FIG. 13. The expression of GFP can be successfully detected and TT3 was highly expressed on the surface of infected tumor cells.

Example 7: In Vitro Killing Effect of CAR-NK Cells Targeting TT3 on Labeled Tumor Cells by Infection with Recombinant Oncolytic Vaccinia Virus This example tested the killing ability of CAR-modified NK cells targeting the labeling polypeptide on the labeled SKOV3-luc or SK-HEP-1 cells after the infection with recombinant oncolytic vaccinia virus. The CAR-modified NK cells targeting TT3 and the mGFP-Z-modified NK cells obtained according to the method of Preparation Example 3 (GFP was used to replace the antigen binding domain in aTT3-CD8-41BB-CD3ζ CAR, used as the negative control group of CAR) were respectively co-cultured with SKOV3-luc and SK-HEP-1 which were labeled with TT3 by infection with recombinant oncolytic vaccinia virus (obtained according to the method of preparation example 7; each type of tumor cells was mixed with NK cells at 48 hours after the infection with the recombinant oncolytic vaccinia virus) and unlabeled SKOV3-luc and SK-HEP-1 in a U-shaped 96-well plate, and the number ratio of CAR-NK effector cells to target cells (E:T) was 10:1. Each experiment was repeated 3 times. After 2 hours of co-cultivation, DELFIA EuTDA Cytotoxicity Kit (PerkinElmer, USA) was used to detect the ability of CAR-T cells to lyse tumor cells. The killing effect was calculated with the following formula: % specific lysis=((experimental group release (reading)−blank group release (reading))/(maximum release (reading)−blank group release (reading))×100.

Figure 14:
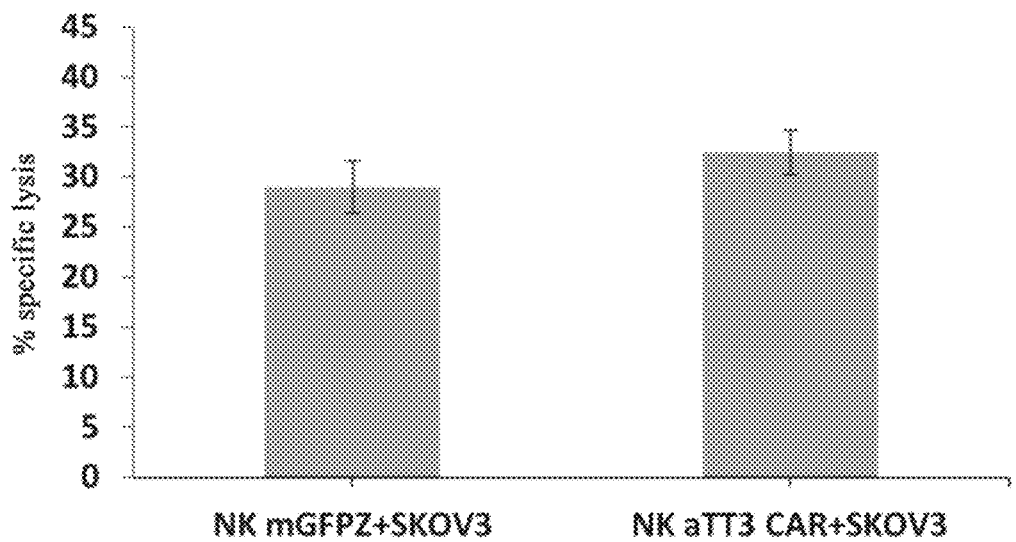
FIG. 14 shows the results of in vitro killing experiments of CAR-NK cells targeting TT3 on labeled and unlabeled SKOV3-luc or SK-HEP-1 in Example 7 of the present invention. FIG. A is the result of SKOV3-luc that is not labeled with TT3; FIG. B is the result of SKOV3-luc that is labeled with TT3 upon infection by recombinant oncolytic vaccinia virus; FIG. C is the result of SK-HEP-1 that is not labeled with TT3; FIG. D is the result of SK-HEP-1 that is labeled with TT3 upon infection by recombinant oncolytic vaccinia virus. The ordinate in each panel represents the ratio of tumor cells specifically lysed after being killed; the abscissa represents different experimental groups; the ratio of effector cells to target cells is 10:1.
Figure 14:
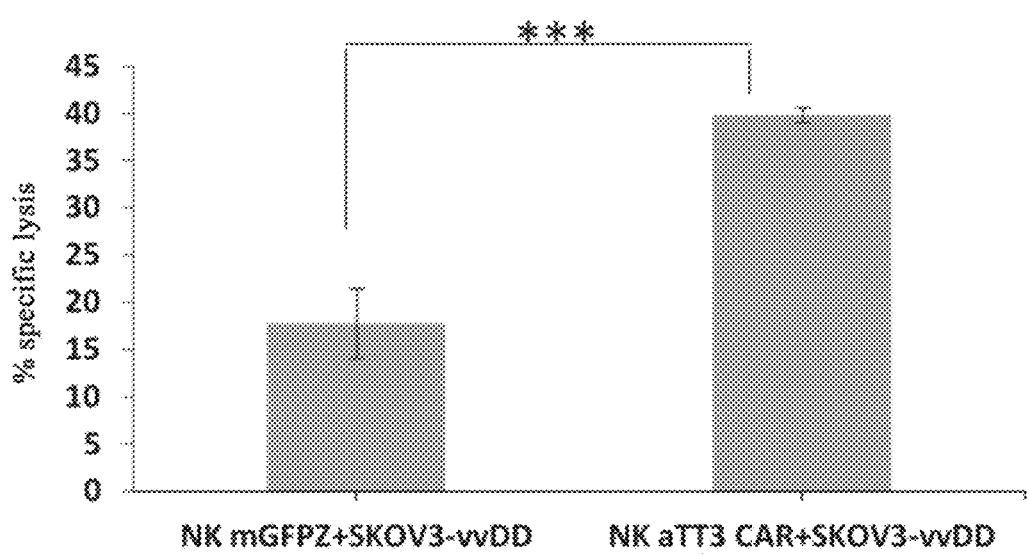
Figure 14:
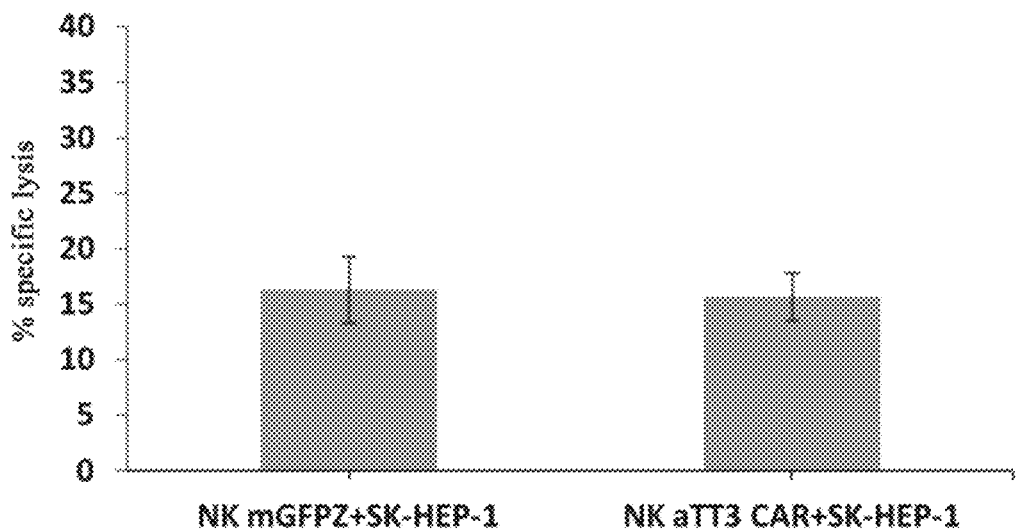
Figure 14:
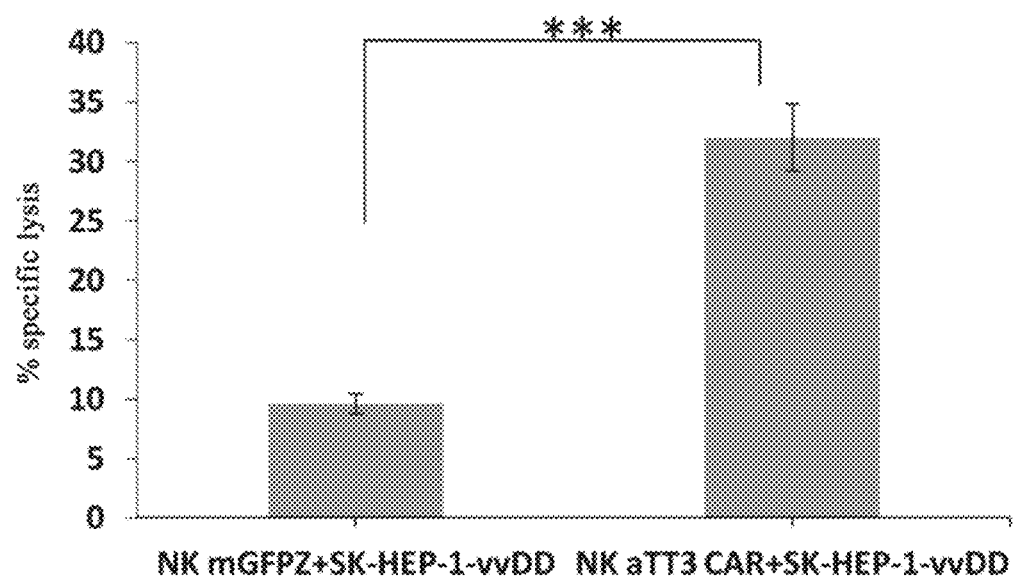

The results are shown in FIG. 14. Compared with the mGFP-Z-modified NK cells in the negative control group (shown as NK mGFPZ in the figure), CAR-NK cells targeting TT3 (shown as NK aTT3 CAR in the figure) have a significantly higher killing ability on SKOV3-luc (shown as SKOV3-vvDD in the figure) and SK-HEP-1 cells (shown as SK-HEP-1-vvDD in the figure) which were labeled with TT3 by infection with recombinant oncolytic vaccinia virus, and the killing ratio can be increased by about 18% and 23%, respectively.

Preparation Example 8: The in Vitro Synthesis of mRNAs Encoding the Labeling Polypeptides TT1, TT2, TT3, C1&2a, C1&2b, and the in Vitro Synthesis of aTT1-CD8a-4-1BB-CD3ζ mRNA Targeting TT1, aTT2-CD8a-4-1BB-CD3ζ mRNA Targeting TT2, aTT3-CD8a-4-1BB-CD3ζ mRNA Targeting TT3

Construction of recombinant expression vector pFastbac1-aTT1-CD8a-4-1BB-CD3ζ, pFastbac1-aTT2-CD8a-4-1BB-CD3ζ, pFastbac1-aTT3-CD8a-4-1BB-CD3ζ: According to conventional techniques in the art, firstly, a fragment was synthesized which orderly comprises a T7 promoter, a 5'UTR with Kozak sequence, a GM-CSFα signal peptide, multiple cloning sites containing EcoRl, Sphl, Sall, Hind III and Clal, and α globulin 3'UTR (AIT Biotech), and then was inserted into the pFastbac1 vector (Life Technologies), so that a vector pFBCMV-T7 was constructed. Then another fragment was synthesized which comprises the following sequences: a linker sequence of EcoRI restriction site, a coding sequence of chimeric antigen receptor targeting TT1, TT2 or TT3, and a linker sequence of Sall restriction site. The pFBCMV-T7 vector and the synthesized gene fragments were subjected to EcoRI and Sall (NEB) double digestion reactions, and the digested products were recovered with agarose gel DNA recovery kit for DNA fragment recovery, and then ligated and transformed into One Shot® Chemically Competent TOP10 chemically competent cells (purchased from Life Technologies), cultured at 37° C. for 18 hours. A single clone was picked and cultured at 37° C., 250 rpm for 16 hours, and extracted for plasmids by using a plasmid mini-extraction kit (purchased from Omega Bio Tek) to obtain pFastbac1-aTT1-CD8a-4-1BB-CD3ζ, pFastbac1-aTT2-CD8a-4-1BB-CD3ζ, pFastbac1-aTT3-CD8a-4-1BB-CD3ζ. All plasmids were verified by sequencing.

Construction of recombinant expression vector pFastbac1-TT1, pFastbac1-TT2, pFastbac1-TT3, pFastbac1-C1&2a, pFastbac1-C1&2b: firstly, the vector pFBCMV-T7 was obtained according to the above method, and a fragment comprising the following sequences was synthesized: a linker sequence of the EcoRI restriction site, a coding sequence of the labeling polypeptide (TT1, TT2, TT3, C1&2a or C1&2b), a linker sequence of the Sall restriction site. The pFBCMV-T7 vector and the synthesized gene fragments were subjected to EcoRI and Sall (NEB) double digestion reactions, and the digested products were recovered with agarose gel DNA recovery kit for DNA fragment recovery, and then ligated and transformed into One Shot® Chemically Competent TOP10 chemically competent cells (purchased from Life Technologies), cultured at 37° C. for 18 hours. A single clone was picked and cultured at 37° C., 250 rpm for 16 hours, and extracted for plasmids by using a plasmid mini-extraction kit (purchased from Omega Bio Tek) to obtain pFastbac1-TT1, pFastbac1-TT2, pFastbac1-TT3, pFastbac1-C1&2a, pFastbac1-C1&2b. All plasmids were correct by verification by sequencing.

Tail-PCR technique was used to synthesize a DNA double-stranded template with PolyA on the positive strand and corresponding PolyT on the reverse strand in a large-dose for in-vitro RNA synthesis, thereby the instability of the DNA template was reduced. The DNA having the coding sequence of labeling polypeptide TT1, TT2, TT3, C1&2a or C1&2b was amplified by Tail-PCR by using the pFastbac1-TT1, pFastbac1-TT2, pFastbac1-TT3, pFastbac1-C1&2a, pFastbac1-C1&2b vector as DNA template, respectively, so as to synthesize linearized DNA templates having the coding sequence of labeling polypeptide TT1, TT2, TT3, C1&2a, C1&2b, respectively.

The DNAs having chimeric antigen receptor coding sequences were obtained by Tail-PCR amplification using the pFastbac1-aTT1-CD8a-4-1BB-CD3ζ, pFastbac1-aTT2-CD8a-4-1BB-CD3ζ or pFastbac1-aTT3-CD8a-4-1BB-CD3ζ vector as DNA templates, so as to synthesize linearized DNA templates having coding sequence of chimeric antigen receptor aTT1-CD8a-4-1BB-CD3ζ, aTT2-CD8a-4-1BB-CD3ζ, aTT3-CD8a-4-1BB-CD3ζ, respectively. The condition of Tail-PCR reaction refered to the instructions of KAPA HiFiHotStartReadyMix (2×) and the reaction system (50 µL) was as follows:

Double distilled water (without nucleic acid enzyme): 25 µL
2× KAPA HiFiHotStart Uracil+ReadyMix: 25 µL
P7 (SEQ ID NO: 15) (100 µM): 0.15 µL
P8 (SEQ ID NO: 16) (100 µM): 0.15 µL
Vector DNA template (500 ng/µL): 0.5 µL The above PCR products were identified with 1% (w/v) agarose gel. The correct products after identification were used for in vitro synthesis of the mRNAs of the labeling polypeptides TT1, TT2, TT3, C1&2a, C1&2b (i.e., the mRNAs corresponding to the nucleotide sequences as shown in SEQ ID Nos: 26, 27, 28, 29 and 30, respectively) and the aTT1-CD8a-4-1BB-CD3ζ mRNA targeting TT1, aTT2-CD8a-4-1BB-CD3ζ mRNA targeting TT2, aTT3-CD8a-4-1BB-CD3ζ mRNA targeting TT3 (i.e., the mRNAs corresponding to the nucleotide sequences as shown in SEQ ID Nos: 53, 54 and 55, respectively). The capped mRNA was synthesized using an mRNA in vitro synthesis kit which was mMESSAGEmMACHINE T7 ULTRA transcription kit (available from Invitrogen, USA) or mScript™ RNA system (available from Epicentre, USA). The synthesis was followed the instructions of the kit and used the reagents provided in the kit.

The mRNA products synthesized in vitro were separated and identified with 1% (w/v) of agarose gel. The correct mRNAs after identification were stored at −80° C. for later use.

Preparation Example 9: Preparation of SK-HEP-1 cells expressing TT3 on the cell surface by infection with recombinant oncolytic vaccinia virus On the Day 0, 1×10⁶ cells of SK-HEP-1 were inoculated to 10 cm of cell culture dishes. On the Day 1, the cell culture medium (EMEM+10% FBS) was discarded. The recombinant oncolytic vaccinia virus (vvDD-TT3) obtained by the method of Preparation Example 6 was diluted into 5 ml of the corresponding serum-free cell culture medium, and then added into the SK-HEP-1 cell culture dish. The MOI of infection was 0.25 or 0.50, and the cell culture dish was shaken gently every half an hour. After 2 hours of infection, the virus dilution was discarded and EMEM cell culture medium comprising 5% FBS (Sigma) was added. After further culture of 22 hours, the cells were harvested.

The biotin-conjugated anti-Strep tag II antibody (Genscript) was used as the primary antibody and streptavidin-APC was used as the secondary antibody (both diluted by 1:50) for staining. Flow cytometer (purchased from ACEA Biosicences, Novocyte) was used to detect the expression of TT3 on the cell surface. As a result, GFP expression can be successfully detected (GFP expression can be detected directly by flow cytometer), and TT3 has high-intensity expression on the surface of infected tumor cells.

Example 8: In Vitro Killing Effect of CAR-T Targeting TT3 on Labeled Tumor Cells by Infection with Recombinant Oncolytic Vaccinia Virus This example tested the killing ability of CAR-modified T cells targeting labeling polypeptides on SK-HEP-1 cells that were labeled by infection with recombinant oncolytic vaccinia virus. The CAR modified T cells targeting TT3 and the mGFP-Z modified T cells (GFP was used to replace the antigen binding domain in aTT3-CD8-41BB-CD3ζ CAR, used as the negative control group of CAR) obtained by the method of Preparation Example 2 were co-cultured respectively with the SK-HEP-1 which was labeled with TT3 by infection with recombinant oncolytic vaccinia virus (obtained according to the method of Preparation Example 9; wherein the tumor cells were mixed with the above-mentioned T cells at 24 hours after the infection of the tumor cells with 0.25 MOI of recombinant oncolytic vaccinia virus; denoted as SK-HEP-1-vvDD) and unlabeled SK-HEP-1 (denoted as SK-HEP-1) in a U-shaped 96-well plate. The ratio of the number of the CAR-T effector cells to the target cells (E:T) is 40:1 (the number of CAR-T effector cells is 2×10⁶/well). Each experiment was repeated 3 times. After 3 hours of co-cultivation, the DELFIA EuTDA Cytotoxicity Kit (PerkinElmer, USA) was used to detect the ability of CAR-T cells to lyse tumor cells. The killing effect was calculated using the following formula: % specific lysis' ((experimental group release (reading)−blank group release (reading))/(maximum release (reading)−blank group release (reading))×100.

Figure 15:
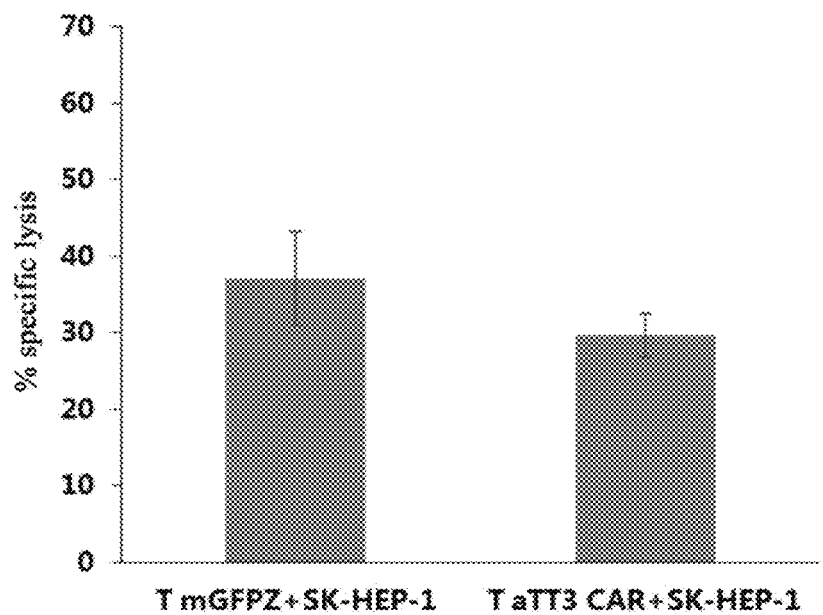
FIG. 15 shows the results of the in vitro killing experiment of the CAR-T cells targeting TT3 on the labeled or unlabeled SK-HEP-1 in Example 8 of the present invention. FIG. A is the result of SK-HEP-1 that is not labeled with TT3; FIG. B is the result of SK-HEP-1 that is labeled with TT3 after infection by recombinant oncolytic vaccinia virus ("***" indicates p<0.001). The ordinate in each figure represents the ratio of tumor cells specifically lysed after being killed, and the abscissa represents the different experimental groups, and the ratio of effector cells to target cells is 40:1.
Figure 15:
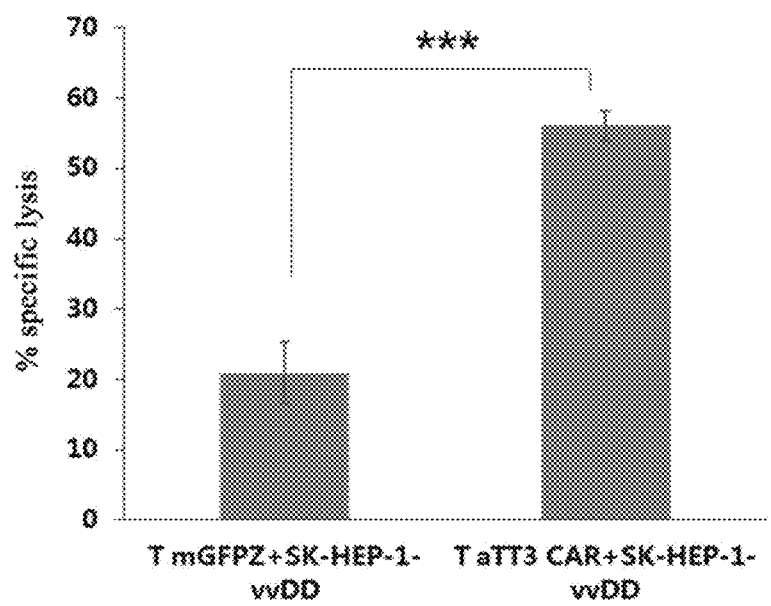

The result is shown in FIG. 15. In FIG. 15A, there was no significant difference between mGFP-Z modified T cells in the negative control group (shown as T mGFPZ in the figure) and CAR-T cells targeting TT3 (Shown as T aTT3 CAR in the figure) in terms of the killing ability to unlabeled SK-HEP-1 cells. In FIG. 15B, compared with mGFP-Z modified T cells (shown as T mGFPZ in the figure) in the negative control group, CAR-T cells targeting TT3 (shown as T aTT3 CAR in the figure) have a significantly higher killing ability on SK-HEP-1 cells labeled with TT3 by infection with recombinant oncolytic vaccinia virus, and the killing ratio can be increased by 30%.

Example 9: Cytokine Secretion of CAR-NK Cells Targeting TT3 After Co-Cultured with Labeled Tumor Cells by Infection with Recombinant Oncolytic Vaccinia virus In this example, ELISA was used to detect the secretion of GM-CSF after the CAR-modified NK cells targeting a labeling polypeptide were co-cultured with labeled SK-HEP-1 cells infected with a recombinant oncolytic vaccinia virus overnight. The CAR-modified NK cells targeting TT3 and the mGFP-Z modified NK cells obtained according to the method of Preparation Example 3 (GFP was used to replace the antigen-binding domain in aTT3-CD8-41BB-CD3ζ CAR, used as the negative control group of CAR) were co-cultured respectively with the SK-HEP-1 which was labeled with TT3 by infection with recombinant oncolytic vaccinia virus (obtained according to the method of Preparation Example 9; wherein the tumor cells were mixed with the above-mentioned NK cells at 24 hours after the infection of the tumor cells with 0.25 MOI or 0.50 MOI of recombinant oncolytic vaccinia virus, respectively; denoted as SK-HEP-1-vvDD (0.25 MOI) and SK-HEP-1-vvDD (0.5 MOI), respectively), the SK-HEP-1 labeled with TT3 by electrotransfection with mRNA encoding TT3 (obtained according to the method of the preparation example 1; denoted as SK-HEP-1-EP) and unlabeled SK-HEP-1 (denoted as SK-HEP-1) in a 24-well plate. The ratio of the number of the above CAR-NK effector cells and the target cells (E:T) is 5:1 (the number of CAR-NK effector cells is $2.5 \times 10^4$/well). After the co-cultivation overnight, the GM-CSF secretion by CAR-NK cells was detected by Human GM-CSF ELISA detection kit (R&D Company, American). Each experiment was repeated twice.

Figure 16:
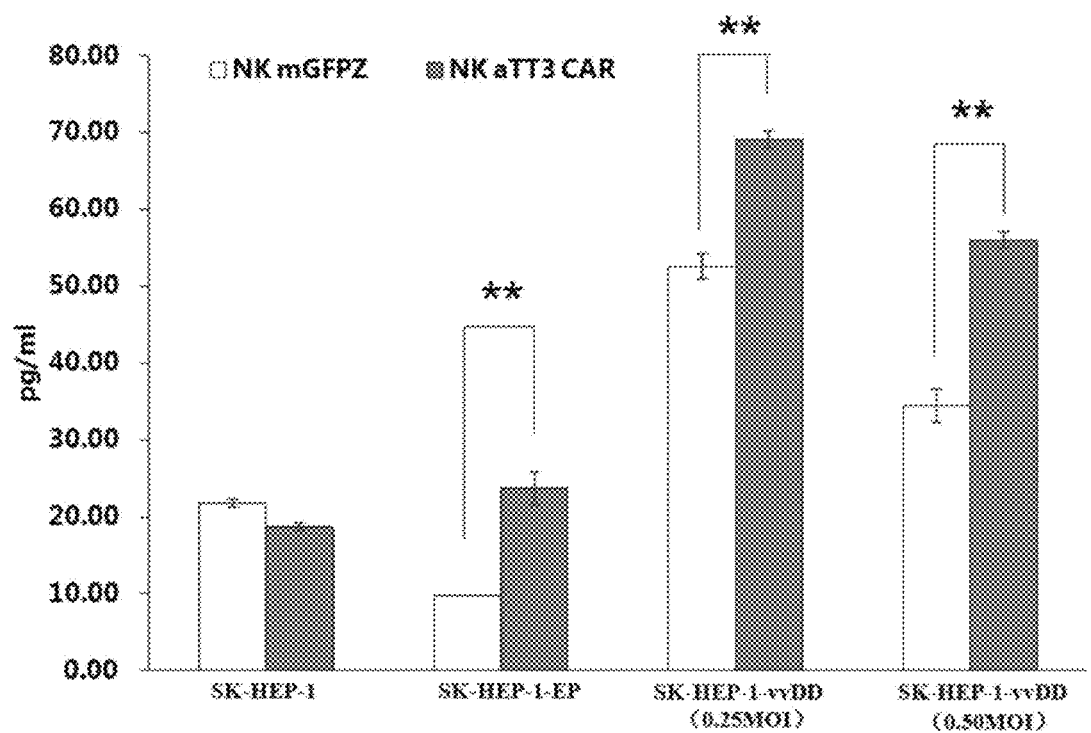
FIG. 16 shows the secretion of GM-CSF after the CAR-NK cells targeting TT3 being co-cultured with labeled or unlabeled SK-HEP-1 in Example 9 of the present invention. The ordinate in the figure represents the concentration of GM-CSF (pg/ml) in the supernatant of co-culture, and the abscissa represents different experimental groups. In the figure, the white column represents NK mGFPZ, the gray column represents NK aTT3 CAR, and "**" means p<0.01.

As shown in FIG. 16: compared with the mGFP-Z-modified NK cells in the negative control group (shown as NK mGFPZ in the figure), CAR-NK cells targeting TT3 (shown as NK aTT3 CAR in the figure) can secrete more GM-CSF after the stimulation by TT3. After co-cultivation with the TT3 labeled SK-HEP-1 (shown as SK-HEP-1-EP in the figure) by electrotransfection with mRNA encoding TT3, the GM-CSF secretion by NK aTT3 CAR was 2.4 times than that of NK mGFPZ. After co-cultivation with SK-HEP-1 which were labeled with TT3 by infection with recombinant oncolytic vaccinia virus (SK-HEP-1-vvDD (0.25 MOI) and SK-HEP-1-vvDD (0.50 MOI), respectively), the secretion of GM-CSF by NK aTT3 CAR was about 1.32 and 1.64 times than that of NK mGFPZ, respectively.

Example 10: Cytokine Secretion of CAR-T targeting TT3 After Co-Cultured WITH Labeled Tumor Cells by Infection with Recombinant Oncolytic Vaccinia Virus In this example, ELISA was used to detect the secretion of IFNα and GM-CSF after CAR-modified T cells targeting a labeling polypeptide were co-cultured with labeled SK-HEP-1 cells infected with a recombinant oncolytic vaccinia virus overnight. The CAR modified T cells targeting TT3 and the mGFP-Z modified T cells obtained according to the method of Preparation Example 3 (GFP was used to replace the antigen-binding domain in aTT3-CD8-41BB-CD3ζ CAR, used as the negative control group of CAR) were respectively co-cultured with the SK-HEP-1 which was labeled with TT3 by infection with recombinant oncolytic vaccinia virus (obtained according to the method of Preparation Example 9; wherein the tumor cells were mixed with the above-mentioned T cells at 24 hours after the infection of the tumor cells with 0.25 MOI or 0.50 MOI of recombinant oncolytic vaccinia virus, respectively; denoted as SK-HEP-1-vvDD (0.25 MOI) and SK-HEP-1-vvDD (0.5 MOI), respectively), the TT3 labeled SK-HEP-1 by electrotransfection with mRNA encoding TT3 (obtained according to the method of the preparation example 1; denoted as SK-HEP-1-EP) and unlabeled SK-HEP-1 (denoted as SK-HEP-1) in a 24-well plate. The ratio of the number of the above CAR-T effector cells and the target cells (E:T) is 5:1 (the number of CAR-T effector cells is $2.5 \times 10^4$/well). After the co-cultivation overnight, the Human IFNγ ELISA detection kit (Biolegend Company, American) was used to detect IFNγ secretion by CAR-T cell, and the Human GM-CSF ELISA detection kit (R&D Company, American) was used to detect GM-CSF secretion by CAR-T cell. Each experiment was repeated twice.

Figure 17:
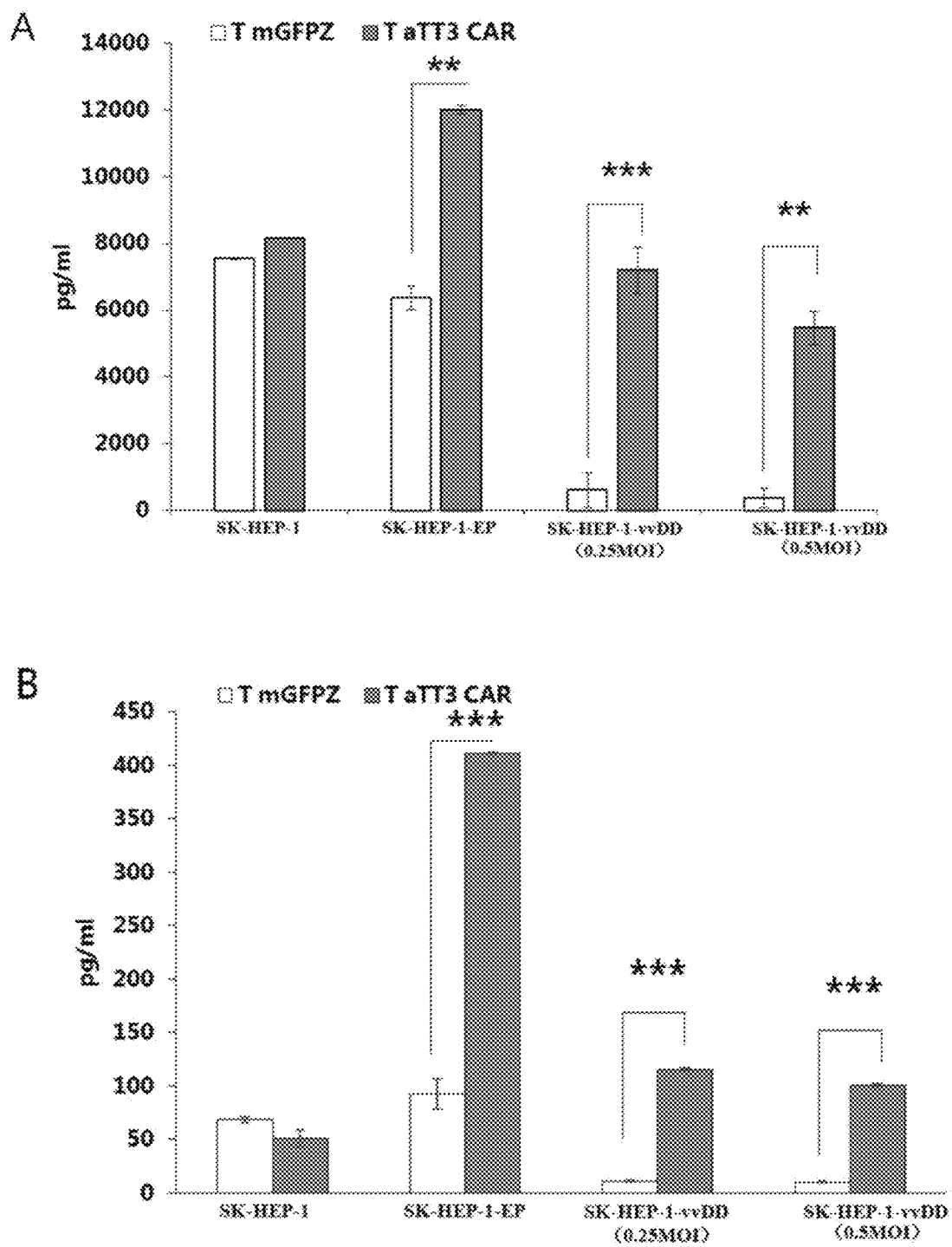
FIG. 17 shows the secretion of IFNγ (FIG. A) and GM-CSF (FIG. B) after the CAR-T cells targeting TT3 being co-cultured with labeled and unlabeled SK-HEP-1 in Example 10 of the present invention. The ordinate in the figure represents the concentration (pg/ml) of IFNγ (FIG. A) or GM-CSF (FIG. B) in the supernatant of co-culture, and the abscissa represents the different experimental groups. The white column in the figure represents T mGFPZ, and the gray column represents T aTT3 CAR.

As shown in FIG. 17: compared with the mGFP-Z-modified T cells in the negative control group (shown as T mGFPZ in the figure), CAR-T cells targeting TT3 (shown as T aTT3 CAR in the figure) can secrete more IFNγ and GM-CSF after the stimulation by TT3. After co-cultivation with the TT3 labeled SK-HEP-1 (shown as SK-HEP-1-EP in the figure) by electrotransfection with mRNA encoding TT3, the IFNγ secretion of T aTT3 CAR was about twice than that of T mGFPZ (FIG. 17A), and the GM-CSF secretion of T aTT3 CAR was about 4.45 times than that of T mGFPZ (FIG. 17B). After co-cultivation with the TT3 labeled SK-HEP-1 by infection with the recombinant oncolytic vaccinia virus (SK-HEP-1-vvDD (0.25 MOI) and SK-HEP-1-vvDD (0.5 MOI), respectively), the IFNγ secretion of T aTT3 CAR was about 11.5 times and 14.2 times than that of T mGFPZ (FIG. 17A), respectively, and the GM-CSF secretion of T aTT3 CAR was about 10 times and 10 times than that of T mGFPZ, respectively (FIG. 17B).

Example 11: Distribution of TT3 in Tumor Tissue after Intratumoral Injection of Recombinant Oncolytic Vaccinia Virus The experimental mice were non-obese diabetes/severe combined immunodeficiency/IL-2Rγcnull (NCG) mice (6-8 weeks, female, obtained from Jiangsu Jicui Yaokang Biotechnology Co., Ltd.). Each mouse was implanted subcutaneously with $1 \times 10^7$ cells of human liver cancer cell line SK-HEP-1. Six days after the tumor implantation, 12 mice with tumor size ranging from 80-120mm$^3$ with good molding quality were selected and were injected with 50 μl $5 \times 10^6$ pfu vvDD-TT3 per mouse via intratumoral injection. On the 7, 14, 21, and 29 days after the vaccinia virus injection, respectively, 3 mice were randomly sacrificed, and the subcutaneous tumor tissues were stripped. The tumor tissues were cut from the middle by a scalpel, fixed and embedded in paraffin, and prepared into slices with 5 μm thickness. All slices were stained with hematoxylin (obtained from Shanghai Beyotime Biotechnology Co., Ltd.) for nuclear staining, and TT3 was detected with biotin anti-strep tag II antibody (Genscript) at the same time. The secondary antibody was a rabbit two-step detection kit (obtained from Beijing Zhongshan Jinqiao Biotechnology Co., Ltd.), and the color development kit was a DAB horseradish peroxidase color development kit (obtained from Shanghai Beyotime Biotechnology Co., Ltd.). Finally, the panoramic scanning of the slices was performed by Jiangfeng automatic digital pathological slice scanner.

Figure 18:
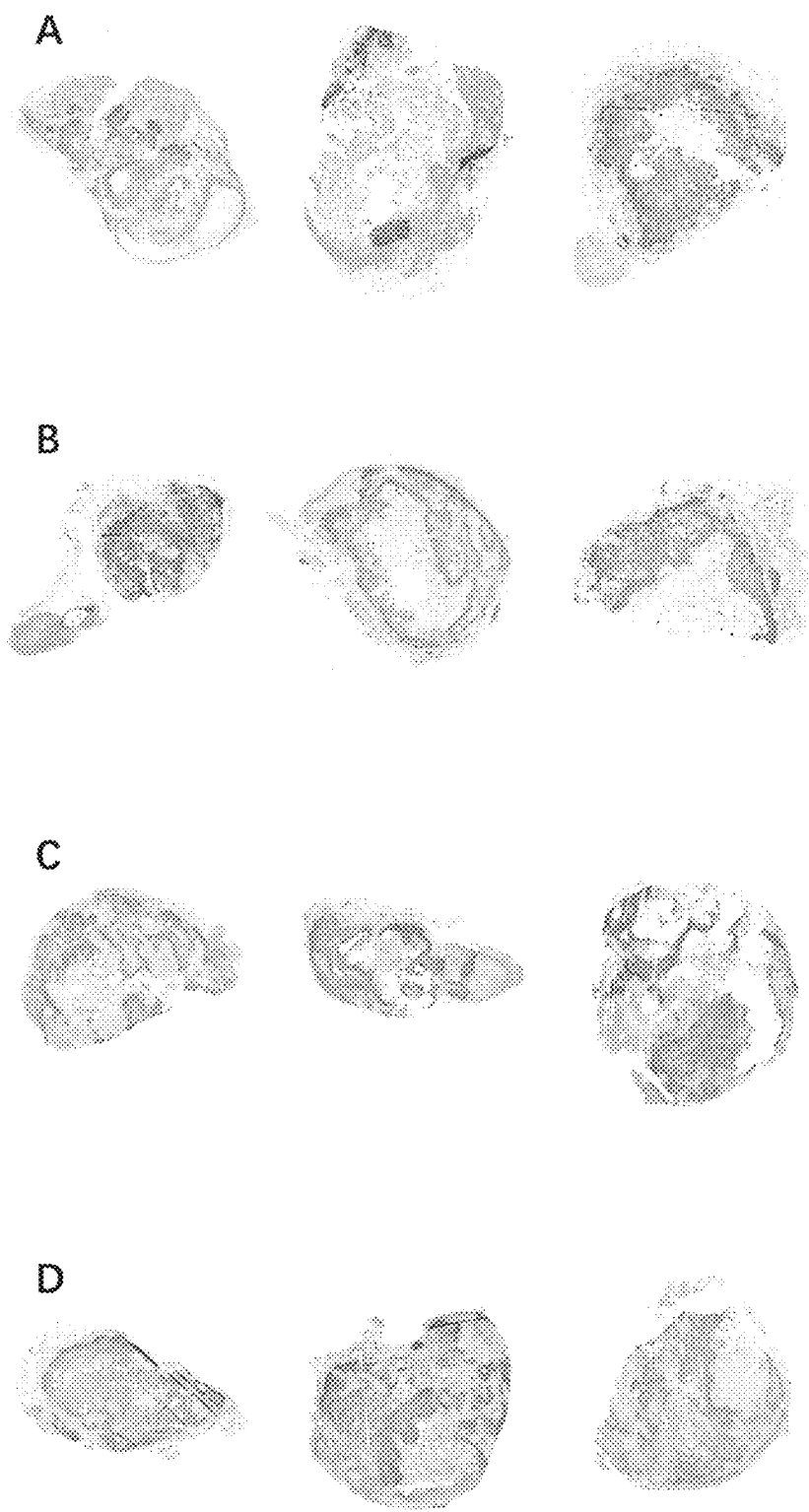
FIG. 18 shows the expression of TT3 in tumor tissues after intratumoral administration of recombinant oncolytic vaccinia virus detected by immunohistochemistry in Example 11 of the present invention. The FIGS. A-D represent the expression of TT3 in tumor tissues at 7 (A), 14 (B), 21 (C), 29 (D) days after intratumoral injection of recombinant oncolytic vaccinia virus, respectively. The three sections in each figure are from the tumor tissue of three mice respectively, and the magnification range is from 0.5 to 1.5 folds.

The result was shown in FIG. 18. In FIG. 18, light gray was TT3 negative part and dark gray was TT3 positive area. It can be seen that on 7, 14, 21, 29 days after intratumoral injection of vvDD-TT3, the expression of TT3 can be detected in tumor tissues, and TT3 was widely distributed in tumor tissues.

Example 12: The Effect of Combined Administration of Recombinant Oncolytic Vaccinia Virus and CAR-NK on the Growth of Subcutaneous Tumors in Mice Experimental mice were non-obese diabetes/severe combined immunodeficiency/IL-2Rγcnull (NCG) mice (aged 6 weeks to 8 weeks, female, obtained from Jiangsu Jicui Yaokang Biotechnology Co., Ltd.). Each mouse was implanted subcutaneously with 1×10⁷ cells of human liver cancer cell line SK-HEP-1. Six days after tumor implantation, 30 mice with tumor size ranging from 80-120mm³ with good molding quality were selected and randomly divided into 6 groups, 5 mice in each group. The first group was the "blank control" group (IL-2/PBS/0.9% NaCl), wherein 6 days after tumor inoculation, 50 µl of PBS was injected intratumorally (denoted as "Day 0 after administration"), and 10 days after PBS injection (that is, on Day 10 after administration), 100 µl of 0.9% NaCl was injected intratumorally, and IL-2 was injected intraperitoneally on Day 10, 12, 14, 16, 18, 20, 22, 24, and 26 after administration. The second group was "vvDD-TT3" group (that is, the recombinant oncolytic vaccinia virus single-drug group (IL-2/vvDD-TT3/0.9% NaCl)), wherein 6 days after tumor inoculation, 50 µl vvDD-TT3 was injected intratumorally (denoted as "Day 0 after administration"), and 10 days after the vvDD-TT3 injection (that is, on Day 10 after administration), 100 µl of 0.9% NaCl was injected intratumorally, and IL-2 was injected intraperitoneally on Day 10, 12, 14, 16, 18, 20, 22, 24, 26 after administration. The third group was the "NK mGFPZ" group (that is, the negative CAR NK single-drug control group (IL-2/PBS/NK mGFPZ)), wherein 6 days after tumor inoculation, 50 µl PBS was injected intratumorally (denoted as "Day 0 after administration"), and 10, 13, 16, 19, 23, 26 days after PBS injection (that is, on Day 10, 13, 16, 19, 23, 26 after administration), 100 µl of NK mGFPZ was injected intratumorally, and IL-2 was injected intraperitoneally on Day 10, 12, 14, 16, 18, 20, 22, 24, 26 after administration. The fourth group was the "NK aTT3 CAR" group (that is, the positive CAR NK single-drug group (IL-2/PBS/NK aTT3 CAR)), wherein 6 days after tumor inoculation, 50 µl PBS was injected intratumorally (denoted as "Day 0 after administration"), and 10, 13, 16, 19, 23, and 26 days after PBS injection (that is, on Day 10, 13, 16, 19, 23, 26 after administration), 100 µl NK aTT3 CAR was injected intratumorally, and IL-2 was injected intraperitoneally on Day 10, 12, 14, 16, 18, 20, 22, 24, 26 after administration. The fifth group was the "vvDD-TT3+ NK mGFPZ" group (that is, the combined administration control group (IL-2/vvDD-TT3/NK mGFPZ)), wherein 6 days after tumor inoculation, 50 µl of vvDD-TT3 was injected intratumorally (denoted as "Day 0 after administration"), and 10, 13, 16, 19, 23, and 26 days after vvDD-TT3 injection (that is, on Day 10, 13, 16, 19, 23, 26 after administration), 100 µl of NK mGFPZ was injected intratumorally, and IL-2 was injected intraperitoneally on Day 10, 12, 14, 16, 18, 20, 22, 24, 26 after administration. The sixth group was the "vvDD-TT3+NK aTT3 CAR" group (that is, the combined administration group of the present invention (IL-2/vvDD-TT3/NK aTT3 CAR)), wherein 6 days after tumor inoculation, 50 µl vvDD-TT3 was injected intratumorally (denoted as "Day 0 after administration"), and 10, 13, 16, 19, 23, and 26 days after vvDD-TT3 injection (that is, on Day 10, 13, 16, 19, 23, 26 after administration), 100 µl NK aTT3 CAR was injected intratumorally, and IL-2 was injected intraperitoneally on Day 10, 12, 14, 16, 18, 20, 22, 24, 26 after administration. NK mGFPZ and NK aTT3 CAR were prepared according to the method of Preparation Example 3. CAR-NK cells were administrated by way of intratumoral injection of 1×10⁷ cells per mouse every time, IL-2 was injected intraperitoneally in the amount of 20000 IU per mouse every time, and the administration dose of vvDD-TT3 was 5×10⁶ pfu per mouse. The long diameter and short diameter of the tumor were measured and recorded with a vernier caliper on the day of grouping, twice a week after the first administration, and before euthanasia, respectively. The tumor volume was calculated and the tumor growth curve was drawn based on the tumor volume. The calculation formula of tumor volume is V=½×long diameter×short diameter². The calculation formula of relative tumor volume (RTV) is RTV=Vt/V0, wherein the Vt was the tumor volume obtained by each measurement, the V0 was the initial tumor volume (before administration). The calculation formula of relative tumor proliferation rate (T/C)% was T/C %=average RTV of the administration group/average RTV of the blank control group×100%, wherein if T/C %≤40%, the RTV of the experimental group to the RTV of the model group was statistically P<0.05, which means that there is inhibitory effect on tumor growth. On the contrary, if T/C %>40%, there is no inhibitory effect on tumor growth.

Figure 19:
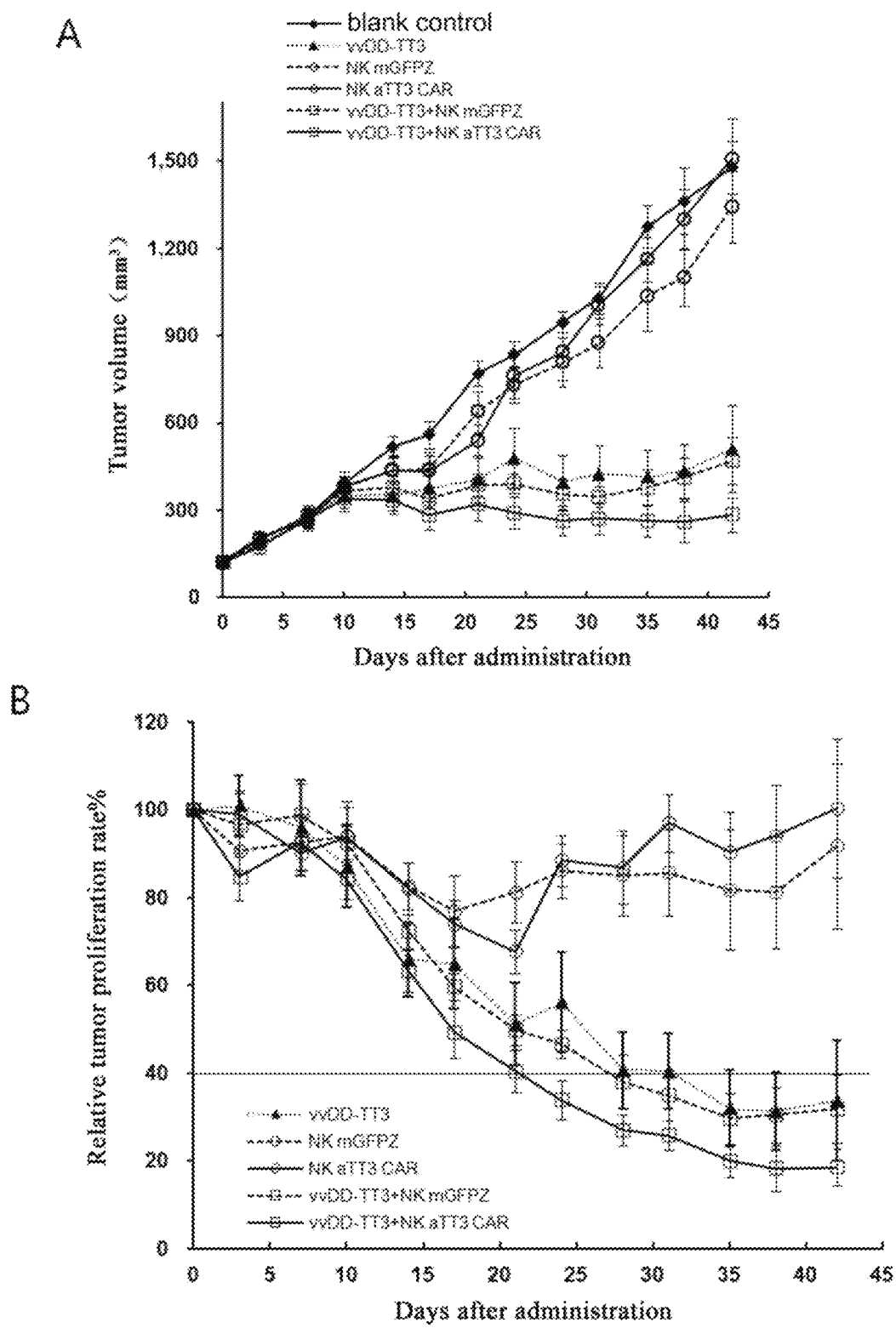
FIG. 19 shows the inhibitory effect of the combination of recombinant oncolytic vaccinia virus and CAR-NK on the growth of subcutaneous tumors in mice in Example 12 of the present invention. FIG. A shows the growth curves of subcutaneous tumors in mice in different administration groups. The abscissa represents the number of days after the administration of recombinant oncolytic vaccinia virus, and the ordinate represents the volume of the tumor. FIG. B shows the relative proliferation rate of subcutaneous tumors in mice in different administration groups as a function of the number of days after administration. The abscissa represents the number of days after the administration of recombinant oncolytic vaccinia virus, and the ordinate represents the relative tumor proliferation rate %.

As shown in FIG. 19A, after tumor implantation, the tumor growth status showed that the tumors in mice in the first group, i.e., "blank control" group, grew continuously; in the second group, i.e., "vvDD-TT3" group, the tumor growth could be significantly inhibited; in the third group, i.e., "NK mGFPZ" group and the fourth group, i.e., "NK aTT3 CAR" group, the tumor growth could be weakly delayed; in the fifth group, i.e., "vvDD-TT3+NK mGFPZ" group, the tumor growth could be further inhibited compared to the "vvDD-TT3" group; in the sixth group, i.e., "vvDD-TT3+NK aTT3 CAR" group, the tumor growth could be further inhibited compared to the fifth group, and even the tumor burden could be reduced. As shown in FIG. 19B, the relative tumor inhibition rate of the sixth group "vvDD-TT3+NK aTT3 CAR" had reached 40% on Day 21 after administration, while in the second group "vvDD-TT3" group and the fifth group "vvDD-TT3+NK mGFPZ" group, the relative tumor inhibition rate reached 40% on Day 28 after administration. It can be seen that the vvDD-TT3 and NK cells modified by CAR targeting TT3 can be combined to specifically treat tumors and inhibit tumor growth faster.

What is claimed is:

1. A therapeutic agent for treatment of tumors and/or cancers, comprising:
   (a) a first composition, wherein the first composition comprises a first active ingredient in a first pharmaceutically acceptable carrier, and the first active ingredient includes or contains a nucleic acid having a labeling polypeptide coding sequence for being introduced into a tumor cell and/or a cancer cell; the labeling polypeptide has a extracellular antigen determining region, a spacer portion and a transmembrane portion that are operatively linked, which can be expressed to form modification on the surface of the tumor cell and/or cancer cell; an amino acid sequence of the extracellular antigen determining region comprises one or more amino acid sequences of epitope polypeptide; and wherein, in the natural state, an amino acid sequence of a protein on cell membrane or a secreted protein of mammal does not comprise the amino acid sequence of the epitope polypeptide; and
   (b) a second composition, wherein the second composition comprises a second active ingredient in a second pharmaceutically acceptable carrier, and the second active ingredient comprises a chimeric antigen receptor-modified immune cell; the chimeric antigen receptor-modified immune cell can specifically recognize and bind to the extracellular antigen determining region of the labeling polypeptide;
   wherein the spacer portion is derived from the hinge region of CD8α, the hinge region of IgG or the hinge region of IgD;
   wherein the amino acid sequence of the epitope polypeptide includes an amino acid sequence of the following tags: Myc tag, HA tag, Strep tag II, Flag tag, HAT tag, S tag, S1 tag, protein C tag, tag-100 tag, E2 tag, TAP tag, HSV tag, KT3 tag, V5 tag, VSV-G tag, His tag or RFP tag; and
   wherein the amino acid sequence of the extracellular antigen determining region is as shown in SEQ ID NO: 1, SEQ ID NO: 2, SEQ ID NO: 3, SEQ ID NO: 4 or SEQ ID NO: 5.

2. The therapeutic agent of claim 1, wherein an amino acid sequence of the spacer portion is as shown in SEQ ID NO: 6; wherein the transmembrane portion is derived from the transmembrane region of CD8, CD3ζ, CD4 or CD28.

3. The therapeutic agent of claim 1, wherein an amino acid sequence of the labeling polypeptide is as shown in SEQ ID NO: 11, SEQ ID NO: 12, SEQ ID NO: 13, SEQ ID NO: 14 or SEQ ID NO: 15.

4. The therapeutic agent of claim 1, wherein the nucleic acid includes DNA or RNA; and the RNA includes mRNA transcribed from the DNA;
   wherein the first composition comprises a therapeutically effective amount of the DNA or a therapeutically effective amount of the mRNA; and wherein the DNA is formulated to be administered by intratumoral injection or intravenously; and the mRNA is formulated to be administered by intratumoral injection or intravenously.

5. The therapeutic agent of claim 1, wherein the first active ingredient is a recombinant virus, and the genome of the recombinant virus has the labeling polypeptide coding sequence; wherein the recombinant virus includes replication-selective recombinant oncolytic virus or replication-defective recombinant virus; wherein the first composition comprises a therapeutically effective amount of the recombinant virus; and wherein the recombinant virus is formulated to be administered by intratumoral injection or intravenously.

6. The therapeutic agent of claim 5, wherein the recombinant oncolytic virus is derived from a genetically mutated virus with oncolytic effect or a wild-type virus with oncolytic effect.

7. The therapeutic agent of claim 1, wherein a chimeric antigen receptor of the chimeric antigen receptor-modified immune cell includes an antigen-binding domain, a spacer region, a transmembrane region and an intracellular domain that are operatively and orderly linked, and the antigen-binding domain can specifically recognize and bind to the extracellular antigen determining region of the labeling polypeptide.

8. The therapeutic agent of claim 5, wherein the recombinant oncolytic virus is derived from adenovirus, poxvirus, herpes simplex virus, measles virus, Semliki forest virus, vesicular stomatitis virus, polio virus, retrovirus, reovirus, Seneca valley virus, Echo-type enterovirus, Coxsackie virus, Newcastle disease virus and Malaba virus with oncolytic effect.

9. The therapeutic agent of claim 7, wherein an amino acid sequence of the antigen-binding domain is as shown in SEQ SEQ ID NO: 44.

10. The therapeutic agent of claim 7, wherein the intracellular domain is derived from a lymphocyte intracellular activation signal transduction region, wherein the intracellular activation signal transduction region is selected from an intracellular activation signal transduction region of CD3ζ or DAP12.

11. The therapeutic agent of claim 7, wherein the spacer region is derived from a hinge region of CD8α, a hinge region of IgG or a hinge region of IgD, and a transmembrane region is derived from a transmembrane region of CD8α, CD3ζ, CD4 or CD28.

12. The therapeutic agent of claim 7, wherein the intracellular domain is derived from a lymphocyte intracellular activation signal transduction region and a lymphocyte costimulatory signal transduction region, wherein the intracellular activation signal transduction region is selected from an intracellular activation signal transduction region of CD3ζ or DAP12; the lymphocyte costimulatory signal transduction region is selected from a costimulatory signal transduction region of 4-1BB, CD28, CD27, OX40, GITR, and/or ICOSS.

13. The therapeutic agent of claim 7, wherein the amino acid sequence of the chimeric antigen receptor is as shown in SEQ ID NO: 48.

14. The therapeutic agent of claim 1, wherein the immune cells include T cells or NK cells.

15. The therapeutic agent of claim 1, wherein the first composition and the second composition are present separately in the therapeutic agent without being mixed together.

16. The therapeutic agent of claim 1, wherein the second composition comprises a therapeutically effective amount of the chimeric antigen receptor-modified immune cell; and wherein the chimeric antigen receptor-modified immune cell is formulated to be administered intravenously or locally.

17. The therapeutic agent of claim 1, wherein an amino acid sequence of the transmembrane portion is as shown in SEQ ID NO: 7.

* * * * *